(12) United States Patent
Sibley et al.

(10) Patent No.: US 10,596,150 B2
(45) Date of Patent: *Mar. 24, 2020

(54) ANTIFUNGAL AGENTS

(71) Applicant: F2G LIMITED, Manchester (GB)

(72) Inventors: Graham Edward Morris Sibley, Stockport (GB); Derek Law, Bolton (GB); Jason David Oliver, Cheshire (GB); Michael Birch, Manchester (GB)

(73) Assignee: F2G LIMITED, Manchester (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/222,764

(22) Filed: Dec. 17, 2018

(65) Prior Publication Data

US 2019/0314333 A1 Oct. 17, 2019

Related U.S. Application Data

(63) Continuation of application No. 15/528,457, filed as application No. PCT/GB2015/053546 on Nov. 20, 2015, now Pat. No. 10,201,524.

(30) Foreign Application Priority Data

Nov. 21, 2014 (GB) .................................. 1420743.5
Apr. 7, 2015 (GB) .................................... 1505891

(51) Int. Cl.
*A61K 31/4025* (2006.01)
*A61K 31/496* (2006.01)
*C07D 403/14* (2006.01)

(52) U.S. Cl.
CPC ........ *A61K 31/4025* (2013.01); *A61K 31/496* (2013.01); *C07D 403/14* (2013.01)

(58) Field of Classification Search
CPC .......................... A61K 31/4025; A61K 31/496
See application file for complete search history.

(56) References Cited

U.S. PATENT DOCUMENTS 3,202,654 A 8/1965 Perron
3,252,970 A 5/1966 Huebner
(Continued)

FOREIGN PATENT DOCUMENTS

DE 2 253 150 A1 5/1973
DE 2 429 923 A1 1/1975
(Continued)

OTHER PUBLICATIONS

Alvarez, M. et al. (1999). "Synthesis of 1,2-Dihydropyrrolo[1,2-c]Pyrimidin-1-Ones," *Journal of Chemical Society* 249-255.
(Continued)

*Primary Examiner* — San Ming R Hui
(74) *Attorney, Agent, or Firm* — Morrison & Foerster LLP

(57) ABSTRACT

The invention provides a pyrrole compound, which compound is (a) 2-(1,5-dimethyl-3-phenyl-1H-pyrrol-2-yl)-N-(4-(4-(5-fluoropyrimidin-2-yl)piperazin-1-yl)phenyl)-2-oxoacetamide or a deuterated derivative thereof, or (b) 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide or a deuterated derivative thereof, or (c) a prodrug of compound (a) or a prodrug of compound (b), or a pharmaceutically acceptable salt or agriculturally acceptable salt of (a), (b) or (c). Also provided are combinations and compositions comprising the compound and known antifungal agents. The invention also relates to the therapeutic use of a compound of the invention in prevention or treatment of fungal diseases. It also relates to the use of: 2-(1,5-dimethyl-3-phenyl-1H-pyrrol-2-yl)-N-(4-(4-(5-fluoropyrimidin-2-yl)piperazin-1-yl)phenyl)-2-oxoacetamide or an agriculturally acceptable salt thereof, or 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide or an (Continued)

agriculturally acceptable salt thereof, as an agricultural fungicide.

19 Claims, 8 Drawing Sheets

(56) References Cited

U.S. PATENT DOCUMENTS

| | | | |
|---|---|---|---|
| 3,256,279 | A | 6/1966 | Karmas |
| 3,458,515 | A | 7/1969 | Archibald et al. |
| 3,573,294 | A | 3/1971 | Long et al. |
| 3,857,857 | A | 12/1974 | Bella et al. |
| 4,148,907 | A | 4/1979 | Conti |
| 4,316,900 | A | 2/1982 | Wasley |
| 4,761,424 | A | 8/1988 | Carethers et al. |
| 4,794,120 | A | 12/1988 | Manoury et al. |
| 5,750,540 | A | 5/1998 | Tsuchiya et al. |
| 6,645,976 | B1 | 11/2003 | Dillard et al. |
| 8,524,705 | B2 | 9/2013 | Payne et al. |
| 8,993,574 | B2 | 3/2015 | Sibley et al. |
| 9,452,168 | B2 | 9/2016 | Sibley et al. |
| 10,201,524 | B2 | 2/2019 | Sibley et al. |
| 2005/0090541 | A1 | 4/2005 | Arnaiz et al. |
| 2006/0058286 | A1 | 3/2006 | Krystal et al. |

FOREIGN PATENT DOCUMENTS

| | | | |
|---|---|---|---|
| DE | 2 751 571 A1 | 5/1978 | |
| EA | 200101172 A1 | 4/2002 | |
| EP | 0 252 809 A2 | 1/1988 | |
| EP | 0 505 321 | 9/1992 | |
| EP | 0 747 756 A1 | 12/1996 | |
| EP | 1857113 A2 * | 11/2007 | ........... A61K 9/0043 |
| EP | 2626361 A1 | 8/2013 | |
| FR | 1 381 256 | 12/1964 | |
| FR | 1 556 822 A | 2/1969 | |
| GB | 1051723 | 12/1966 | |
| GB | 1208014 | 10/1970 | |
| GB | 1476503 | 6/1977 | |
| JP | 57-142966 A | 9/1982 | |
| JP | 57-144255 A | 9/1982 | |
| JP | 62-081369 A | 4/1987 | |
| JP | 9-249669 A | 9/1997 | |
| RU | 2152392 C1 | 7/2000 | |
| WO | WO-96/01822 A1 | 1/1996 | |
| WO | WO-96/03383 A1 | 2/1996 | |
| WO | WO-96/33973 A1 | 10/1996 | |
| WO | WO-99/62881 A1 | 12/1999 | |
| WO | WO-00/32588 A2 | 6/2000 | |
| WO | WO-00/32588 A3 | 6/2000 | |
| WO | WO-00/66580 A2 | 11/2000 | |
| WO | WO-00/66580 A3 | 11/2000 | |
| WO | WO-02/085301 A2 | 10/2002 | |
| WO | WO-02/085301 A3 | 10/2002 | |
| WO | WO-02/085907 A1 | 10/2002 | |
| WO | WO-02/098876 A1 | 12/2002 | |
| WO | WO-03/000680 A1 | 1/2003 | |
| WO | WO-03/064397 A1 | 8/2003 | |
| WO | WO-03/072028 A2 | 9/2003 | |
| WO | WO-03/072028 A3 | 9/2003 | |
| WO | WO-2004/082606 A2 | 9/2004 | |
| WO | WO-2004/082606 A3 | 9/2004 | |
| WO | WO-2006/105289 A1 | 10/2006 | |
| WO | WO-2006/113875 A2 | 10/2006 | |
| WO | WO-2006/113875 A3 | 10/2006 | |
| WO | WO-2006/123145 A1 | 11/2006 | |
| WO | WO-2007/015866 A2 | 2/2007 | |
| WO | WO-2007/015866 A3 | 2/2007 | |
| WO | WO-2007/092681 A2 | 8/2007 | |
| WO | WO-2007/092681 A3 | 8/2007 | |
| WO | WO-2008/046082 A2 | 4/2008 | |
| WO | WO-2008/046082 A3 | 4/2008 | |
| WO | WO-2008/062182 A1 | 5/2008 | |
| WO | WO-2008/106860 A1 | 9/2008 | |
| WO | WO-2008/145963 A1 | 12/2008 | |
| WO | WO-2009/130481 A1 | 10/2009 | |
| WO | WO-2009/144473 A1 | 12/2009 | |

OTHER PUBLICATIONS

Alves, M.J. et al. (2000). "Novel Aziridine Esters by the Addition of Aromatic Nitrogen Heterocycles to a 2H-Azirine-3-Carboxylic Ester," *Tetrahedron Letters* 41:4991-4995.

Ames, D.E. et al. (1959, e-published Jan. 1, 1959). "The Preparation of Aminoalkylpyrrocolines," *Journal of Chemical Society* 124:620-622.

Anonymous. (2012). "Diethyl Ether," Located at <http:www.merckmillipore.com/chemicals/diethyl-ether/MDA_CHEM-100926/p_NgGb.s1Lay4AAAEW8uEfVhTI>, last visited on Jul. 11, 2012, 4 pages.

Anonymous. (Mar. 2006-Nov. 2013). "Anacor Pharmaceuticals Scientific Presentations", 7 pages.

Archibald, J.L. et al. (1974). "Benzamidopiperidines. 2. Heterocyclic Compounds Related to Indoramin," *Journal of Medicinal Chemistry* 17(7):736-739.

Archibald, J.L. et al. (Sep. 1967). "New Reactions of Pyrroles. II. Preparation and Reactions of Pyrroleglyoxyloyl Derivatives," *Journal of Heterocyclic Chemistry* 4:335-338.

Battersby, A.R. et al. (1992, e-published Jan. 1, 1992). "Synthetic Studies Relevant to Biosynthetic Research on Vitamin B12. Part 10. Construction of the East and West Building Blocks for Synthesis of Isobacteriochlorins," *Journal of Chemical Society* 17:2175-2187.

Bentov, M. et al. (1964). "4-Fluoroindole and Derivatives," *Israel Journal of Chemistry* 2:25-28.

Birchall, G.R. et al. (1971). "The Chlorination of Pyrroles. Part II," *Canadian Journal of Chemistry* 49:919-922.

Black, D.S.C. et al. (1996). "Reaction of Some 4,6-Dimethoxyindoles with Oxalyl Chloride," *Tetrahedron* 52(26):8925-8936.

Black, D.S.C. et al. (1996). "The Indol-2-Ylglyoxylamide Moiety: A New Building Block for the Design and Self-Assembly of Hydrogen Bond Networks," *Journal of American Chemical Society* 118(34):8148-8149.

Black, D.S.C. et al. (2000). "Formation of C-Amido-Calix[3]Indoles from 2'- and 7'- Indolylglyoxylamides," *Tetrahedron* 56:8513-8524.

Bohusch, M. et al. (1991). "Consequences of a Diminution of the Porphyrin π-System: Attempted Syntheses of Bacteriophin and Chlorophin," *Liebigs Annalen der Chemie* 67-70. (Abstract Only).

Borthwick, A.D. et al. (Jan. 3, 2002, e-published Dec. 5, 2001). "Design and synthesis of Pyrrolidine-5,5-trans-Lactams (5-Oxohexandropyrrolo[3,2-b]Pyrroles) as Novel Mechanism-Based Inhibitors of Human Cytomegalovirus Protease. 2. Potency and Chirality," *Journal of Medicinal Chemistry* 45(1):1-18.

Cameron, B.D. et al. (1973). "The Synthesis and Metabolic Fate of $^{14}$C-Viminol, a New Analgesic, in the Rat and the Dog," *Arzneimittel-Forshung/Drug Res.* 23(5):708-712.

Cardellini, M. et al. (Feb. 1977). "Indolizine Derivatives with Biological Activity I: N'Substituted Hydrazides of Indolizine-2-Carboxylic Acid," *Journal of Pharmaceutical Sciences* 66(2):259-262.

CAS Registry No. 1002010-45-8, created Feb. 7, 2008, last accessed Oct. 30, 2013, 1 page.

CAS Registry No. 1002010-93-6, created Feb. 7, 2008, last accessed Oct. 30, 2013, 2 pages.

CAS Registry No. 1004172-59-1, created Feb. 18, 2008, last accessed Oct. 30, 2013, 1 page.

CAS Registry No. 1004425-72-2, created Feb. 19, 2008, last accessed Oct. 30, 2013, 1 page.

CAS Registry No. 1026853-99-5 created Jun. 9, 2008, last accessed Feb. 2, 2012, 1 page.

CAS Registry No. 1027826-94-3, created Jun. 9, 2008, last accessed Feb. 2, 2012, 1 page.

CAS Registry No. 1029775-76-5, created Jun. 22, 2008, last accessed Feb. 2, 2012, 2 pages.

CAS Registry No. 1056748-82-3, created Oct. 3, 2008, last accessed Feb. 2, 2012, 1 page.

(56) References Cited

OTHER PUBLICATIONS

CAS Registry No. 130761-64-7, created Nov. 30, 1990, last accessed Feb. 2, 2012, 1 page.
CAS Registry No. 130761-68-1, created Nov. 30, 1990, last accessed Feb. 2, 2012, 2 pages.
CAS Registry No. 145045-69-8, created Dec. 25, 1992, last accessed Feb. 2, 2012, 2 pages.
CAS Registry No. 15940-17-7, created Nov. 16, 1984, last accessed Feb. 2, 2012, 1 page.
CAS Registry No. 15940-18-8, created Nov. 16, 1984, last accessed Feb. 2, 2012, 1 page.
CAS Registry No. 15940-19-9, created Nov. 16, 1984, last accessed Feb. 2, 2012, 1 page.
CAS Registry No. 15940-20-2, created Nov. 16, 1984, last accessed Feb. 2, 2012, 2 pages.
CAS Registry No. 15940-21-3, created Nov. 16, 1984 last accessed Feb. 2, 2012, 1 page.
CAS Registry No. 15940-22-4, created Nov. 16, 1984, last accessed Feb. 2, 2012, 2 pages.
CAS Registry No. 15940-23-5, created Nov. 16, 1984, last accessed Feb. 2, 2012, 1 page.
CAS Registry No. 15940-24-6, created Nov. 16, 1984, last accessed Feb. 2, 2012, 2 pages.
CAS Registry No. 15940-25-7, created Nov. 16, 1984, last accessed Feb. 2, 2012, 1 page.
CAS Registry No. 171845-45-8, created Dec. 29, 1995, last accessed Feb. 2, 2012, 2 pages.
CAS Registry No. 171854-40-3, created Dec. 29, 1995, last accessed Feb. 2, 2012, 1 page.
CAS Registry No. 171854-41-4, created Dec. 29, 1995, last accessed Feb. 2, 2012, 2 pages.
CAS Registry No. 171854-42-5, created Dec. 29, 1995, last accessed Feb. 2, 2012, 2 pages.
CAS Registry No. 171854-43-6, created Dec. 29, 1995, last accessed Feb. 2, 2012, 2 pages.
CAS Registry No. 171854-46-9, created Dec. 29, 1995, last accessed Feb. 2, 2012, 1 page.
CAS Registry No. 171854-47-0, created Dec. 29, 1995, last accessed Feb. 2, 2012, 2 pages.
CAS Registry No. 17854-44-7, created Dec. 29, 1995, last accessed Feb. 2, 2012, 1 page.
CAS Registry No. 185030-21-1, created Jan. 15, 1997, last accessed Feb. 2, 2012, 1 page.
CAS Registry No. 208765-70-2, created Jul. 22, 1998, last accessed Feb. 2, 2012, 1 page.
CAS Registry No. 208765-71-3, created Jul. 22, 1998, last accessed Feb. 2, 2012, 1 page.
CAS Registry No. 208765-72-4, created Jul. 22, 1998, last accessed Feb. 2, 2012, 2 pages.
CAS Registry No. 208765-73-5, created Jul. 22, 1998, last accessed Feb. 2, 2012, 1 page.
CAS Registry No. 208765-74-6, created Jul. 22, 1998, last accessed Feb. 2, 2012, 1 page.
CAS Registry No. 208765-75-7, created Jul. 22, 1998, last accessed Feb. 2, 2012, 1 page.
CAS Registry No. 208765-76-8, created Jul. 22, 1998, last accessed Feb. 2, 2012, 1 page.
CAS Registry No. 208765-77-9, created Jul. 22, 1998, last accessed Feb. 2, 2012, 2 pages.
CAS Registry No. 208765-78-0, created Jul. 22, 1998, last accessed Feb. 2, 2012, 1 page.
CAS Registry No. 208765-79-1, created Jul. 22, 1998, last accessed Feb. 2, 2012, 2 pages.
CAS Registry No. 208765-80-4, created Jul. 22, 1998, last accessed Feb. 2, 2012, 1 page.
CAS Registry No. 208765-81-5, created Jul. 22, 1998, last accessed Feb. 2, 2012, 2 pages.
CAS Registry No. 208765-82-6, created Jul. 22, 1998, last accessed Feb. 2, 2012, 1 page.
CAS Registry No. 208765-83-7, created Jul. 22, 1998, last accessed Feb. 2, 2012, 2 pages.
CAS Registry No. 208765-84-8, created Jul. 22, 1998, last accessed Feb. 2, 2012, 1 page.
CAS Registry No. 208765-85-9, created Jul. 22, 1998, last accessed Feb. 2, 2012, 2 pages.
CAS Registry No. 208765-86-0, created Jul. 22, 1998, last accessed Feb. 2, 2012, 1 page.
CAS Registry No. 208765-87-1, created Jul. 22, 1998, last accessed Feb. 2, 2012, 2 pages.
CAS Registry No. 208765-88-2, created Jul. 22, 1998, last accessed Feb. 2, 2012, 1 page.
CAS Registry No. 208765-89-3, created Jul. 22, 1998, last accessed Feb. 2, 2012, 2 pages.
CAS Registry No. 208765-90-6, created Jul. 22, 1998, last accessed Feb. 2, 2012, 1 page.
CAS Registry No. 208765-91-7, created Jul. 22, 1998, last accessed Feb. 2, 2012, 1 page.
CAS Registry No. 208765-92-8, created Jul. 22, 1998, last accessed Feb. 2, 2012, 1 page.
CAS Registry No. 208765-93-9, created Jul. 22, 1998, last accessed Feb. 2, 2012, 1 page.
CAS Registry No. 208765-94-0, created Jul. 22, 1998, last accessed Feb. 2, 2012, 2 pages.
CAS Registry No. 208765-95-1, created Jul. 22, 1998, last accessed Feb. 2, 2012, 1 page.
CAS Registry No. 208765-96-2, created Jul. 22, 1998, last accessed Feb. 2, 2012, 2 pages.
CAS Registry No. 208766-03-4, created Jul. 22, 1998, last accessed Feb. 2, 2012, 1 page.
CAS Registry No. 208766-04-5, created Jul. 22, 1998, last accessed Feb. 2, 2012, 2 pages.
CAS Registry No. 208766-05-6, created Jul. 22, 1998, last accessed Feb. 2, 2012, 1 page.
CAS Registry No. 23502-48-9, created Nov. 16, 1984, last accessed Feb. 2, 2012, 2 pages.
CAS Registry No. 263554-36-5, created May 2, 2000, last accessed Feb. 2, 2012, 1 page.
CAS Registry No. 263554-39-8, created May 2, 2000, last accessed Feb. 2, 2012, 2 pages.
CAS Registry No. 26883-51-2, created Nov. 16, 1984, last accessed Feb. 2, 2012, 1 page.
CAS Registry No. 292063-96-8, created Oct. 2, 2000, last accessed Feb. 2, 2012, 1 page.
CAS Registry No. 292064-15-4, created Oct. 2, 2000, last accessed Feb. 2, 2012, 2 pages.
CAS Registry No. 31709-75-8, created Nov. 16, 1984, last accessed Feb. 2, 2012, 2 pages.
CAS Registry No. 31709-76-9, created Nov. 16, 1984, last accessed Feb. 2, 2012, 1 page.
CAS Registry No. 31709-77-0, created Nov. 16, 1984, last accessed Feb. 2, 2012, 1 page.
CAS Registry No. 31710-23-3, created Nov. 16, 1984, last accessed Feb. 2, 2012, 1 page.
CAS Registry No. 364044-26-8, created Oct. 23, 2001, last accessed Feb. 2, 2012, 1 page.
CAS Registry No. 364044-30-4, created Oct. 23, 2001, last accessed Feb. 2, 2012, 1 page.
CAS Registry No. 36793-47-2, created Nov. 16, 1984, last accessed Feb. 2, 2012, 2 pages.
CAS Registry No. 3758-62-1, created Nov. 16, 1984, last accessed Feb. 2, 2012, 1 page.
CAS Registry No. 3768-71-6, created Nov. 16, 1984, last accessed Feb. 2, 2012, 1 page.
CAS Registry No. 3768-72-7, created Nov. 16, 1984, last accessed Feb. 2, 2012, 1 page.
CAS Registry No. 3768-82-9, created Nov. 16, 1984, last accessed Feb. 2, 2012, 2 pages.
CAS Registry No. 396733-55-4, created Feb. 28, 2002, last accessed Feb. 2, 2012, 1 page.
CAS Registry No. 41596-37-6, created Nov. 16, 1984, last accessed Feb. 2, 2012, 1 page.

(56) References Cited

OTHER PUBLICATIONS

CAS Registry No. 42060-03-7, created Nov. 16, 1984, last accessed Feb. 2, 2012, 2 pages.
CAS Registry No. 42060-05-9, created Nov. 16, 1984, last accessed Feb. 2, 2012, 1 page.
CAS Registry No. 42221-74-9, created Nov. 16, 1984, last accessed Feb. 2, 2012, 2 pages.
CAS Registry No. 422507-64-0, created May 29, 2002, last accessed Feb. 2, 2012, 1 page.
CAS Registry No. 422507-66-2, created May 29, 2002, last accessed Feb. 2, 2012, 1 page.
CAS Registry No. 422507-69-5, created May 29, 2002, last accessed Feb. 2, 2012, 1 page.
CAS Registry No. 43084-49-7, created Nov. 16, 1984, last accessed Feb. 2, 2012, 1 page.
CAS Registry No. 4380-46-5, created Nov. 16, 1984, last accessed Feb. 2, 2012, 1 page.
CAS Registry No. 4595-83-9, created Nov. 16, 1984, last accessed Feb. 2, 2012, 2 pages.
CAS Registry No. 477709-20-9, created Dec. 27, 2002, last accessed Feb. 2, 2012, 2 pages.
CAS Registry No. 477709-21-0, created Dec. 27, 2002 last accessed Feb. 2, 2012, 2 pages.
CAS Registry No. 477709-22-1, created Dec. 27, 2002, last accessed Feb. 2, 2012, 1 page.
CAS Registry No. 477709-24-3, created Dec. 27, 2002, last accessed Feb. 2, 2012, 2 pages.
CAS Registry No. 477709-25-4, created Dec. 27, 2002, last accessed Feb. 2, 2012, 1 page.
CAS Registry No. 477709-26-5, created Dec. 27, 2002, last accessed Feb. 2, 2012, 2 pages.
CAS Registry No. 477709-27-6, created Dec. 27, 2002, last accessed Feb. 2, 2012, 1 page.
CAS Registry No. 477709-28-7, created Dec. 27, 2002, last accessed Feb. 2, 2012, 2 pages.
CAS Registry No. 477709-29-8, created Dec. 27, 2002, last accessed Feb. 2, 2012, 1 page.
CAS Registry No. 477709-30-1 created Dec. 27, 2002, last accessed Feb. 2, 2012, 2 pages.
CAS Registry No. 477857-72-0, created Dec. 31, 2002, last accessed Feb. 2, 2012, 1 page.
CAS Registry No. 477857-73-1, created Dec. 31, 2002, last accessed Feb. 2, 2012, 2 pages.
CAS Registry No. 477857-74-2, created Dec. 31, 2002, last accessed Feb. 2, 2012, 1 page.
CAS Registry No. 477857-75-3, created Dec. 31, 2002, last accessed Feb. 2, 2012, 2 pages.
CAS Registry No. 477857-76-4, created Dec. 31, 2002, last accessed Feb. 2, 2012, 1 page.
CAS Registry No. 477857-77-5, created Dec. 31, 2002, last accessed Feb. 2, 2012, 2 pages.
CAS Registry No. 477857-78-6, created Dec. 31, 2002, last accessed Feb. 2, 2012, 1 page.
CAS Registry No. 477857-79-7, created Dec. 31, 2002, last accessed Feb. 2, 2012, 2 pages.
CAS Registry No. 477857-80-0, created Dec. 31, 2002, last accessed Feb. 2, 2012, 1 page.
CAS Registry No. 477857-81-1, created Dec. 31, 2002, last accessed Feb. 2, 2012, 2 pages.
CAS Registry No. 477863-31-3, created Dec. 31, 2002, last accessed Feb. 2, 2012, 1 page.
CAS Registry No. 477863-34-6, created Dec. 31, 2002, last accessed Feb. 2, 2012, 2 pages.
CAS Registry No. 477863-37-9, created Dec. 31, 2002, last accessed Feb. 2, 2012, 1 page.
CAS Registry No. 477871-94-6, created Dec. 31, 2002, last accessed Feb. 2, 2012, 2 pages.
CAS Registry No. 477871-95-7, created Dec. 31, 2002, last accessed Feb. 2, 2012, 1 page.
CAS Registry No. 477871-96-8, created Dec. 31, 2002, last accessed Feb. 2, 2012, 1 page.
CAS Registry No. 477871-97-9, created Dec. 31, 2002, last accessed Feb. 2, 2012, 1 page.
CAS Registry No. 477871-98-0, created Dec. 31, 2002, last accessed Feb. 2, 2012, 1 page.
CAS Registry No. 477871-99-,1 created Dec. 31, 2002, last accessed Feb. 2, 2012, 2 pages.
CAS Registry No. 477872-00-7, created Dec. 31, 2002, last accessed Feb. 2, 2012, 1 page.
CAS Registry No. 477872-01-8, created Dec. 31, 2002, last accessed Feb. 2, 2012, 2 pages.
CAS Registry No. 477872-02-9, created Dec. 31, 2002, last accessed Feb. 2, 2012, 1 page.
CAS Registry No. 477872-03-0, created Dec. 31, 2002, last accessed Feb. 2, 2012, 1 page.
CAS Registry No. 477872-04-1, created Dec. 31, 2002, last accessed Feb. 2, 2012, 2 pages.
CAS Registry No. 477872-05-2, created Dec. 31, 2002, last accessed Feb. 2, 2012, 1 page.
CAS Registry No. 477872-69-8, created Dec. 31, 2002, last accessed Feb. 2, 2012, 2 pages.
CAS Registry No. 477872-70-1, created Dec. 31, 2002, last accessed Feb. 2, 2012, 1 page.
CAS Registry No. 477872-71-2, created Dec. 31, 2002, last accessed Feb. 2, 2012, 2 pages.
CAS Registry No. 477872-72-3, created Dec. 31, 2002, last accessed Feb. 2, 2012, 1 page.
CAS Registry No. 477872-73-4 created Dec. 31, 2002, last accessed Feb. 2, 2012, 2 pages.
CAS Registry No. 477872-74-5, created Dec. 31, 2002, last accessed Feb. 2, 2012, 1 page.
CAS Registry No. 477872-75-6, created Dec. 31, 2002, last accessed Feb. 2, 2012, 2 pages.
CAS Registry No. 477872-76-7, created Dec. 31, 2002, last accessed Feb. 2, 2012, 1 page.
CAS Registry No. 477872-77-8, created Dec. 31, 2002, last accessed Feb. 2, 2012, 1 page.
CAS Registry No. 477872-78-9, created Dec. 31, 2002, last accessed Feb. 2, 2012, 2 pages.
CAS Registry No. 477872-79-0, created Dec. 31, 2002, last accessed Feb. 2, 2012, 1 page.
CAS Registry No. 477872-80-3, created Dec. 31, 2002, last accessed Feb. 2, 2012, 2 pages.
CAS Registry No. 485843-91-2, created Feb. 5, 2003, last accessed Feb. 2, 2012, 1 page.
CAS Registry No. 485843-92-3, created Feb. 5, 2003, last accessed Feb. 2, 2012, 1 page.
CAS Registry No. 53391-28-9, created Nov. 16, 1984, last accessed Feb. 2, 2012, 2 pages.
CAS Registry No. 53391-29-0, created Nov. 16, 1984, last accessed Feb. 2, 2012, 1 page.
CAS Registry No. 53391-30-3, created Nov. 16, 1984, last accessed Feb. 2, 2012, 2 pages.
CAS Registry No. 53391-52-9, created Nov. 16, 1984, last accessed Feb. 2, 2012, 1 page.
CAS Registry No. 53391-63-2, created Nov. 16, 1984, last accessed Feb. 2, 2012, 2 pages.
CAS Registry No. 65473-58-7, created Nov. 16, 1984, last accessed Feb. 2, 2012, 1 page.
CAS Registry No. 655223-84-0, created Feb. 27, 2004, last accessed Feb. 2, 2012, 1 page.
CAS Registry No. 655223-85-1, created Feb. 27, 2004 last accessed Feb. 2, 2012, 2 pages.
CAS Registry No. 6616-51-9, created Nov. 16, 1984, last accessed Feb. 2, 2012, 1 page.
CAS Registry No. 68803-72-5, created Nov. 16, 1984, last accessed Feb. 2, 2012, 2 pages.
CAS Registry No. 773098-60-5, created Nov. 1, 2004, last accessed Feb. 2, 2012, 1 page.
CAS Registry No. 773098-61-6, created Nov. 1, 2004, last accessed Feb. 2, 2012, 2 pages.

(56) References Cited

OTHER PUBLICATIONS

CAS Registry No. 802313-56-0, created Dec. 25, 2004, last accessed Feb. 2, 2012, 1 page.
CAS Registry No. 81729-69-3, created Nov. 16, 1984, last accessed Feb. 2, 2012, 1 page.
CAS Registry No. 81741-58-4, created Nov. 16, 1984, last accessed Feb. 2, 2012, 1 page.
CAS Registry No. 83996-64-9, created Nov. 16, 1984, last accessed Feb. 2, 2012, 1 page.
CAS Registry No. 860610-36-2, created Aug. 17, 2005, last accessed Feb. 2, 2012, 1 page.
CAS Registry No. 860610-37-3, created Aug. 17, 2005, last accessed Feb. 2, 2012, 1 page.
CAS Registry No. 860649-79-2, created Aug. 17, 2005, last accessed Feb. 2, 2012, 1 page.
CAS Registry No. 860649-80-5, created Aug. 17, 2005, last accessed Feb. 2, 2012, 1 page.
CAS Registry No. 866010-45-9, created Oct. 25, 2005, last accessed Feb. 2, 2012, 1 page.
CAS Registry No. 866010-46-0, created Oct. 25, 2005, last accessed Feb. 2, 2012, 2 pages.
CAS Registry No. 866010-47-1, created Oct. 25, 2005, last accessed Feb. 2, 2012, 1 page.
CAS Registry No. 866010-76-6, created Oct. 25, 2005, last accessed Feb. 2, 2012, 2 pages.
CAS Registry No. 866010-82-4, created Oct. 25, 2005, last accessed Feb. 2, 2012, 1 page.
CAS Registry No. 866010-83-5, created Oct. 25, 2005, last accessed Feb. 2, 2012, 2 pages.
CAS Registry No. 866010-85-7, created Oct. 25, 2005, last accessed Feb. 2, 2012, 1 page.
CAS Registry No. 866042-95-7, created Oct. 25, 2005, last accessed Feb. 2, 2012, 1 page.
CAS Registry No. 866042-98-0, created Oct. 25, 2005, last accessed Feb. 2, 2012, 1 page.
CAS Registry No. 866042-99-1, created Oct. 25, 2005, last accessed Feb. 2, 2012, 1 page.
CAS Registry No. 866043-03-0, created Oct. 25, 2005, last accessed Feb. 2, 2012, 2 pages.
CAS Registry No. 866043-06-3, created Oct. 25, 2005, last accessed Feb. 2, 2012, 1 page.
CAS Registry No. 945220-52-0, created Aug. 21, 2007, last accessed Feb. 2, 2012, 1 page.
CDC. (Nov. 16, 2015). "Aspergillosis Risk and Prevention," located at http://>www.cdc.fungal/diseases/aspergillosis/risk-prevention.html< 3 pages.
CDC. (Nov. 16, 2015). "Fungal Diseases," located at http://>www.cdc.fungal/diseases/aspergillosis/risk-prevention.html< 2 pages.
CHEMCATS. (Feb. 13, 2008). "1H-Pyrrole-2-Acetamide, N-(4-Bromophenyl)-1-(2-Chloro-4-Nitrophenyl)-☐-Oxo-," *Ambinter Stock Screening Collection* 5 pages.
CHEMCATS. (Feb. 18, 2008). "1 H-Pyrrole-2-Acetamide, N-(2,4-Dichlorophenyl)-1-Methyl-alpha-Oxo-," *Interchim Intermediates* 5 pages.
CHEMCATS. (Jan. 25, 2008). "Benzo [b] Thiophene-2-Carboxylic Acid, 3-[2- [[(4-Methoxyphenyl) Amino]Oxoacetyl]-1H-Pyrrol-1-yl]-, Methyl Ester," *Ryan Scientific Screening Library* 5 pages.
Chiarino, D. et al. (1978). "Stereochemistry of Viminol, a Novel Central Analgesic," *Arzneimittel-Forshung/Drug Res.* 28(11):1554-1561.
Cook, A.H. et al. (1949, e-published Jan. 1, 1949). "Studies in the Azole Series. Part XXIV. The Interaction of Carbonyl Compounds and 2-Thio-5-Thiazolidone," *Journal of Chemical Society* 633:3007-3012.
Crowley, K.J. et al. (1957). "Intermediates for the Synthesis of Optically Active Methyl-Substituted Long-Chain Acids. Part II," *Journal of the Chemical Society* 2931-2934.
Dannhardt, G. et al. (1979). "Synthese und Eigenschaften von 2,3-Dihydro-1H-Pyrrolizinen," *Arch. Pharm.* 312:896-907.

Dannhardt, G. et al. (1994). "Nonsteroidal Antiinflammatory Agents, XVIII: C-5 Functionalized 6,7-Diphenyl-2,3-Dihydro-1H-Pyrrolizines as Inhibitors of Bovine Cyclooxygenase and 5-Lipoxygenase," *Arch Pharm* 327:509-514.
Dannhardt, V.G. et al. (1986). "Antiphlogistische 2,3-Dihydro-1H-Pyrrolizine, 11. Mitt. Dihydropyrrolizinyl-Substituierte 2-Aminoethanol-und Glykosäure-Derivate," *Chemiker-Zeitung* 110(3):124-127.
Dumoulin, H. et al. (1998). "2-Oxo-2-(Pehn-2-Ylpyrrol-2-Yl)Acetamides as Potential Anxiolytic Agents: Synthesis and Affinity at the Central Benzodiazepine Receptor," *European Journal of Medicinal Chemistry* 33:201-207.
Dyke, S.F. et al. (1978). "Pavinane and Isopavinane Alkaloids," *Tetrahedron* 34:241-245.
Ertl, P. et al. (2000). "Fast Calculation of Molecular Polar Surface Area as a Sum of Fragment-Based Contributions and Its Application to the Prediction of Drug Transport Properties," *Journal of Medicinal Chemistry* 43(20):3714-3717.
Fryer, R.I. et al. (Dec. 1967). "Quinazolines and 1,4-Benzodiazepines. XXXVII. Synthesis and Rearrangements of a Substituted 5-Phenyl-1H-1,4-Benzodiazepine," *Journal of Organic Chemistry* 32:3798-3803.
Galbraith, A. et al. (Jan. 20, 1961). "The Formation of Cycl[3,2,2]azine Derivatives via the Reaction of Pyrrocoline with Dimethyl Acetylenedicarboxylate," *Journal of the American Chemical Society* 83:453-458.
Groll, A.H. et al. (1996). "Trends in the Postmortem Epidemiology of Invasive Fungal Infections at a University Hospital," *Journal of Infection* 33:23-32.
Hagishita, S. et al. (1996). "Potent Inhibitors of Secretory Phospholipase A2: Synthesis and Inhibitory Activities of Indolizine and Indene Derivatives," *Journal of Medicinal Chemistry* 39(19):3636-3658.
Hudack, R.A. et al. (2006, e-published Jan. 14, 2006). "Design, Synthesis, and Biological Activity of Novel Polycyclic Aza-Amide FKBP12 Ligands," *Journal of Medicinal Chemistry* 49(3):1202-1206.
Ignatovich, J. et al. (2008). "Synthesis of Functionalized Benzyl Amines by the Reductive Alkylation of Heterocyclic and Heteroaromatic Amines with Arylaldehydes and preparation of the Intermediates for New Synthetic Biomolecules," *ARKAT-USA, Inc.* (ix):42-51.
Islam, I. et al. (2007, e-published Apr. 27, 2007). "Indolinone Based Phosphoinositide-Dependent Kinase-1 (PDK1) Inhibitors. Part 1: Design, Synthesis and Biological Activity," *Bioorganic & Medicinal Chemistry Letters* 17:3814-3818.
Keawin, T. et al. (2005, e-published Dec. 10, 2004). "Reaction of Some 4,6-Dimethoxyindoles with Nitric Acid: Nitration and Oxidative Dimerisation," *Tetrahedron* 61:853-861.
Leo, A. et al. (Dec. 1971). "Partition Coefficients and Their Uses," *Chemical Reviews* 71(6):525-616.
Mahiout, Z. et al. (2008, e-published Feb. 28, 2008). "Solvent-Dependent Oxidations of 5-and 6-Azaindoles to Trioxopyrrolopyridines and Functionalised Azaindoles," *Organic & Biomolecular Chemistry* 6:1364-1376.
Mao, W. et al. (Date Unknown) "AN2718 Has Broad Spectrum Antifungal Activity Necessary for the Topical Treatment of Skin and Nail Fungal Infections," P2422, 7 pages.
McDonell et al. (Jan. 1999). "Antiseptics and Disinfectants: Activity, Action, and Resistance", *Clinical Microbiology Reviews* 12(1):147-179.
Nourmohammadian, F. et al. (2005, e-published Jan. 21, 2005). "An AB Initio Molecular Orbital Study of Structural Isomers of Diketopyrrolopyrrole," *Dyes and Pigments* 67:15-20.
Pätzel, M. et al. (2005). "Product Class 5: ☐-Heteroatom-Substituted Alkanamides," *Science of Synthesis* 21:477-535.
Plattner, J.J. et al. (Date Unknown). "Medicinal Chemistry of AN2690, A Novel Broad-Spectrum Antifungal Agent in Development for the Topical Treatment of Onychomycosis," Poster #775, Anacor Pharmaceuticals, 1 page.
Ribaud, P. et al. (Feb. 1999). "Survival and Prognostic Factors of Invasive Aspergillosis After Allogeneic Bone Marrow Transplantation," *Clinical Infectious Diseases* 28:322-330.
Rowe, F.M. et al. (1935, e-published Jan. 1, 1935). "A Reaction of Certain Diazosulphonates Derived from β-Naphthol-1-Sulphonic

(56) References Cited

OTHER PUBLICATIONS

Acid. Part XIII. Fission of the Naphthalene Nucleus and Subsequent Closure in Two Directions," *Journal of Chemical Society* 420:1796-1808.

Rowe, F.M. et al. (1936, e-published Jan. 1, 1936). "A Reaction of Certain Diazosulphonates Derived from β-Naphthol-1-Sulphonic Acid. Part XV. Derivatives of 2'-Nitro-4'-Methyl-Benzene-2-Naphthol-1-Diazosulphonate and Synthesis of 2-(2'-Nitro-4'-Methylphenylamino)Isoindolinone-3-Acetic Acid," *Journal of Chemical Society* 232:1098-1108.

Roy, K. et al. (Dec. 2008). "Development of Linear and Nonlinear Predictive QSAR Models and Their External Validation Using Molecular Similarity Principle for Anti-HIV Indolyl Aryl Sulfones," *Journal of Enzyme Inhibition and Medicinal Chemistry* 23(6):980-995.

Savage, S.A. et al. (1998). "Efficient Synthesis of 4-, 5-, and 6-Methyl-2,2'-Bipyridine by a Negishi Cross-Coupling Strategy Followed by High-Yield Conversion to Bromo- and Chloromethyl-2,2'-Bipyridines," *Journal of Organic Chemistry* 63(26):10048-10051.

Schoichet Laboratory at UCSF (through Zinc database of commercially available small molecules—entered to CHEMCATS Feb. and Mar. 2008; p. 1-64.

Scott, M.K. et al. (1995). "Piperazinylalkyl Heterocycles as Potential Antipsychotic Agents," *Journal of Medicinal Chemistry* 38(21):4198-4210.

Si, Z. et al. (Apr. 6, 2004). "Small-Molecule Inhibitors of HIV-1 Entry Block Receptor-Induced Conformational Changes in the Viral Envelope Glycoproteins," *Proceedings of the National Academy of Sciences* 101(14):5036-5041.

Slassi, A. et al. (2000). "5-Alkyltryptamine Derivatives as Highly Selective and Potent 5-HT$_{1D}$ Receptor Agonists," *Bioorganic & Medicinal Chemistry Letters* 10:1707-1709.

Sofan, M.A. et al. (2004). "Studies on 2,3-Dioxopyrrolidines. Synthesis of Piperazine, Pyrrolo[4,5-b]Indole, Pyrazino [5,6-b]Indole and Arylazo Derivatives of Amino Acids," *Polish Journal of Chemistry* 78:837-842.

Troxler, F. et al. (1968). "Beiträge zur Chemie der Pyrrolo[3,2-c]Azepine und der Pyrrole[3,2-b]Azepine)," *Helvetica Chimica Acta* 51(8):1870-188, English Summary Only.

Vecchietti, V. et al. (Jan.-Feb. 1974). "Nitro-Pyrrole Derivatives with Antimicrobial Activity," *European Journal of Medicinal Chemistry* 9(1):76-80.

Venturella, V.S. (Oct. 1964). "Arylindolizines III. Methoxyl and Glyoxyl Derivatives of Several Substituted Phenylindolizines," *Journal of Pharmaceutical Sciences* 53(10):1166-1169.

Wahyuningsih, T.D. et al. (2007, e-published May 3, 2007). "Synthesis of Indolo[2,3-c]Quinolines From 3-Arylindole-2-Ketoximes," *Tetrahedron* 63:6713-6719.

Yang, Z. et al. (2002). "A Strategy for the Synthesis of Aryl ☐-Ketoamides Based Upon the Acylation of Anions Derived from Cyanomethylamines Followed by Oxidative Cleavage," *Organic Letters* 4(7):1103-1105.

Yavari, I. et al. (2001). "Efficient Synthesis of 5,6,7-Trisubstituted 1H-Pyrrolizines," *Tetrahedron* 57:5873-5878.

Yavari, I. et al. (2002). "A Simple Synthesis of Stable Heterocyclic Phosphorus Ylides Derived from NH-Acids," *Phosphorus, Sulfur and Silicon* 177:545-553.

Nowaczyk, A. et al. (2008). "Triazole Derivatives With Antifungal Activity: A Poloniae Pharmacophore Model Study," *Acta Pharmaceutica—Drug Research* 65(6):795-798.

\* cited by examiner

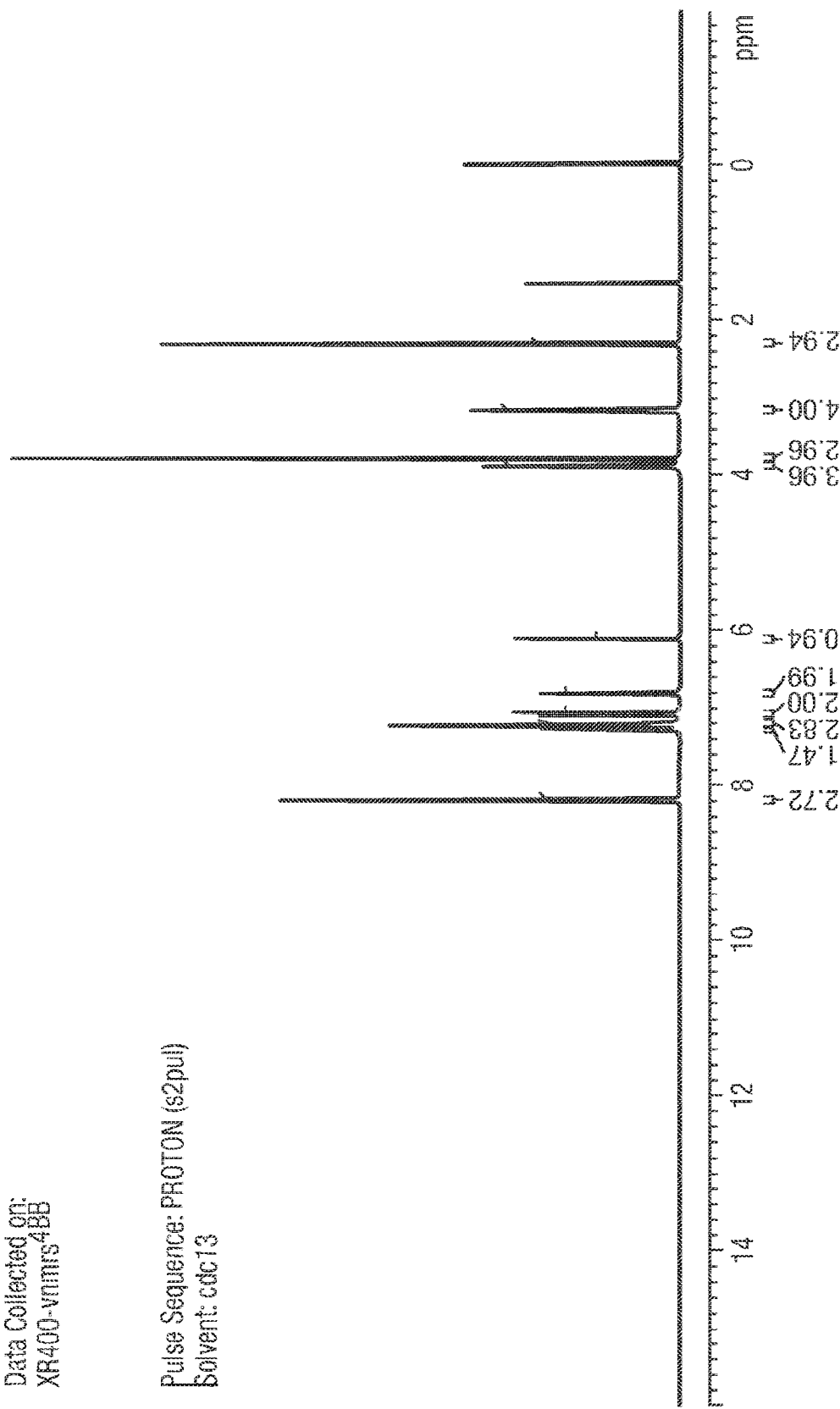

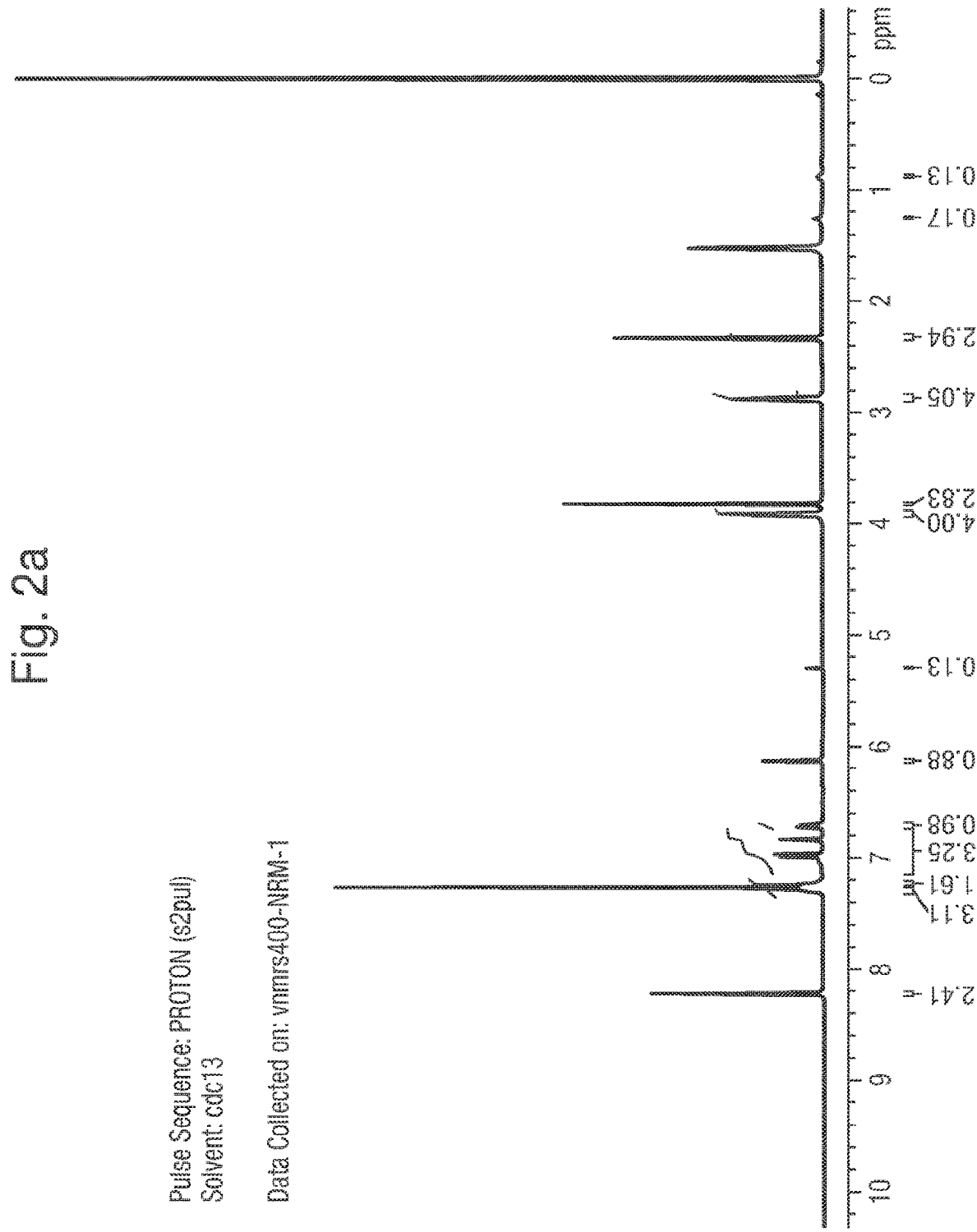

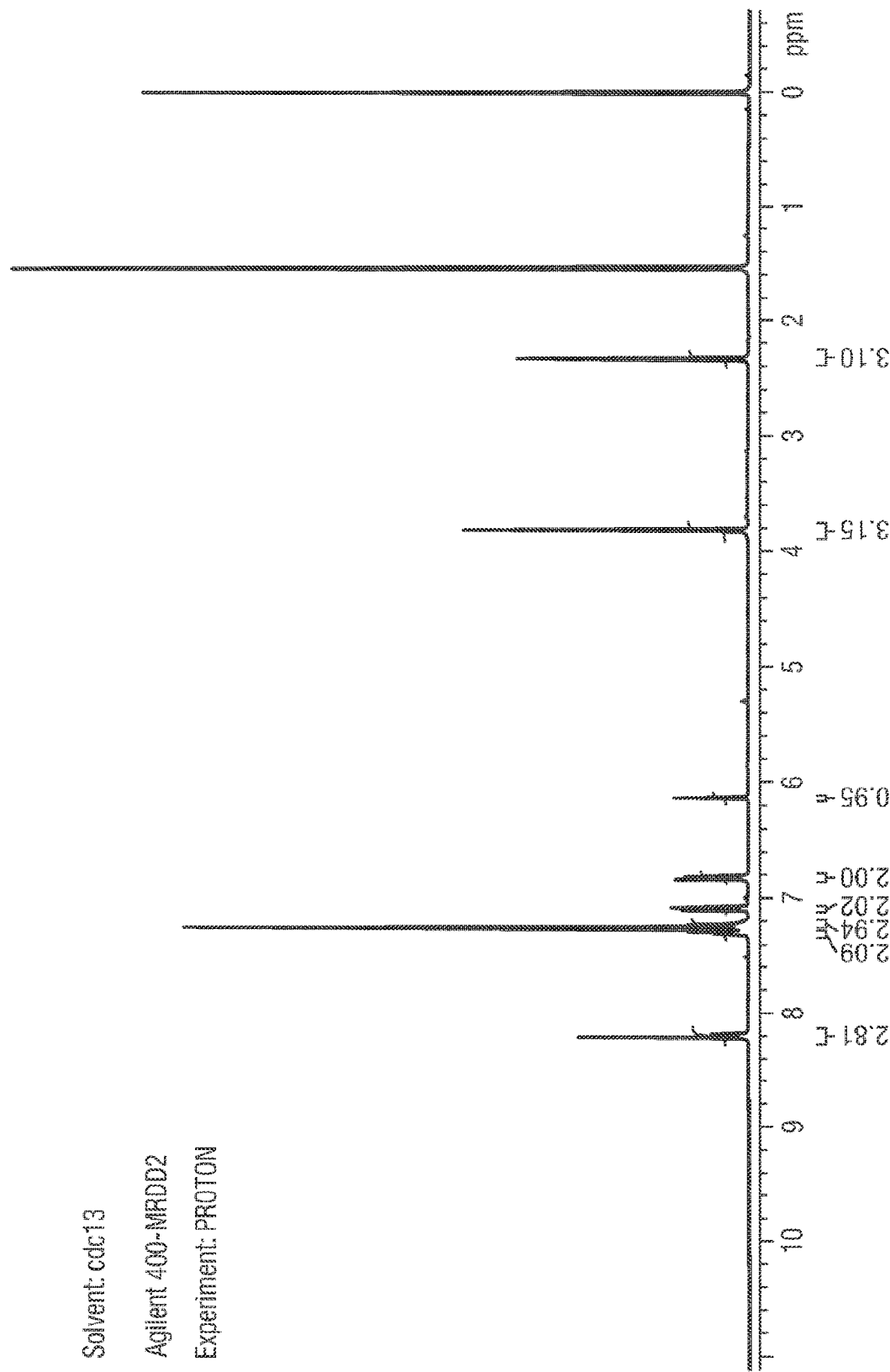

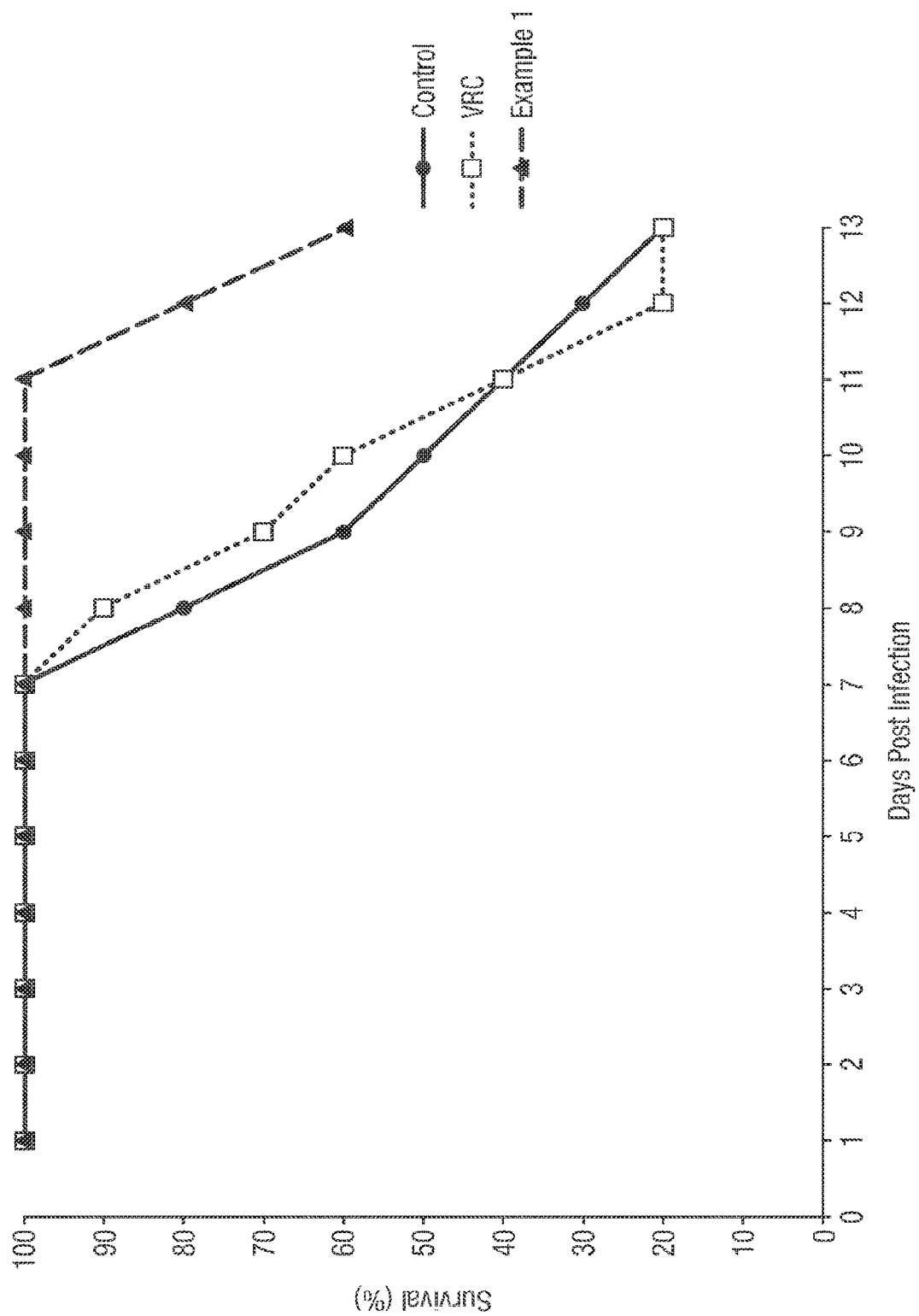

ANTIFUNGAL AGENTS

CROSS-REFERENCE TO RELATED APPLICATIONS

This application is a continuation of U.S. patent application Ser. No. 15/528,457, which adopts the international filing date of Nov. 20, 2015, which is the U.S. National Phase Application under 35 U.S.C. § 371 of International Application No. PCT/GB2015/053546, filed on Nov. 20, 2015, which claims priority benefit of British Patent Application No. 1420743.5, filed on Nov. 21, 2014, and British Patent Application No. 1505891.0, filed on Apr. 7, 2015, the disclosures of each of which are hereby incorporated by reference in their entireties.

FIELD OF THE INVENTION

This invention relates to pyrrole compounds, combinations and compositions comprising a pyrrole compound and a further antifungal agent, and their therapeutic use in prevention or treatment of fungal diseases. It also relates to the use of the compound, combinations and compositions as agricultural fungicides.

BACKGROUND OF THE INVENTION

Invasive fungal infections are well recognised as diseases of the immunocompromised host. Over the last twenty years there have been significant rises in the number of recorded instances of fungal infection. In part this is due to increased awareness and improved diagnosis of fungal infection. However, the primary cause of this increased incidence is the vast rise in the number of susceptible individuals. This is due to a number of factors including new and aggressive immunosuppressive therapies, increased survival in intensive care, increased numbers of transplant procedures and the greater use of antibiotics worldwide.

In certain patient groups, fungal infection occurs at high frequency; lung transplant recipients have a frequency of up to 20% colonisation and infection with a fungal organism and fungal infection in allogenic haemopoetic stem cell transplant recipients is as high as 15% (Ribaud et al., 1999, Clin Infect Dis. 28:322-30).

Recently there has been increased awareness of the contribution of fungal sensitisation, colonisation, allergy and localised infection in the exacerbation of existing respiratory diseases. Here fungi have been implicated in asthma, COPD, brochiectasis and cystic fibrosis. Allergic bronchopulmonary aspergillosis (ABPA) is a lower respiratory tract condition caused by fungal colonisation, typically by *Aspergillus fumigatus*. ABPA can be seen is asthmatics at a rate of 0.7-3.5% and cystic fibrosis at a rate of 7-9%.

Currently there are four classes of antifungal drug are available to treat systemic fungal infections. These are the polyenes (e.g., amphotericin B), the azoles (e.g., ketoconazole or itraconazole), the echinocandins (e.g., caspofungin) and flucytosine.

The polyenes are the oldest class of antifungal agent being first introduced in the 1950's. The exact mode of action remains unclear but polyenes are only effective against organisms that contain sterols in their outer membranes. It has been proposed that amphotericin B interacts with membrane sterols to produce pores allowing leakage of cytoplasmic components and subsequent cell death.

Azoles work by inhibition of the 14α-demethylase via a cytochrome P450-dependent mechanism. This leads to a depletion of the membrane sterol ergosterol and the accumulation of sterol precursors resulting in a plasma membrane with altered fluidity and structure.

Echinocandins work by the inhibition of the cell wall synthetic enzyme 1-glucan synthase. This leads to abnormal cell wall formation, osmotic sensitivity and cell lysis.

Flucytosine is a pyrimidine analogue interfering with cellular pyrimidine metabolism as well DNA, RNA and protein synthesis. However widespread resistance to flucyotosine limits its therapeutic use.

It can be seen that to date the currently available antifungal agents act primarily against only two cellular targets; membrane sterols (polyenes and azoles) and 1-glucan synthase (echinocandins).

Resistance to both azoles and polyenes has been widely reported leaving only the recently introduced echinocandins to combat invasive fungal infections. As the use of echinocandins increases, resistance by fungi will inevitably occur.

The identification of new classes of antifungal agent is required to give the promise of positive therapeutic outcomes to patients.

Pyrrole compounds have also been identified as antifungal agents. WO 2009 130481 discloses pyrrole compounds that may be used in the prevention or treatment of fungal disease.

SUMMARY OF THE INVENTION

The present inventors have found that the pyrrole compound 2-(1,5-dimethyl-3-phenyl-1H-pyrrol-2-yl)-N-(4-(4-(5-fluoropyrimidin-2-yl)piperazin-1-yl)phenyl)-2-oxoacetamide is a particularly effective antifungal agent. It shows high potency in enzyme inhibition and fungal inhibition tests and has good bioavailability and low toxicity. Tests have shown that this pyrrole compound inhibits the growth of a wide variety of fungi, in particular the human pathogenic fungi *Aspergillus*. This particular compound has been shown to have activity against a wider spectrum of species within the *Aspergillus* genus than other, previously known, pyrrole compounds. Further, the compound has been shown to exhibit increased in vivo efficacy when compared to the known antifungal drug Voriconazole, in particular improved efficacy against *Scedosporium* fungi. The compound -(1,5-dimethyl-3-phenyl-1H-pyrrol-2-yl)-N-(4-(4-(5-fluoropyrimidin-2-yl)piperazin-1-yl)phenyl)-2-oxoacetamide may, therefore, be used to effectively treat a wide variety of fungal infection and disease.

It has also been found that 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide also exhibits good activity. The addition of a hydroxyl on the phenyl adjacent to the piperazinyl group aids solubility and permeability.

Deuterated derivates of 2-(1,5-dimethyl-3-phenyl-1H-pyrrol-2-yl)-N-(4-(4-(5-fluoropyrimidin-2-yl)piperazin-1-yl)phenyl)-2-oxoacetamide and 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide have also been found to be highly active.

Accordingly, the present invention provides a compound, which compound is:
(a)  2-(1,5-dimethyl-3-phenyl-1H-pyrrol-2-yl)-N-(4-(4-(5-fluoropyrimidin-2-yl)piperazin-1-yl)phenyl)-2-oxoacetamide or a deuterated derivative thereof, or
(b)  2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide or a deuterated derivative thereof, or (c) a prodrug of (a) or (b), or a pharmaceutically acceptable salt or agriculturally acceptable salt of (a), (b) or (c).

In one instance the compound is a pharmaceutical compound, which pharmaceutical compound is:
(a) 2-(1,5-dimethyl-3-phenyl-1H-pyrrol-2-yl)-N-(4-(4-(5-fluoropyrimidin-2-yl)piperazin-1-yl)phenyl)-2-oxoacetamide or a deuterated derivative thereof, or
(b) 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide or a deuterated derivative thereof, or
(c) a prodrug of (a) or (b), or
a pharmaceutically acceptable salt of (a), (b) or (c).

In another instance, the compound is an agricultural compound, which agricultural compound is:
(a) 2-(1,5-dimethyl-3-phenyl-1H-pyrrol-2-yl)-N-(4-(4-(5-fluoropyrimidin-2-yl)piperazin-1-yl)phenyl)-2-oxoacetamide, or
(b) 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide, or
an agriculturally acceptable salt of (a) or (b).

In another instance, the compound is: 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt or agriculturally acceptable salt thereof.

The present invention also provides a pharmaceutical composition comprising a pharmaceutical compound of the invention together with one or more pharmaceutically acceptable carriers and/or excipients.

Also provided is an agricultural composition comprising:
(a) 2-(1,5-dimethyl-3-phenyl-1H-pyrrol-2-yl)-N-(4-(4-(5-fluoropyrimidin-2-yl)piperazin-1-yl)phenyl)-2-oxoacetamide or an agriculturally acceptable salt thereof; or (b) 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide or an agriculturally acceptable salt thereof. Typically, the agricultural composition also comprises one or more agriculturally acceptable carriers and/or diluents.

In another aspect, the invention provides a pharmaceutical combination comprising: (i) a pharmaceutical compound of the invention; and (ii) a second antifungal agent.

In yet another aspect, the invention provides a pharmaceutical compound of the invention, a composition as defined above or a combination as defined above for use in a method of treatment of the human or animal body by therapy.

The invention also provides a pharmaceutical compound of the invention, a composition as defined above or a combination as defined above for use in the prevention or treatment of fungal disease.

In another aspect, the invention provides a kit comprising, in admixture or in separate containers, a pharmaceutical compound of the invention and a second antifungal agent. The kit typically comprises instructions for administration of the pharmaceutical compound and the second antifungal agent.

Also provided by the invention is a method of controlling a fungal disease in a plant, which method comprises applying to the locus of the plant a compound which is: 2-(1,5-dimethyl-3-phenyl-1H-pyrrol-2-yl)-N-(4-(4-(5-fluoropyrimidin-2-yl)piperazin-1-yl)phenyl)-2-oxoacetamide or an agriculturally acceptable salt thereof, or 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide or an agriculturally acceptable salt thereof; and optionally a second antifungal agent.

The invention also provides the use of a compound, which compound is: 2-(1,5-dimethyl-3-phenyl-1H-pyrrol-2-yl)-N-(4-(4-(5-fluoropyrimidin-2-yl)piperazin-1-yl)phenyl)-2-oxoacetamide or an agriculturally acceptable salt thereof, or 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide or an agriculturally acceptable salt thereof; optionally together with a second antifungal agent, as an agricultural fungicide.

In another aspect, the invention provides a method of preventing or treating fungal disease in a subject which method comprises administering to said subject an effective amount of a pharmaceutical compound of the invention, a composition as defined above or a combination as defined above.

In yet another aspect, the invention provides the use of a pharmaceutical compound of the invention, a composition as defined above or a combination as defined above in the manufacture of a medicament for the prevention or treatment of fungal disease.

BRIEF DESCRIPTION OF THE FIGURES

FIG. 1 provides NMR data for 2-(1, 5-Dimethyl-3-phenyl-1H-pyrro-2-yl)-N-{4-[4-(5-fluoro-pyrimidin-2-yl)-piperazin-1-yl]-phenyl}-2-oxo-acetamide ($^1$H NMR (400 MHz, CDCl$_3$)).

FIG. 2a provides NMR data for 2-(1,5-Dimethyl-3-phenyl-1H-pyrrol-2-yl)-N-(4-(4-(5-fluoropyrimidin-2-yl)piperazin-1-yl)-3-hydroxyphenyl)-2-oxoacetamide ($^1$H NMR (400 MHz, CDCl$_3$)).

FIG. 3 provides NMR data for 2-(1,5-dimethyl-3-phenyl-1H-pyrrol-2-yl)-N-(4-(4-(5-fluoropyrimidin-2-yl)piperazin-1-yl-2,2,3,3,5,5,6,6-d$_8$)phenyl)-2-oxoacetamide ($^1$H NMR (400 MHz, CDCl$_3$)).

FIG. 7 shows the cumulative mortality of immunosuppressed mice infected with L. prolificans FMR 3569 when treated with (a) VRC, voriconazole at 25 mg/kg p.o, by gavage QD; (b) Example 1 at 20 mg/k, p.o, by gavage BID and (c) no treatment.

DETAILED DESCRIPTION OF THE INVENTION

Figure 2B:
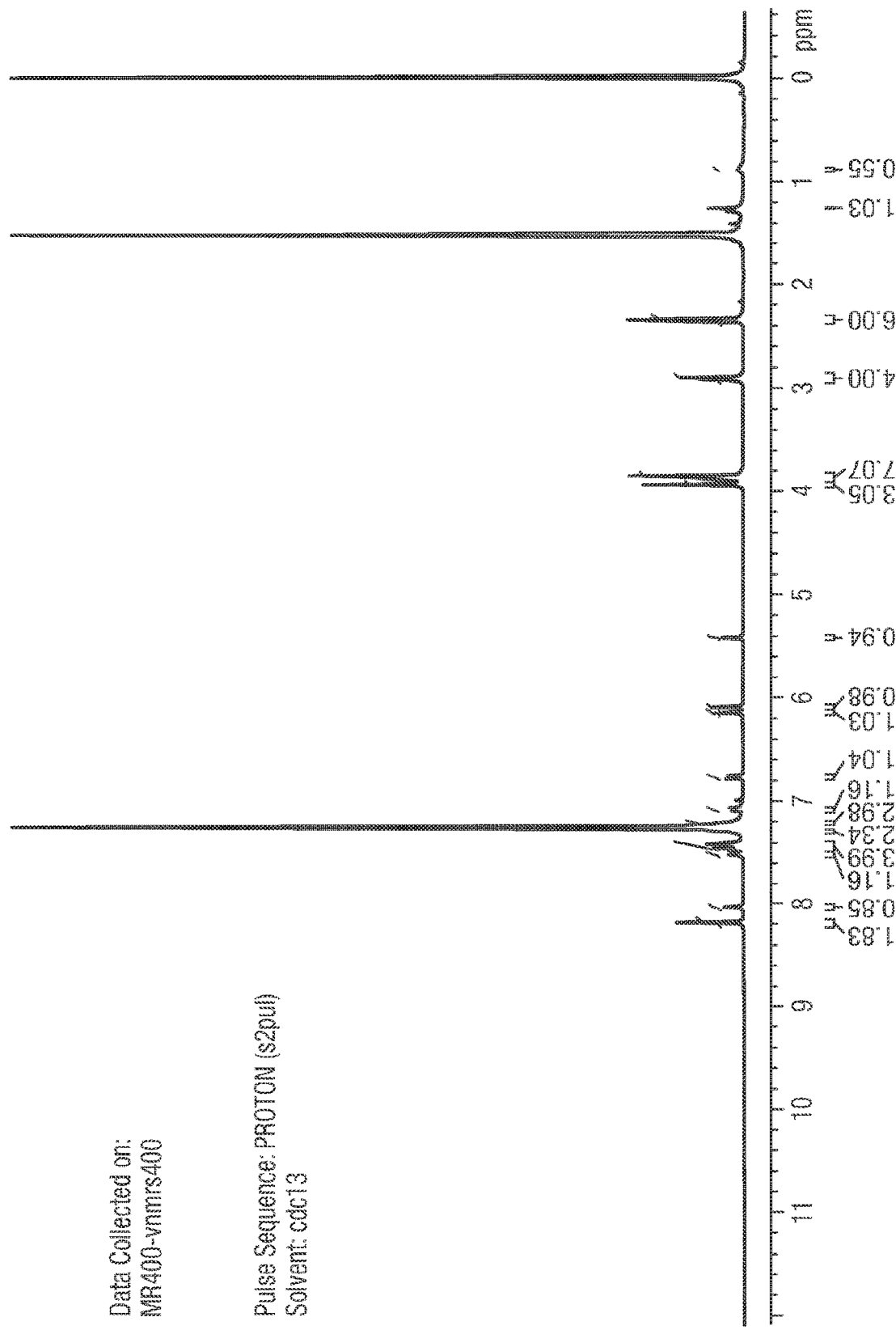
FIG. 2b provides NMR data for 5-(2-(1, 5-Dimethyl-3-phenyl-1H-pyrrol-2-yl)-2-oxoacetamido)-2-(4-(5-fluoropyrimidin-2-yl)piperazin-1-yl)phenyl 2-(1,4-dimethyl-3-phenyl-1H-pyrrol-2-yl)-2-oxoacetate ($^1$H NMR (400 MHz, CDCl$_3$)).

The invention provides a compound, which compound is

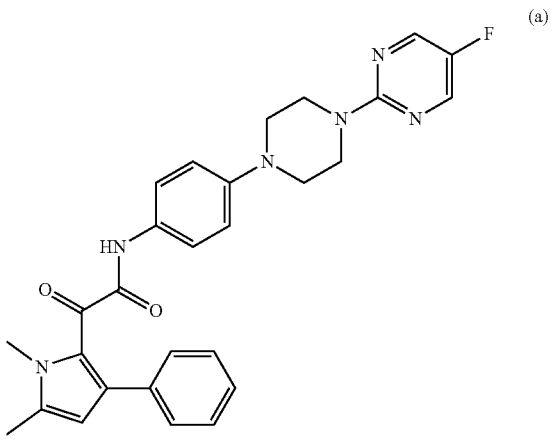 [SMILES: Cc1cc(-c2ccccc2)c(C(=O)C(=O)Nc2ccc(N3CCN(c4ncc(F)cn4)CC3)cc2)n1C]

(a)

2-(1,5-dimethyl-3-phenyl-1H-pyrrol-2-yl)-N-(4-(4-(5-fluoropyrimidin-2-yl)piperazin-1-yl)phenyl)-2-oxoacetamide or a deuterated derivative thereof, or

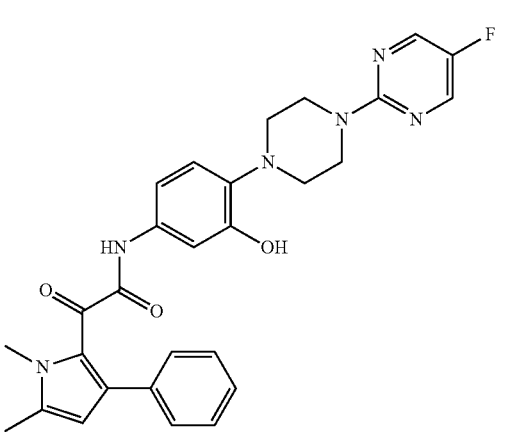

(b)

2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide or a deuterated derivative thereof, or
(c) a prodrug of compound (a) or a prodrug of compound (b), or
a pharmaceutically acceptable salt or agriculturally acceptable salt of (a), (b) or (c).

The compound may, for instance, be 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt or agriculturally acceptable salt thereof, in particular 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof.

Alternatively, the compound may be 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide or a pharmaceutically acceptable salt or agriculturally acceptable salt thereof, in particular 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide or a pharmaceutically acceptable salt thereof. As mentioned above, the addition of the hydroxyl group aids solubility and permeability. In particular, the inclusion of the hydroxyl group lowers c Log P and increases the PSA (polar surface area). The c Log P value of a compound is the logarithm of its partition coefficient between n-octanol and water log(coctanol/cwater). It provides a measure of the hydrophilicity of a compound. A suitable method for measuring Log P can be found in "Leo et al., Chem. Rev., 1971, 71 (6), pp 525-616". A suitable method for measuring PSA can be found in "Ertl, P. ei al., J. Med. Chem. 2000, 43: 3714-3717".

For the avoidance of doubt, the compound can, if desired, be used in the form of solvates. Further, for the avoidance of doubt, the compound may be used in any tautomeric form.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic, hydroiodic or nitric acid and organic acids such as citric, fumaric, maleic, malic, ascorbic, succinic, tartaric, benzoic, acetic, methanesulphonic, ethanesulphonic, benzenesulphonic, p-toluenesulphonic acid, formic, acetic, propionic, glycolic, lactic, pyruvic, oxalic, salicylic, trichloroacetic, picric, trifluoroacetic, cinnamic, pamoic, malonic, mandelic, bismethylene salicylic, ethanedisulfonic, gluconic, citraconic, aspartic, stearic, palmitic, EDTA, p-aminobenzoic or glutamic acid, sulfates, nitrates, phosphates, perchlorates, borates, acetates, benzoates, hydroxynaphthoates, glycerophosphates or ketoglutarates. Further examples of pharmaceutically acceptable inorganic or organic acid addition salts include the pharmaceutically acceptable salts listed in Journal of Pharmaceutical Science, 66, 2 (1977) which are known to the skilled artisan. Pharmaceutically acceptable bases include alkali metal (e.g. sodium or potassium) and alkali earth metal (e.g. calcium or magnesium) hydroxides and organic bases such as alkyl amines, aralkyl amines and heterocyclic amines, lysine, guanidine, diethanolamine and choline.

Also intended as pharmaceutically acceptable acid addition salts are the hydrates which the present compound is able to form.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compound may form solvates with standard low molecular weight solvents using methods known to the skilled artisan.

Prodrug

The present invention also provides a prodrug of compound (a) or a prodrug of compound (b). The compound may, for example, be a prodrug of 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide or the compound may be a prodrug of 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide. The prodrug may, for instance, provide enhanced solubility, permeability, adsorption, distribution and formulation, and/or lower toxicity.

A prodrug is an analogue of the compound of the invention which will be converted in vivo to the desired active compound. Suitable methods will be known to those skilled in the art.

Particularly suitable prodrugs include those in which a nitrogen atom of the compound is quaternised by addition of an ester or alkyl ester group. For example, the nitrogen atom of an amine group may be quaternised by addition of a —CH$_2$—O—COR group, wherein R is typically methyl or tert-butyl.

Other suitable prodrugs include those in which a moiety is added to the phenyl ring adjacent to the piperazinyl group. Relative to the amide (—NH—CO—) moiety, the moiety may be added to the phenyl ring at the ortho or meta position, preferably at the meta position. The prodrug may, for instance, have the general formula:

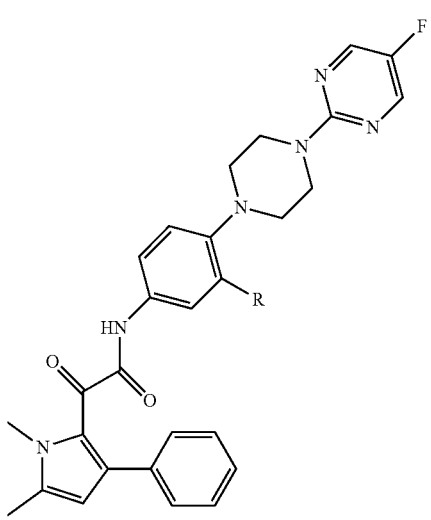

wherein R is a group of formula —O—CO—OR$^1$, —O—CO—R$^1$, —O—CO—NR$^1$R$^2$, —O—CO—(CH$_2$)$_z$—NR$^1$R$^2$, —OR$^1$, —O—(CR$^1$R$^2$)$_z$—O—CO—R$^3$—, —O—P(O)(OR$^4$)(OR$^5$) or —O—(CH$_2$)$_z$—O—P(O)(OR$^4$)(OR$^5$), wherein: R$^1$, R$^2$ and R$^3$ are independently hydrogen, C1-C4 alkyl, C2-C4 alkenyl, C2-C4 alkynyl, C3-C6 cycloalkyl, an unsubstituted 5- to 7-membered heterocyclyl group, or a 5- to 7-membered heterocyclyl group substituted with up to three substituents selected from C1-C4 alkyl and C1-C4 alkoxy; R$^4$ and R$^5$ are independently hydrogen, C1-C4 alkyl, C2-C4 alkenyl, C2-C4 alkynyl or a group I element such as Na; and z is 1, 2, 3 or 4.

As used herein, a C1-C4 alkyl group or moiety can be linear or branched but is preferably linear. Suitable such alkyl groups and moieties include methyl, ethyl, n-propyl, i-propyl, n-butyl, sec-butyl and tert-butyl.

As used herein, a C2-C4 alkenyl group or moiety can be linear or branched but is preferably linear. It contains one or more carbon-carbon double bonds. It is preferably a C2-C3 alkenyl group. Suitable such alkenyl groups and moieties include vinyl, allyl, propenyl and butenyl, e.g. CH$_2$C(Me)=CH$_2$.

As used herein, a C2-C4 alkynyl group or moiety can be linear or branched but is preferably linear. It contains one or more carbon-carbon triple bonds. It is preferably a C2-C3 alkynyl group. Suitable alkynyl groups and moieties include ethynyl, propynyl, and butynyl, and isomers thereof.

As used herein, a C3-C6 cycloalkyl group is typically a C4, C5 or C6 cycloalkyl group, more preferably a C5 or C6 cycloalkyl group.

An alkyl, alkenyl, alkynyl or cycloalkyl group is unsubstituted.

As used herein and unless otherwise stated, a heterocyclyl group or moiety is a saturated 5- to 7-membered ring system in which the ring contains at least one heteroatom. Typically, the ring contains up to three heteroatoms, e.g. one or two heteroatoms, selected from O, S and N. Thus, a heterocyclyl group or moiety is typically a 5- to 7-membered ring containing one, two or three heteroatoms selected from O, S and N. Suitable such heterocyclyl groups and moieties include, for example, monocyclic saturated 5- to 7-membered rings, more preferably monocyclic saturated 5- to 6-membered rings such as tetrahydrofuranyl, piperidinyl, oxazolidinyl, morpholinyl, thiomorpholinyl, pyrrolidinyl, dioxolanyl, piperidonyl, piperazinyl, tetrahydropyranyl and 1,4-diazepanyl, more preferably pyrrolidinyl, piperazinyl, tetrahydropyranyl and piperidinyl.

A heterocyclyl group may be substituted or unsubstituted. Each ring atom may be unsubstituted or may carry one or two substituents. If desired, a nitrogen atom may be disubstituted and a sulphur atom may be substituted, providing a charged heteroatom. Typically, a heterocyclyl group carries up to three substituents, e.g. one or two substituents. The heterocycle may be connected to the remainder of the molecule by a bond to any of its available ring positions. Suitable substituents are C1-C4 alkyl and C1-C4 alkoxy, e.g. methyl, ethyl, methoxy and ethoxy, preferably methyl.

Preferably, R$^1$, R$^2$ and R$^3$ are independently hydrogen, C1-C4 alkyl, C2-C4 alkenyl, C2-C4 alkynyl, C3-C6 cycloalkyl, or an unsubstituted 5- to 6-membered heterocyclyl group. More preferably, R$^1$, R$^2$ and R$^3$ are independently hydrogen, C1-C4 alkyl, C3-C6 cycloalkyl, or an unsubstituted pyrrolidinyl, piperazinyl, tetrahydropyranyl or piperidinyl group.

Preferably, R$^4$ and R$^5$ are independently hydrogen, C1-C4 alkyl, or a group I element such as Na. More preferably, R$^4$ and R$^5$ are independently hydrogen, methyl, ethyl, or Na.

Preferably, z is 1 or 2. More preferably z is 1.

Preferably R is a group of formula-O—CO—OR$^1$, —O—CO—R$^1$, —O—CO—NR$^1$R$^2$, —O—CO—(CH$_2$)$_z$—NR$^1$R$^2$, —OR$^1$, —O—(CR$^1$R$^2$)$_z$—O—CO—R$^3$ or —O—P(O)(OR$^4$)(OR$^5$). More preferably, R is a group of formula —O—COR$^1$, —O—CO—NR$^1$R$^2$, —O—CO—(CH$_2$)$_z$—NR$^1$R$^2$, —OR$^1$, —O—(CR$^1$R$^2$)$_z$—O—CO—R$^3$ or —O—P(O)(OR$^4$)(OR$^5$).

In one embodiment, R is a group of formula-O—CO—OR$^1$, —O—CO—R$^1$, —O—CO—NR$^1$R$^2$, —O—CO—(CH$_2$)$_z$—NR$^1$R$^2$, —OR$^1$, —O—(CR$^1$R$^2$)$_z$—O—CO—R$^3$ or —O—P(O)(OR$^4$)(OR$^5$), wherein: R$^1$, R$^2$ and R$^3$ are independently hydrogen, C1-C4 alkyl, C2-C4 alkenyl, C2-C4 alkynyl, C3-C6 cycloalkyl, or an unsubstituted 5- to 6-membered heterocyclyl group; R$^4$ and R$^5$ are independently hydrogen, C1-C4 alkyl, or a group I element such as Na; and z is 1 or 2. More preferably R is a group of formula —O—COR$^1$, —O—CO—NR$^1$R$^2$, —O—CO—(CH$_2$)$_z$—NR$^1$R$^2$, —OR$^1$, —O—(CR$^1$R$^2$)$_z$—O—CO—R$^3$ or —O—P(O)(OR$^4$)(OR$^5$), wherein R$^1$, R$^2$ and R$^3$ are independently hydrogen, C1-C4 alkyl, C3-C6 cycloalkyl, or an unsubstituted pyrrolidinyl, piperazinyl, tetrahydropyranyl or piperidinyl group; R$^4$ and R$^5$ are independently hydrogen, methyl, ethyl, or Na; and z is 1.

R may, for example, be —OP(O)(ONa)$_2$, —OP(O)(OH)$_2$, —OC(=O)CH$_2$N(H)CH$_3$, —OC(=O)C$_4$NH$_8$, —OC(=O)CH$_3$, —OC(=O)N(CH$_3$)$_2$ or —OCH$_2$OC(=O)C(CH$_3$)$_3$.

In one embodiment, the compound is a pharmaceutically acceptable salt of the prodrug.

Deuterated Derivative

The compound of the invention may be a deuterated derivative of 2-(1,5-dimethyl-3-phenyl-1H-pyrrol-2-yl)-N-

(4-(4-(5-fluoropyrimidin-2-yl)piperazin-1-yl)-3-hydroxyphenyl)-2-oxoacetamide or 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide. Deuterated derivatives of the compounds of the invention have been found to be highly active antifungal agents.

The term deuterated derivative as used herein refers to a compound in which at least one hydrogen atom has been replaced with deuterium, for instance, from 1 to 10 hydrogen atoms may be replaced with deuterium. Two or more hydrogen atoms may be replaced with deuterium. For example, all of the hydrogen atoms on a particular ring within the compound of the invention may be replaced with deuterium.

When, for example, the compound is a deuterated derivative of 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide:
(a) all of the hydrogen atoms on the piperazinyl ring may be replaced with deuterium

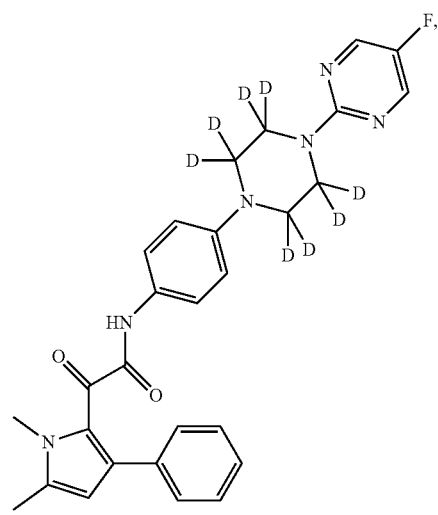 [SMILES: [2H]C1([2H])N(c2ccc(NC(=O)C(=O)c3c(-c4ccccc4)cc(C)n3C)cc2)C([2H])([2H])C([2H])([2H])N(c2ncc(F)cn2)C1([2H])[2H]]

(b) all of the hydrogen atoms on the phenyl ring adjacent to the piperazinyl ring may be replaced with deuterium

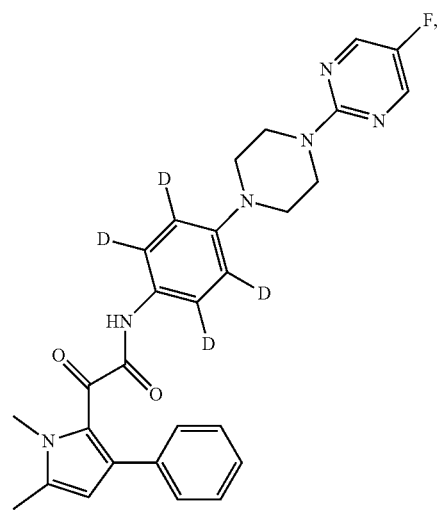 [SMILES: [2H]c1c([2H])c(N2CCN(c3ncc(F)cn3)CC2)c([2H])c([2H])c1NC(=O)C(=O)c1c(-c2ccccc2)cc(C)n1C]

(c) all of the hydrogen atoms on the pyrimidinyl ring may be replaced with deuterium

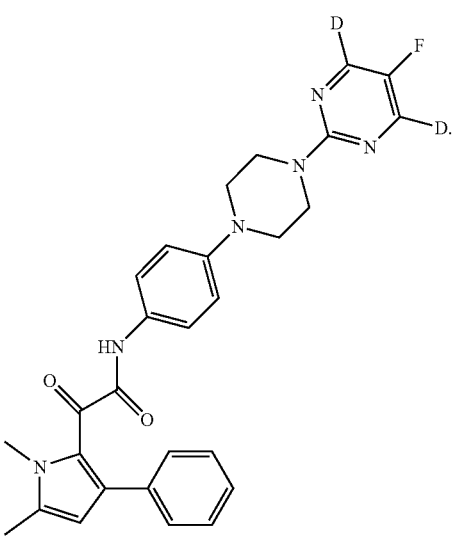

Preferably, (a) all of the hydrogen atoms on the piperazinyl ring are replaced with deuterium, or (b) all of the hydrogen atoms on the phenyl ring adjacent to the piperazinyl ring are replaced with deuterium.

When, for example, the compound is a deuterated derivative of 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide:

(a) all of the hydrogen atoms on the piperazinyl ring may be replaced with deuterium

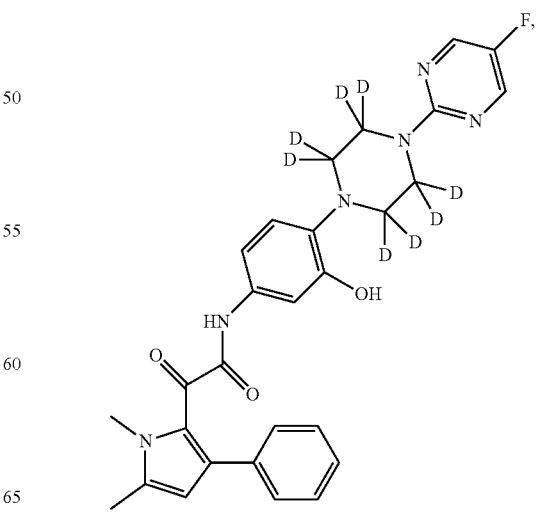

(b) all of the hydrogen atoms on the phenyl ring adjacent to the piperazinyl ring may be replaced with deuterium

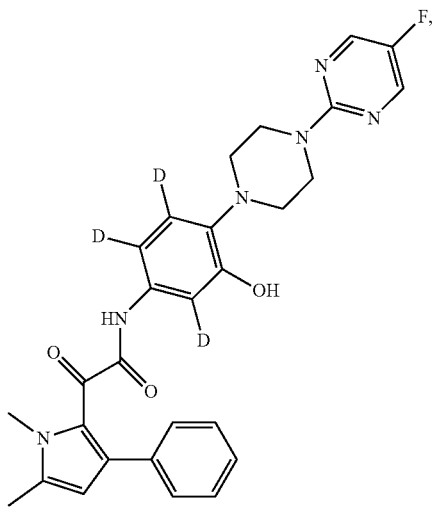 [SMILES: [2H]c1c([2H])c(N2CCN(c3ncc(F)cn3)CC2)c(O)c([2H])c1NC(=O)C(=O)c1c(-c2ccccc2)cc(C)n1C]

(c) all of the hydrogen atoms on the pyrimidinyl ring may be replaced with deuterium

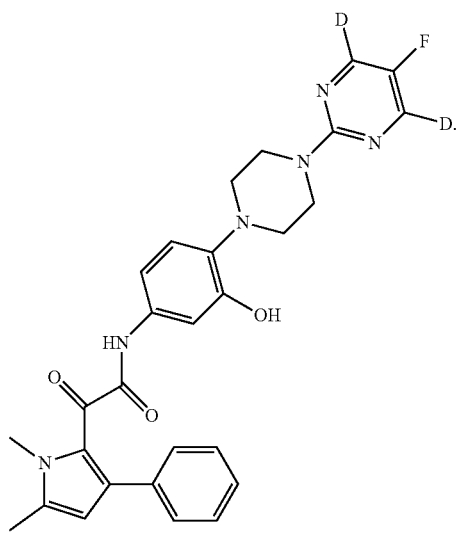

Preferably, (a) all of the hydrogen atoms on the piperazinyl ring are replaced with deuterium, or (b) all of the hydrogen atoms on the phenyl ring adjacent to the piperazinyl ring are replaced with deuterium.

The compound may, for example, be a pharmaceutically acceptable salt of the deuterated derivative.

Synthesis

In one embodiment, the compound of the invention is: 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof.

The compound may be synthesised by reacting a compound of formula (II), with a compound of formula (III). Typically the reaction takes place in the presence of an organic solvent and a base. Preferably the solvent is dichloromethane or tetrahydrofuran and the base is triethylamine or pyridine. Typically the reaction is carried out at 0° C. initially while the reagents are added and then stirred at room temperature until the reaction is complete. The compound of formula (III) is typically available from commercial sources or can be prepared by known methods.

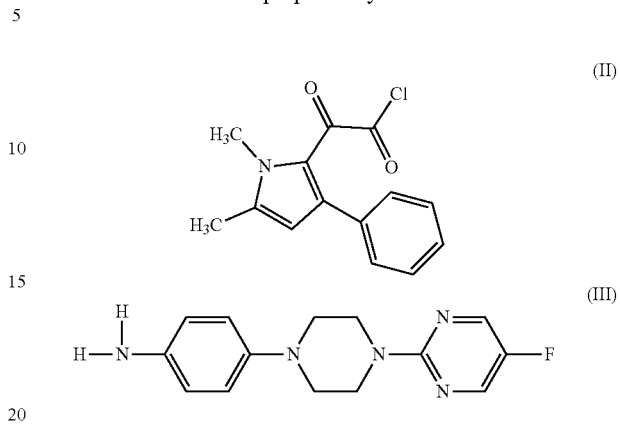

The compound of formula (II) may be prepared by reacting a compound of formula (IV), with preferably oxalyl chloride. Typically the reaction takes place in an organic solvent. Preferably, the solvent is dichloromethane. Typically, the reaction is carried out at 0° C. initially while the reagents are added and then stirred at room temperature until the reaction is complete.

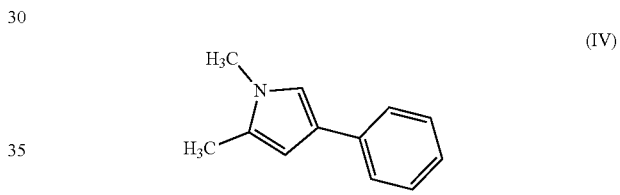

All of the starting materials referred to in the reactions described above are available from commercial sources or can be prepared by analogy with known methods.

In another embodiment, the compound of the invention is: 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide, or a pharmaceutically acceptable salt thereof. In this embodiment, compound (III) has an OH group on the phenyl ring, meta to the —NH$_2$ group.

Deuterated derivates may be synthesised from deuterated starting materials, wherein hydrogen atoms in the starting materials are replaced with deuterium as appropriate to arrive at the target product. For example, to synthesise a deuterated derivative in which the hydrogen atoms on the piperazinyl ring are replaced with deuterium, compound (III) above may comprise deuterium in place of hydrogen on the piperazinyl ring.

The experimental section provides specific synthetic examples.

Pharmaceutical Composition

In one embodiment, the present invention provides a pharmaceutical composition comprising a pharmaceutical compound of the invention, together with one or more pharmaceutically acceptable carriers and/or excipients.

The composition may, for instance, comprise a compound, which compound is 2-(1,5-dimethyl-3-phenyl-1H-pyrrol-2-yl)-N-(4-(4-(5-fluoropyrimidin-2-yl)piperazin-1-yl)phenyl)-2-oxoacetamide or a pharmaceutically acceptable salt thereof, together with one or more pharmaceutically acceptable carriers and/or excipients.

The pharmaceutical composition of the invention typically contains up to 85 wt % of the pharmaceutical compound (for example 2-(1,5-dimethyl-3-phenyl-1H-pyrrol-2-yl)-N-(4-(4-(5-fluoropyrimidin-2-yl)piperazin-1-yl)phenyl)-2-oxoacetamide or a pharmaceutically acceptable salt thereof). More typically, it contains up to 50 wt % of the pharmaceutical compound (for example 2-(1,5-dimethyl-3-phenyl-1H-pyrrol-2-yl)-N-(4-(4-(5-fluoropyrimidin-2-yl)piperazin-1-yl)phenyl)-2-oxoacetamide or a pharmaceutically acceptable salt thereof). Preferred pharmaceutical compositions are sterile and pyrogen free.

Pharmaceutical Combination

The present invention also provides a pharmaceutical combination comprising: (i) a pharmaceutical compound of the invention, and (ii) a second antifungal agent.

The combination may, for example, comprise: (i) a compound which is 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof; and (ii) a second antifungal agent.

Typically, the pharmaceutical combination is a pharmaceutical combination in which pharmaceutical compound (i) and second antifungal agent (ii) are formulated for separate, simultaneous or successive administration. For simultaneous administration, (i) and (ii) may for example be provided in a single composition. For separate or successive administration, (i) and (ii) may, for example, be provided as a kit.

The second antifungal agent used in the invention can be any suitable antifungal agent that the skilled person would judge to be useful in the circumstances. Particularly suitable classes of antifungal agents include azoles, polyenes, purine nucleotide inhibitors, pyrimidine nucleotide inhibitors, mannan inhibitors, protein elongation factor inhibitors, chitin synthase inhibitors, Beta-glucan synthase inhibitors, echinocandins, allylamines, anti-HSP90 antibodies, bactericidal/permeability inducing protein products and polyoxins. Other suitable antifungal agents which do not fall within the classes above include the compounds 5-fluoro-1,3-dihydro-1-hydroxy-2,1-benzoxaborale (AN269), 5-chloro-1,3-dihydro-1-hydroxy-2,1-benzoxaborale (AN2718) and icofungipen. For instance, the second antifungal agent may be selected from the group consisting of azoles, polyenes, purine nucleotide inhibitors, pyrimidine nucleotide inhibitors, mannan inhibitors, protein elongation factor inhibitors, echinocandins, allylamines, anti-HSP90 antibodies, bactericidal/permeability inducing protein products or polyoxins, or one of the compounds 5-fluoro-1,3-dihydro-1-hydroxy-2,1-benzoxaborale (AN269), 5-chloro-1,3-dihydro-1-hydroxy-2,1-benzoxaborale (AN2718), icofungipen, VT116 or SCY078.

VT116 is 2-Pyridineethanol, α-(2,4-difluorophenyl)-β,β-difluoro-α-(1H-tetrazol-1-ylmethyl)-5-[4-(2,2,2-trifluoroethoxy)phenyl]-, (αR)-,

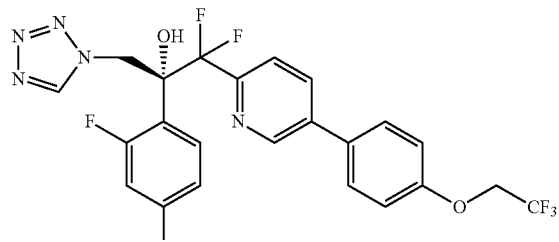

VT-1161 and SCY078 078 (aka MK-3118) is a semi-synthetic derivative of enfumafungin, 4H-1,4a-Propano-2H-phenanthro[1,2-c]pyran-7-carboxylic acid, 15-[(2R)-2-amino-2,3,3-trimethylbutoxy]-8-[(1R)-1,2-dimethylpropyl]-1,6,6a,7,8,9,10,10a,10b,11,12,12a-dodecahydro-1,6a,8,10a-tetramethyl-14-[5-(4-pyridinyl)-1H-1,2,4-triazol-1-yl]-, (1S,4aR,6aS,7R,8R,10aR,10bR,12aR,14R,15R):

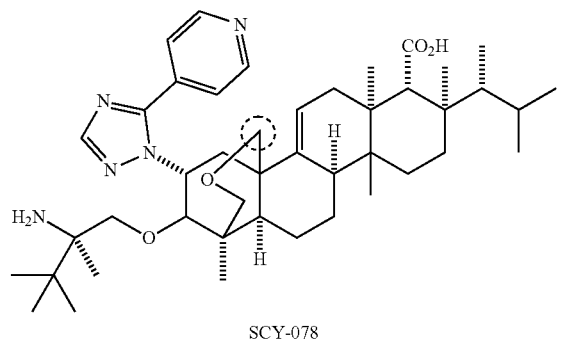

SCY-078

Preferred azoles are clotrimazole, econazole, bifonazole, butoconazole, fenticonazole, fluconazole, isoconazole, itraconazole, ketoconazole, miconazole, oxiconazole, sertaconazole, sulconazole, tioconazole, isavuconazole, ravuconazole, posaconazole, terconazole and voriconazole, luliconazole. Preferred echinocandins are anidulafungin, caspofungin micafungin and biafungin. Preferred allylamines are terbinafine, butenafine, amorolfine and naftifine. Preferred polyenes are amphotericin B and nystatin. A preferred example of a purine or pyrimidine nucleotide inhibitor is flucytosine. A preferred mannan inhibitor is pradamicin. A preferred protein elongation factor inhibitor is sordarin and analogues thereof. A preferred polyoxin is nikkomycin Z.

Particularly preferred second antifungal agents are caspofungin, micafungin, anidulofungin, amphotericin B, voriconazole, posaconazole, isavuconazole, fluconazole and itraconazole.

The pharmaceutical combination may be formulated as a single composition. Thus, the pharmaceutical composition may, for example, comprise (i) a pharmaceutical compound of the invention (e.g. 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof), (ii) a second antifungal agent as defined herein, and (iii) a pharmaceutically acceptable carrier or diluent.

Medical Uses

In one embodiment, (i) a pharmaceutical compound of the invention, e.g. 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, (ii) a pharmaceutical composition as defined herein or (iii) a pharmaceutical combination as defined herein, may be for use in a method of treatment of the human or animal body by therapy.

Accordingly, (i) a pharmaceutical compound of the invention, (ii) a pharmaceutical composition as defined herein or (iii) a pharmaceutical combination as defined herein, may be for use in the prevention or treatment of fungal disease, for example, (i) or (ii) may be used in combination with a second antifungal agent. In particular, 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof may be used in combination with a second antifungal agent, as desired. The second antifungal agent may be a second antifungal agent as defined herein.

The pharmaceutical compound of the invention (for example 2-(1,5-dimethyl-3-phenyl-TH-pyrrol-2-yl)-N-(4-(4-(5-fluoropyrimidin-2-yl)piperazin-1-yl)phenyl)-2-oxoacetamide, or a pharmaceutically acceptable salt thereof), pharmaceutical combinations of the invention and pharmaceutical compositions of the invention may be administered in a variety of dosage forms. Thus, it can be administered orally, for example as a tablet, troche, capsules, lozenge, aqueous or oily suspension, dispersible powder or granules. The pharmaceutical compound of the invention (for example 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof), pharmaceutical combinations of the invention and pharmaceutical compositions of the invention may also be administered parenterally, either subcutaneously, intravenously, intramuscularly, intrasternally, transdermally or by infusion techniques, for example, pharmaceutical combinations of the invention and pharmaceutical compositions of the invention may be administered intravenously. Depending on the vehicle and concentration used, the drugs can either be suspended or dissolved in the vehicle. Advantageously, adjuvants such as a local anaesthetic, preservative and buffering agent can be dissolved in the vehicle. The pharmaceutical compound of the invention (for example 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof) pharmaceutical combinations, and pharmaceutical compositions may also be administered as suppositories. The pharmaceutical compound of the invention (for example 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof), pharmaceutical combinations and pharmaceutical compositions may be administered by inhalation in the form of an aerosol via an inhaler or nebuliser. The pharmaceutical compound of the invention (for example 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof), pharmaceutical combinations and pharmaceutical compositions may be administered topically, for example, as a cream, foam, gel, lotion, or ointment.

The pharmaceutical compound of the invention (for example 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof), and optionally a second antifungal agent, is typically formulated for administration with a pharmaceutically acceptable carrier or diluent. For example, solid oral forms may contain, together with the active compound, solubilising agents, e.g. cyclodextrins or modified cyclodextrins; diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film coating processes.

Liquid dispersions for oral administration may be solutions, syrups, emulsions and suspensions. The solutions may contain solubilising agents e.g. cyclodextrins or modified cyclodextrins. The syrups may contain as carriers, for example, saccharose or saccharose with glycerine and/or mannitol and/or sorbitol.

Suspensions and emulsions may include pharmaceutically active compounds in which the average particle size has undergone particle size reduction by micronisation or nanonisation technologies. For instance, the average particle size of the compound of the invention may have undergone particle size reduction by micronisation or nanonisation technologies.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol; solubilising agents, e.g. cyclodextrins or modified cyclodextrins, and if desired, a suitable amount of lidocaine hydrochloride.

Solutions for intravenous or infusions may contain as carrier, for example, sterile water and solubilising agents, e.g. cyclodextrins or modified cyclodextrins, or preferably they may be in the form of sterile, aqueous, isotonic saline solutions.

Nanoformulations are also envisaged.

For topical application to the skin, the compound may, for example, be made up into a cream, lotion or ointment. Cream or ointment formulations which may be used for the drug are conventional formulations well known in the art, for example as described in standard textbooks of pharmaceutics such as the British Pharmacopoeia.

For topical application by inhalation, the compound may be formulated for aerosol delivery for example, by pressure-driven jet atomizers or ultrasonic atomizers, or preferably by propellant-driven metered aerosols or propellant-free administration of micronized powders, for example, inhalation capsules or other "dry powder" delivery systems. Excipients, such as, for example, propellants (e.g. Frigen in the case of metered aerosols), surface-active substances, emulsifiers, stabilizers, preservatives, flavorings, and fillers (e.g. lactose in the case of powder inhalers) may be present in such inhaled formulations. For the purposes of inhalation, a large number of apparata are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described in European Patent Application EP 0 505 321).

For topical application to the eye, the compound may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

A therapeutically effective amount of a pharmaceutical compound of the invention (for example 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof) may be administered to a patient. A typical daily dose is up to 200 mg, e.g. up to 100 mg or up to 50 mg per kg of body weight, for example from 0.001 to 200 or 0.001 to 50 mg per kg of body weight, according to the activity of the pharmaceutical compound of the invention (for example 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof) or combination of specific antifungal agents used, the age, weight and conditions of the subject to be treated, the type and severity of the disease and the frequency and route of administration. Preferably, daily dosage levels are up to 200 mg, e.g. up to 150 mg, up to 100 mg, up to 50 mg or up to 40 mg per kg of body weight. Daily dosage levels are for example at least 1 mg, at least 2 mg or at least 5 mg per kg of body weight. In one embodiment the daily dosage level is from 0.05 mg to 2 g, preferably from 0.1 mg to 10 mg. Where a combination is administered, a pharmaceutical compound of the invention (for example 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof) is typically administered in an amount of at least 0.05 mg, preferably at least 0.1 mg, 2 mg or at least 5 mg. A preferred upper limit on the amount of compound of the invention administered is typically 200 mg, e.g. 100 mg, 50 mg or 25 mg. The second antifungal agent is typically administered at or below the standard dose used for that drug. An advantage of the combinations of the present invention is that known antifungal agents may be administered in lower doses than are currently used, resulting in a reduction in toxic effects. The pharmaceutical compound of the invention (for example 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof), combination of the invention or composition of the invention is typically administered to the patient in a non-toxic amount.

When, for example, a pharmaceutical compound of the invention (for example 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof) is part of a pharmaceutical combination as defined herein, formulated for separate, simultaneous or successive administration, (a) a pharmaceutical compound of the invention (for example 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof), and (b) the second antifungal agent may be administered by the same mode of administration or by different modes of administration.

Typically, the pharmaceutical compound of the invention (for example 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof) is for use in the prevention or treatment by intravenous administration of a fungal disease. Thus, typically, the pharmaceutical compound of the invention (for example 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof) is administered intravenously. If a second antifungal agent is administered separately, simultaneously or successively, the second antifungal agent may be administered intravenously or by a different mode of administration, which different mode of administration may be as defined herein.

Preferably, the fungal disease comprises an infection by a fungus, for example an Ascomycete. Preferably, the fungal disease comprises an infection by an organism selected from the genera *Absidia; Acremonium; Alternaria; Aspergillus; Bipolaris; Blastomyces; Blumeria; Cladosporium; Coccidioides; Colletotrichium; Curvularia; Encephalitozoon; Epicoccum; Epidermophyton; Exophiala; Exserohilum; Fusarium; Histoplasma; Leptosphaeria; Microsporum; Mycosphaerella; Neurospora, Paecilomyces; Penicillium; Phytophthora; Plasmopara; Pneumocystis; Pyricularia; Pythium; Puccinia; Rhizoctonia; Rhizomucor; Scedosporium; Scopulariopsis; Trichophyton; Trichosporon*; and *Ustilago*.

Preferably, the fungal disease comprises an infection by an organism of the genus *Aspergillus, Scedosporium* or *Fusarium*, for instance, the fungal disease comprises an infection by an organism of the genus *Aspergillus* or *Scedosporium*, in particular *Aspergillus*.

In one embodiment, the fungal disease comprises an infection by an organism of the genus *Aspergillus*. In another embodiment, the fungal disease comprises an infection by an organism of the genus *Scedosporium*.

Preferably, the fungal disease comprises an infection by an organism selected from the species *Absidia corymbifera; Acremonium* spp; *Alternaria alternata; Aspergillus* flavus; *Aspergillus* fumigatus; *Aspergillus* nidulans; *Aspergillus* niger; *Aspergillus* parasiticus; *Aspergillus terreus; Bipolaris* spp; *Blastomyces dermatitidis; Blumeria graminis; Cladosporium cladosporoides; Cladosporium herbarium; Coccidioides immitis, Coccidioides posadasii; Curvularia lunata; Colletotrichium trifolii; Encephalitozoon cuniculi; Epicoccum nigrum; Epidermophyton floccosum; Exophiala* spp; *Exserohilum rostratum; Fusarium graminarium; Fusarium solani; Fusarium sporotrichoides; Histoplasma capsulatum; Leptosphaeria nodorum; Microsporum canis; Mycosphaerella graminicola; Paecilomyces lilanicus; Paecilomyces varioti; Penicillium chrysogenum; Phytophthora capsici; Phytophthora infestans; Plasmopara viticola; Pneumocystis jiroveci; Puccinia coronata; Puccinia graminis; Pyricularia oryzae; Pythium ultimum; Rhizoctonia solani; Rhizomucor* spp; *Rhizopus* spp; *Scedosporium apiospermum; Scedosporium prolificans; Scedosporium* species d; *Scopulariopsis brevicaulis; Trichophyton mentagrophytes; Trichophyton interdigitale; Trichophyton rubrum; Trichosporon asahii; Trichosporon beigelii*; and *Ustilago maydis*.

Preferably, the fungal disease comprises an infection by *A. fumigatus, A. flavus, A. terreus, A. niger, A, lentulus, S. apiospermum, S. prolificans*, or S. species d. Particularly, the fungal disease comprises an infection by *A. fumigatus, A. flavus, A. terreus* or *A. niger*. In one embodiment, the fungal disease comprises an infection by *S. prolificans*.

Examples of fungal diseases, which can be prevented or treated using a compound of the invention (for example 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof) include both systemic and superficial infections. The fungal diseases include invasive fungal diseases caused by *Aspergillus* species such as aspergillosis, but also local forms of these infections. For instance, the fungal diseases include invasive fungal diseases caused by *Aspergillus* species such as aspergillosis, but also local forms of these infections. The compound of the invention (for example 2-(1,5-dimethyl-3-phenyl-1H-pyrrol-2-yl)-N-(4-(4-(5-fluoropyrimidin-2-yl)

piperazin-1-yl)phenyl)-2-oxoacetamide, or a pharmaceutically acceptable salt thereof) is particularly useful against diseases caused by *Aspergillus* species, for which a fungicidal drug is required which has lower toxicity than amphotericin. The invention also provides for the treatment of dermatological infections.

In one embodiment, a pharmaceutical compound of the invention (for example 2-(1,5-dimethyl-3-phenyl-1H-pyrrol-2-yl)-N-(4-(4-(5-fluoropyrimidin-2-yl)piperazin-1-yl) phenyl)-2-oxoacetamide, or a pharmaceutically acceptable salt thereof) is for use in the prevention or treatment of a disease caused by *Aspergillus* species. The diseases caused by *Aspergillus* species include diseases caused by *A. fumigatus*, *A. flavus*, *A. terreus* and *A. niger*.

Examples of systemic infections which might be prevented or treated using a pharmaceutical compound of the invention (for example 2-(1,5-dimethyl-3-phenyl-1H-pyrrol-2-yl)-N-(4-(4-(5-fluoropyrimidin-2-yl)piperazin-1-yl) phenyl)-2-oxoacetamide, or a pharmaceutically acceptable salt thereof) include: pulmonary aspergillosis, e.g. in immunosuppressed patients such as bone marrow recipients or AIDS patients; systemic aspergillosis; rhinocerebral mucomycosis; blastomycosis; histoplasmosis; coccidiomycosis; paracoccidiomycosis; lobomycosis; sporotrichosis; chromoblastomycosis; phaeohyphomycosis; and disseminated sporotrichosis, Examples of superficial infections, which can be prevented or treated using a pharmaceutical compound (for example 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof) include: ring worm; athlete's foot; and tinea unguium (nail infection).

Examples of diseases or conditions which are caused by fungi or where fungi exacerbate an allergic response, and which can be prevented or treated using a pharmaceutical compound (for example 2-(1,5-dimethyl-3-phenyl-1H-pyrrol-2-yl)-N-(4-(4-(5-fluoropyrimidin-2-yl)piperazin-1-yl) phenyl)-2-oxoacetamide or a pharmaceutically acceptable salt thereof), include allergic bronchopulmonary aspergillosiis (ABPA); asthma, Severe asthma with Fungal Sensitisation (SAFS), fungal colonization of cystic fibrosis, rhinosinusitis and sinusitis. For instance, the disease may be caused by a fungal sensitisation, or the disease may be Allergic Bronchopulmonary Aspergillosis (ABPA) or asthma.

The present invention also provides a kit comprising, in admixture or in separate containers, a compound as defined herein, and a second antifungal agent.

For example, the kit may comprise, in admixture or in separate containers, a compound, which compound is 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, and a second antifungal agent.

Further provided by the invention is a method of preventing or treating fungal disease in a subject which method comprises administering to said subject an effective amount of: (i) a pharmaceutical compound of the invention as defined herein, (ii) a composition comprising the pharmaceutical compound, together with one or more pharmaceutically acceptable carriers and/or excipients, or (iii) a combination comprising: (a) a pharmaceutical compound of the invention; and (b) a second antifungal agent.

The second antifungal agent may be a second antifungal agent as defined hereinabove.

The fungal disease may be a fungal disease as defined herein. For instance, the disease may be caused by a fungal dermatophyte. Alternatively, the disease may be Allergic Bronchopulmonary Aspergillosis (ABPA) or SAFS. As a further alternative, the disease may be asthma.

The invention also provides the use of a pharmaceutical compound, composition or combination of the invention in the manufacture of a medicament for the prevention or treatment of a fungal disease.

The second antifungal agent may be a second antifungal agent as defined hereinabove.

The fungal disease may be a fungal disease as defined herein. For instance, the disease may be caused by a fungal dermatophyte. Alternatively, the disease may be Allergic Bronchopulmonary Aspergillosis (ABPA). As a further alternative, the disease may be asthma.

Agricultural Uses

The present invention also provides a method of controlling a fungal disease in a plant, which method comprises applying to the locus of the plant a compound which is: 2-(1,5-dimethyl-3-phenyl-1H-pyrrol-2-yl)-N-(4-(4-(5-fluoropyrimidin-2-yl)piperazin-1-yl)phenyl)-2-oxoacetamide or an agriculturally acceptable salt thereof, or 2-(1,5-dimethyl-3-phenyl-1H-pyrrol-2-yl)-N-(4-(4-(5-fluoropyrimidin-2-yl) piperazin-1-yl)-3-hydroxyphenyl)-2-oxoacetamide or an agriculturally acceptable salt thereof. Optionally a second antifungal agent may also be present.

For example, the method may comprise applying to the locus of the plant a compound which is: 2-(1,5-dimethyl-3-phenyl-1H-pyrrol-2-yl)-N-(4-(4-(5-fluoropyrimidin-2-yl) piperazin-1-yl)phenyl)-2-oxoacetamide or an agriculturally acceptable salt thereof, and optionally a second antifungal agent.

The compound (for instance 2-(1,5-dimethyl-3-phenyl-1H-pyrrol-2-yl)-N-(4-(4-(5-fluoropyrimidin-2-yl)piperazin-1-yl)phenyl)-2-oxoacetamide, or an agriculturally acceptable salt thereof), may, for example, be applied to the seeds of the plants, to the medium (e.g. soil or water) in which the plants are grown, or to the foliage of the plants.

The compound (for instance 2-(1,5-dimethyl-3-phenyl-1H-pyrrol-2-yl)-N-(4-(4-(5-fluoropyrimidin-2-yl)piperazin-1-yl)phenyl)-2-oxoacetamide, or an agriculturally acceptable salt thereof) is preferably used in the treatment or prevention of fungal diseases. Examples of fungal diseases of plants which can be controlled using the compound (for instance 2-(1,5-dimethyl-3-phenyl-1H-pyrrol-2-yl)-N-(4-(4-(5-fluoropyrimidin-2-yl)piperazin-1-yl)phenyl)-2-oxoacetamide or an agriculturally acceptable salt thereof) include fungal diseases caused by the following plant pathogens: *Blumeria graminis*; *Colletotrichium trifolii*; *Fusarium graminearium*; *Fusarium solani*; *Fusarium sporotrichoides*; *Leptosphaeria nodorum*; *Magnaporthe grisea*; *Mycosphaerella graminicola*; *Neurospora crassa*; *Phytophthora capsici*; *Phytophthora infestans*; *Plasmopara viticola*; *Puccinia coronata*; *Puccinia graminis*; *Pyricularia oryzae*; *Pythium ultimum*; *Rhizoctonia solani*; *Trichophyton rubrum*; and *Ustilago maydis*.

The present invention includes an agricultural composition comprising a compound, which is: 2-(1,5-dimethyl-3-phenyl-1H-pyrrol-2-yl)-N-(4-(4-(5-fluoropyrimidin-2-yl) piperazin-1-yl)phenyl)-2-oxoacetamide or an agriculturally acceptable salt thereof, or 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide or an agriculturally acceptable salt thereof; and an agriculturally acceptable carrier or diluent.

The agricultural composition may, for example, comprise a compound, which is: 2-(1,5-dimethyl-3-phenyl-1H-pyrrol-2-yl)-N-(4-(4-(5-fluoropyrimidin-2-yl)piperazin-1-yl)phenyl)-2-oxoacetamide or an agriculturally acceptable salt thereof, and an agriculturally acceptable carrier or diluent.

Alternatively, the agricultural composition may, for example, comprise a compound, which is: 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide or an agriculturally acceptable salt thereof, and an agriculturally acceptable carrier or diluent In one embodiment of the invention, the composition further comprises a second antifungal agent. Examples include those as defined herein.

Said agricultural composition typically contains up to 85 wt % of: 2-(1,5-dimethyl-3-phenyl-1H-pyrrol-2-yl)-N-(4-(4-(5-fluoropyrimidin-2-yl)piperazin-1-yl)phenyl)-2-oxoacetamide or an agriculturally acceptable salt thereof, or 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide or an agriculturally acceptable salt thereof. More typically, it contains up to 50 wt % of: 2-(1,5-dimethyl-3-phenyl-1H-pyrrol-2-yl)-N-(4-(4-(5-fluoropyrimidin-2-yl)piperazin-1-yl)phenyl)-2-oxoacetamide or an agriculturally acceptable salt thereof, or 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide or an agriculturally acceptable salt thereof of. When used in an agricultural composition, the skilled person will readily be able to determine suitable levels of administration. As examples, the antifungal agent(s) can be used at a level of from 5 g to 10 kg per hectare, for example from 10 g to 5 kg per hectare, for example from 100 g to 2 kg per hectare.

Suitable agriculturally acceptable salts include salts with agriculturally acceptable acids, both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Salts may also be formed with agriculturally acceptable bases such as alkali metal (e.g. sodium or potassium) and alkaline earth metal (e.g. calcium or magnesium) hydroxides and organic bases such as alkyl amines, aralkyl amines or heterocyclic amines. A preferred agriculturally acceptable salt is the hydrochloride salt.

2-(1,5-dimethyl-3-phenyl-1H-pyrrol-2-yl)-N-(4-(4-(5-fluoropyrimidin-2-yl)piperazin-1-yl)phenyl)-2-oxoacetamide or an agriculturally acceptable salt thereof, or 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide or an agriculturally acceptable salt thereof, and optional second antifungal agents, may be applied in combination with inert carriers or diluents, as in aqueous sprays, granules and dust formulations in accordance with established practice in the art. An aqueous spray is usually prepared by mixing a wettable powder or emulsifiable concentrate formulation of a compound of the invention with a relatively large amount of water to form a dispersion.

Wettable powders may comprise an intimate, finely divided mixture of a compound of the invention, an inert solid carrier and a surface-active agent. The inert solid carrier is usually chosen from among the attapulgite clays, the kaolin clays, the montmorillonite clays, the diatomaceous earths, finely divided silica and purified silicates. Effective surfactants, which have wetting, penetrating and dispersing ability are usually present in a wettable powder formulation in proportions of from 0.5 to 10 percent by weight. Among the surface active agents commonly used for this purpose are the sulfonated lignins, naphthalenesulfonates, naphthalenesulfonates and condensed naphthalenesulfonates, alkylbenzenesulfonates, alkyl sulfates and non-ionic surfactants such as products of condensation of ethylene oxide with alkylphenols.

Emulsifiable concentrates may comprise a solution of: 2-(1,5-dimethyl-3-phenyl-1H-pyrrol-2-yl)-N-(4-(4-(5-fluoropyrimidin-2-yl)piperazin-1-yl)phenyl)-2-oxoacetamide or an agriculturally acceptable salt thereof, or 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide or an agriculturally acceptable salt thereof, in a liquid carrier which is a mixture of a water-immiscible solvent and a surfactant, including an emulsifier. Useful solvents include aromatic hydrocarbon solvents such as the xylenes, alkylnaphthalenes, petroleum distillates, terpene solvents, ether-alcohols and organic ester solvents. Suitable emulsifiers, dispersing and wetting agents may be selected from the same classes of products which are employed in formulating wettable powders.

The invention also provides the use of a compound, which compound is: 2-(1,5-dimethyl-3-phenyl-1H-pyrrol-2-yl)-N-(4-(4-(5-fluoropyrimidin-2-yl)piperazin-1-yl)phenyl)-2-oxoacetamide or an agriculturally acceptable salt thereof, or 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide or an agriculturally acceptable salt thereof, optionally together with a second antifungal agent, as an agricultural fungicide.

The use may, for example, be the use of a compound, which compound is: 2-(1,5-dimethyl-3-phenyl-1H-pyrrol-2-yl)-N-(4-(4-(5-fluoropyrimidin-2-yl)piperazin-1-yl)phenyl)-2-oxoacetamide, or an agriculturally acceptable salt thereof, optionally together with a second antifungal agent, as an agricultural fungicide.

Alternatively, the use may, for example, be the use of a compound, which compound is: 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide, or an agriculturally acceptable salt thereof, optionally together with a second antifungal agent, as an agricultural fungicide.

The second antifungal agent may be any antifungal agent suitable for use in agriculture. Examples include those as defined herein.

The fungicide formulations desirably contain from 0.1 percent to 95 percent by weight of: 2-(1,5-dimethyl-3-phenyl-1H-pyrrol-2-yl)-N-(4-(4-(5-fluoropyrimidin-2-yl)piperazin-1-yl)phenyl)-2-oxoacetamide or an agriculturally acceptable salt thereof, or 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide or an agriculturally acceptable salt thereof, or in the case of a combination of antifungal agents the total weight of antifungal agent, and from 0.1 to 75 percent of an inert carrier or surfactant. The direct application to plant seeds prior to planting may be accomplished in some instances by mixing either a powdered solid of: 2-(1,5-dimethyl-3-phenyl-1H-pyrrol-2-yl)-N-(4-(4-(5-fluoropyrimidin-2-yl)piperazin-1-yl)phenyl)-2-oxoacetamide or an agriculturally acceptable salt thereof, or 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide or an agriculturally acceptable salt thereof, or a dust formulation with seed to obtain a substantially uniform coating which is very thin and represents only one or two percent by weight or less, based on the weight of the seed.

In some instances, however, a non-phytotoxic solvent such as methanol is conveniently employed as a carrier to facilitate the uniform distribution of: 2-(1,5-dimethyl-3-phenyl-1H-pyrrol-2-yl)-N-(4-(4-(5-fluoropyrimidin-2-yl)piperazin-1-yl)phenyl)-2-oxoacetamide or an agriculturally acceptable salt thereof, or 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide or an agriculturally acceptable salt thereof, on the surface of the seed.

When a compound, which compound is: 2-(1,5-dimethyl-3-phenyl-1H-pyrrol-2-yl)-N-(4-(4-(5-fluoropyrimidin-2-yl)piperazin-1-yl)phenyl)-2-oxoacetamide or an agriculturally acceptable salt thereof, or 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide or an agriculturally acceptable salt thereof, or in the case of a combination of antifungal agents one of the antifungal agents used, is to be applied to the soil, as for pre-emergence protection, granular formulations or dusts are sometimes more convenient than sprays. A typical granular formulation comprises: 2-(1,5-dimethyl-3-phenyl-1H-pyrrol-2-yl)-N-(4-(4-(5-fluoropyrimidin-2-yl)piperazin-1-yl)phenyl)-2-oxoacetamide or an agriculturally acceptable salt thereof, or 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide or an agriculturally acceptable salt thereof, dispersed on an inert carrier such as coarsely ground clay, or clay which has been converted to granules by treatment of a rolling bed of the powdered material with a small amount of liquid in a granulating drum. In the usual process for preparing granular formulations, a solution of the active compound is sprayed on the granules while they are being agitated in a suitable mixing apparatus, after which the granules are dried with a current of air during continued agitation. Dust formulations customarily employ essentially the same inert diluents as wettable powders and granules, but are well-mixed in powder form and do not usually contain emulsifiers. Dusts may contain some surface active agents to facilitate uniform distribution of the active ingredient in the formulation and to improve the uniformity and adhesion of the dust coating on seeds and plants. The colloidal dispersion of dust formulations in the air is usually prevented by incorporation of a minor amount of an oily or waxy material in the formulation to cause agglomeration of colloidal size particles. In this way the dust may be applied to seeds or plants without generation of an air-polluting aerosol.

The following examples illustrate the invention but are not intended to limit the scope of the invention. In this regard, it is important to understand that the particular assays used in the Examples section are designed only to provide an indication of anti-fungal activity. There are many assays available to determine such activity, and a negative result in any one particular assay is therefore not determinative.

EXAMPLES

Synthesis of the Compounds of the Invention

1. Synthesis of Example 1: 2-(1,5-dimethyl-3-phenyl-1H-pyrrol-2-yl)-N-(4-(4-(5-fluoropyrimidin-2-yl)piperazin-1-yl)phenyl)-2-oxoacetamide The synthetic scheme below provides a method of synthesis of:

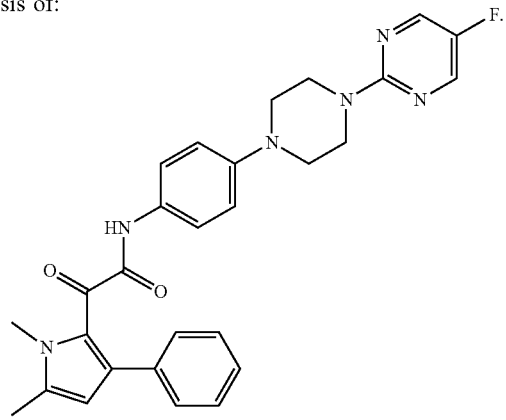

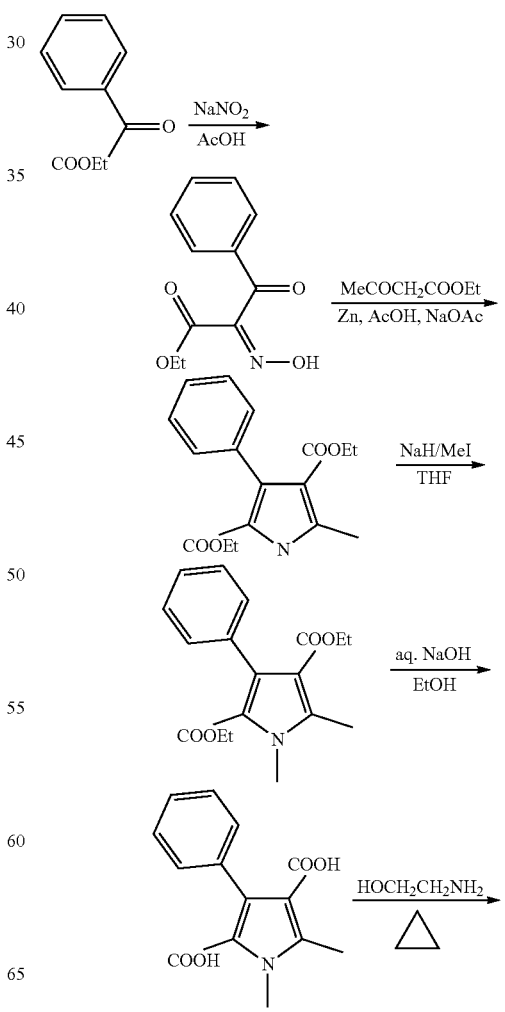

-continued

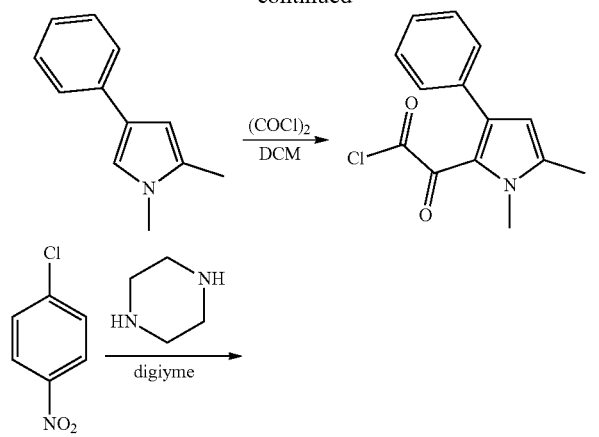

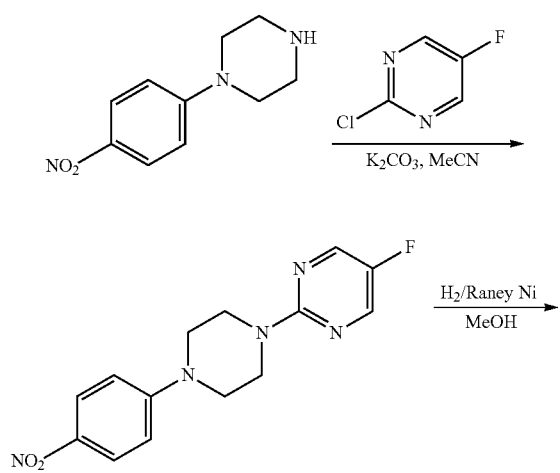

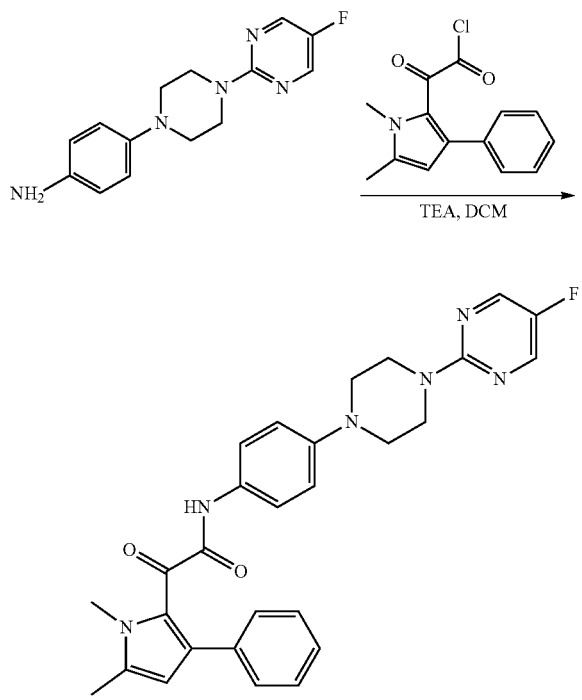

2-Hydroximino-3-oxo-3-phenyl propionic acid ethyl ester (A)

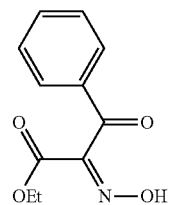 [SMILES: CCOC(=O)/C(=N/O)C(=O)c1ccccc1]

A solution of sodium nitrite (1.07 Kg, 45.62 mol) in water (4 L) was added slowly to a solution of ethyl benzoyl acetate (2 Kg, 10.41 mol) in glacial acetic acid (6 L), at 0-10° C. over a period of 2 h. The product started precipitating during the course of addition. The reaction mass was warmed to room temperature and stirred for a further 1 h. Water (2.5 L) was added and the mixture stirred for a further 1 h. Filtered under suction, washed with water (2 L). The solid was dissolved in chloroform (8 L) and washed with water (2×500 mL), brine solution (2×500 mL), dried over anhydrous sodium sulfate and concentrated in vacuo to dryness to afford 2.0 Kg (86%) of 2-hydroxyimino-3-oxo-3-phenyl propionic acid ethyl ester A as a white solid. [TLC system: Ethyl acetate:Pet ether (3:7); $R_f$ value: 0.28].

5-Methyl-3-phenyl-H-pyrrole-24 dicarboxylic acid diethyl ester (B)

A mixture of ethyl acetoacetate (329 g, 2.53 mol), zinc dust (443 g, 6.78 mol) and anhydrous sodium acetate (463 g, 5.65 mol) in glacial acetic acid (800 mL) were heated to 60° C. A solution of A (500 g, 2.26 mol) in glacial acetic acid (1.5 L) was added in three portions under vigorous stirring over a period of ~1 h. The temperature shot up to about 93° C. during the addition. The reaction mixture was maintained at 60-75° C. for 3 h. Additional zinc dust (221 g, 3.39 mol) was added to the reaction mass over 15 min and the mixture was stirred at 60-75° C. for 1 h, cooled to room temperature and filtered the solids. The filtrate was evaporated in vacuo and the residue was co-distilled with toluene (2×500 mL). Water (5 L) and ethyl acetate (1 L) were added to the residue and stirred till two clear layers were obtained. The organic layer washed successively with water (2×500 mL), saturated bicarbonate solution (2×500 mL), brine (2×500 mL) dried over anhydrous sodium sulfate and concentrated to give 360 g of crude gummy product. This was stirred with a mixture of dichloromethane in pet ether (200 mL: 1200 mL; 1:6) at room temperature for 15 min, filtered and washed with pet ether (100 mL) to afford 250 g (36%) of 5-methyl-3-phenyl-1H-pyrrole-2,4 dicarboxylic acid diethyl ester B as off-white solid. [TLC system: ethyl acetate:Pet ether (3:7); $R_f$ value:

0.45]. Similarly 1.5 Kg (500 g×3) of A was converted to 500 g [245 g (36%)+255 g (37%)+250 g (36%)] of B in three batches.

1,5-Dimethyl-3-phenyl-1H-pyrrole-2,4-dicarboxylic acid diethyl ester (C)

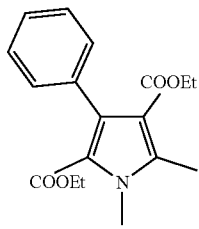 [SMILES: CCOC(=O)c1c(-c2ccccc2)c(C(=O)OCC)n(C)c1C]

A solution of B (1 Kg, 3.322 mol) in dry tetrahydrofuran (4 L) was added to slurry of sodium hydride (60% w/w; 254 g, 6.644 mol) in dry tetrahydrofuran (4 L) at 0° C. over 1 h. The reaction mass was warmed to room temperature and stirred for 1 h and again cooled to 0° C. Methyl iodide (517 mL; 8.305 mol) was added over 12 h and the reaction mixture stirred at room temperature for 18 h. Quenched with ice-water (100 mL) and 1N hydrochloric acid (2 L) was added. The organic layer was separated and the aqueous layer was extracted with dichloromethane (2×500 mL). The combined organic layers were washed successively with brine (2×200 mL), dried over anhydrous sodium sulfate and concentrated to dryness to afford 950 g (91%) of 1, 5-dimethyl-3-phenyl-1H-pyrrole-2, 4-dicarboxylic acid diethyl ester C as a yellow solid [TLC system: ethyl acetate:Pet ether (3:7); $R_f$ value: 0.56].

1, 5-Dimethyl-3-phenyl-1H-pyrrole-2,4-dicarboxylic acid (D)

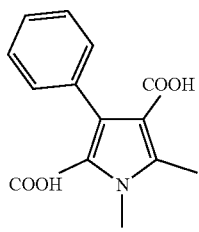 [SMILES: Cc1c(C(=O)O)c(-c2ccccc2)c(C(=O)O)n1C]

A solution of sodium hydroxide (1.21 Kg, 30.25 mol) in water (3.6 L) was added to a solution of C (950 g, 3.025 mol) in ethanol (5 L) and heated at reflux for 15 h. Ethanol was evaporated under reduced pressure, the residue was diluted with water (1 L) and chilled to 0° C. Concentrated hydrochloric acid (2 L) was slowly added to adjust pH to ~2, while maintaining temperature below 10° C. and stirred for 1 h. The precipitated solid was filtered, washed with water (1 L) and pet ether (1 L) and dried under vacuum at 60° C., to afford 550 g (70%) of 1,5-Dimethyl-3-phenyl-1H-pyrrole-2,4-dicarboxylic acid D as a white solid. [TLC system: ethyl acetate:Pet ether (3:7); $R_f$ value: 0.15].

1, 2-Dimethyl-4-phenyl-1H-pyrrole (E)

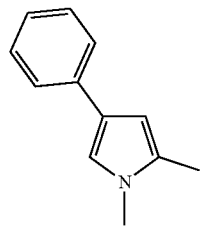

A suspension of E (550 g, 2.123 mol) in ethanolamine (1.5 L) was heated to 175° C. (under $N_2$) and maintained for 1 h. The reaction mixture was cooled to room temperature, diluted with water (500 mL) and extracted with ethyl acetate (3×200 mL). The combined organic layers were washed successively with water (2×100 mL) and brine (2×100 mL), dried over anhydrous sodium sulfate and concentrated in vacuo below 40° C. to give a crude product. Flash chromatography over neutral alumina using 5% ethyl acetate in pet ether as eluent afforded 280 g (77%) of 1,2-dimethyl-4-phenyl-1H-pyrrole E, as a white solid. [TLC system: ethyl acetate:Pet ether (3:7); $R_f$ value: 0.75].

(1, 5-Dimethyl-3-phenyl-1H-pyrrol-2-yl)-oxo-acetyl chloride (F)

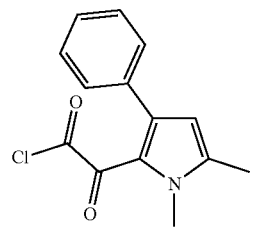 [SMILES: Cc1cc(-c2ccccc2)c(C(=O)C(=O)Cl)n1C]

Oxalyl chloride (116 mL, 1.286 mol) was added slowly to a cooled solution of E (250 g, 1.169 mol) in dry dichloromethane (3×200 mL) at 0° C. The reaction mixture was warmed to room temperature and stirred for 1 h. The solvent was evaporated to dryness in vacuo to afford 340 g (89%) of 1,5-dimethyl-3-phenyl-1H-pyrrol-2-yl)-oxo-acetyl chloride F as a brown oily liquid. [TLC system: ethyl acetate:Pet ether (3:7); $R_f$ value: 0.65]

4-Nitro Phenyl Piperazine (G)

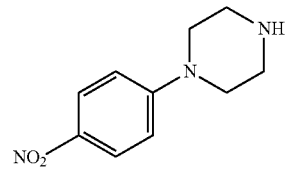 [SMILES: O=[N+]([O-])c1ccc(N2CCNCC2)cc1]

A solution of 1-chloro-4-nitro benzene (650 g, 4.140 mol) in diglyme (1 L) was added to a solution of piperazine (2.84 Kg, 33.12 mol) in diglyme (500 mL) at 100° C. and the resultant mass was stirred at 100° C. for 6 h. The mixture was cooled to 40-45° C., water (5 L) was added; warmed to room temperature and stirred for 1 h. The precipitated solid was filtered, washed with water (1 L), pet ether (500 mL) and dried to give 700 g (81%) of 4-nitro phenyl piperazine G as yellow colour solid. [TLC system: Ethyl acetate:pet ether (3:7); $R_f$ value: 0.70].

5-Fluoro-2-[4-(4-nitro-phenyl)-piperazin-1-yl]-pyrimidine (H)

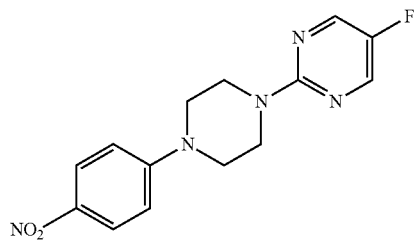 [SMILES: O=[N+]([O-])c1ccc(N2CCN(c3ncc(F)cn3)CC2)cc1]

2-Chloro-5-fluoropyrimidine (281 g, 2.12 mol) was added to suspension of 4-nitro phenyl piperazine G (400 g, 1.93 mol) and potassium carbonate (532 g, 3.85 mol) in diglyme (2.5 L), the resulting mixture was stirred at 100° C. for 6 h. On completion the mixture was cooled to 0° C. and filtered, the solid was taken in water (5 L) and stirred for 30 mins. The suspension was filtered, the solid cake was washed with water (1 L), pet ether (1 L) and dried under vacuum to afford 500 g (85%) of 5-fluoro-2-[4-(4-nitro-phenyl)-piperazin-1-yl]-pyrimidine H as yellow colour solid. [TLC system: Ethyl acetate:pet ether (3:7); $R_f$ value: 0.70].

4-[4-(5-Fluoro-pyrimidin-2-yl)-piperazin-1-yl]-phenyl amine (I)

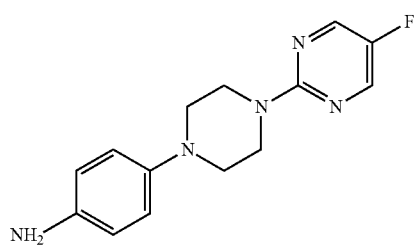 [SMILES: Nc1ccc(N2CCN(c3ncc(F)cn3)CC2)cc1]

A solution of sodium dithionite (1.27 Kg, 7.32 mol) in water (6 L) was added to a suspension of H (500 g, 1.83 mol) and sodium bicarbonate (614 g, 7.32 mol) in methanol (6 L) at 65° C. The resultant mixture was stirred at 65° C. for 2 h. The reaction mass was cooled to 10-15° C. and filtered. The residue was partitioned between water (2 L) and ethyl acetate (5 L), the organic layer was washed with water (2 L), brine (2 L) and dried over anhydrous sodium sulfate. Concentrated in vacuo to afford 290 g (64%) of 4-[4-(5-fluoro-pyrimidin-2-yl)-piperazin-1-yl]-phenyl amine I as solid. [TLC system: Methanol:Chloroform (1:9); $R_f$ value: 0.50].

2-(1,5-Dimethyl-3-phenyl-1H-pyrro-2-yl)-N-{4-[4-(5-fluoro-pyrimidin-2-yl)-piperazin-1-yl]-phenyl}-2-oxo-acetamide

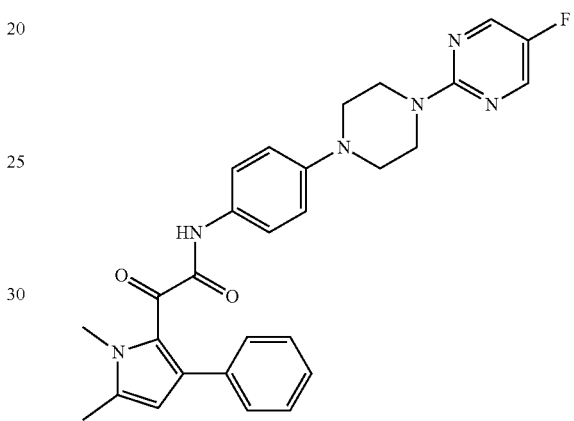

A solution of F (332 g, 1.27 mol) in dichloromethane (3 L) was added to a stirred solution of I (290 g, 1.06 mol) and triethylamine (294 mL, 2.12 mol) in dichloromethane (3 L) at 0° C. The reaction mixture was warmed to room temperature and stirred for 30 min. The reaction mixture was quenched with water and extracted with dichloromethane (6×500 mL). The combined organic layers were washed successively with saturated sodium bicarbonate solution (1.5 L), water (1 L), brine (1.5 L) and finally dried over anhydrous sodium sulfate. The organic layer was stirred with neutral alumina (1 Kg) at room temperature for 30 min and filtered. The filtrate was concentrated in vacuo to give the crude compound which on washing with diethyl ether (300 mL) and followed by trituration with ethanol (3 L) at 80° C. for 1 h and cooled to room temperature, filtered, washed with ethanol (500 mL) followed by hexane (200 mL) and dried to give 340 g (64%) of 2-(1,5-dimethyl-3-phenyl-1H-pyrro-2-yl)-N-{4-[4-(5-fluoro-pyrimidin-2-yl-piperazin-1yl]-phenyl}-2-oxo-acetamide as yellow color solid. [TLC System: Ethyl acetate:Pet ether (1:1); $R_f$ value: 0.65].

NMR data for 2-(1, 5-Dimethyl-3-phenyl-1H-pyrro-2-yl)-N-{4-[4-(5-fluoro-pyrimidin-2-yl)-piperazin-1-yl]-phenyl}-2-oxo-acetamide ($^1$H NMR (400 MHz, CDCl$_3$)) are provided in FIG. 1. The signal was detected in the MS spectrum at 499.1 [M+H]$^+$.

2. Synthesis of Example 2: 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide

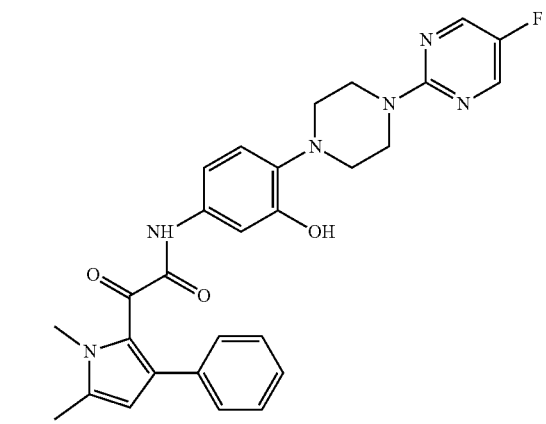 [SMILES: Cc1cc(-c2ccccc2)c(C(=O)C(=O)Nc2ccc(N3CCN(c4ncc(F)cn4)CC3)c(O)c2)n1C]

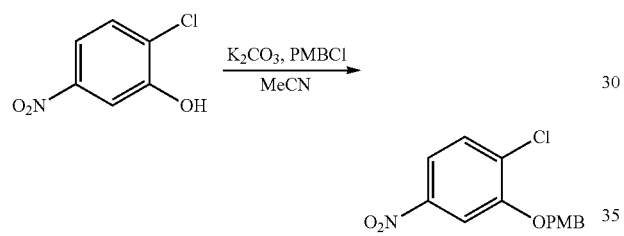

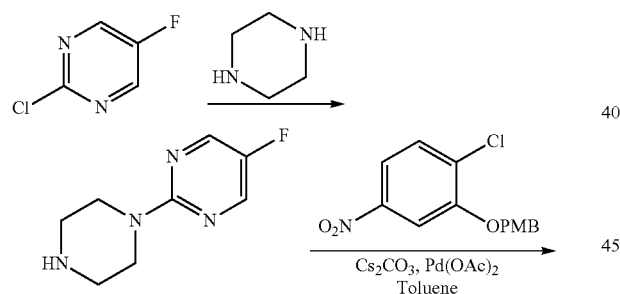

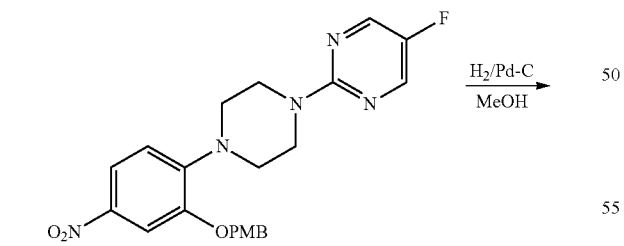

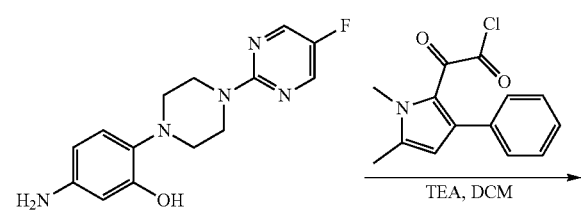

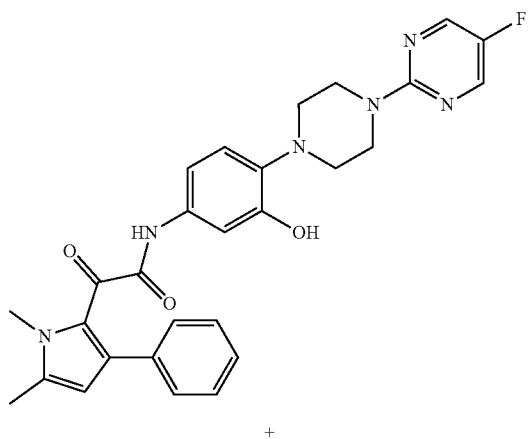

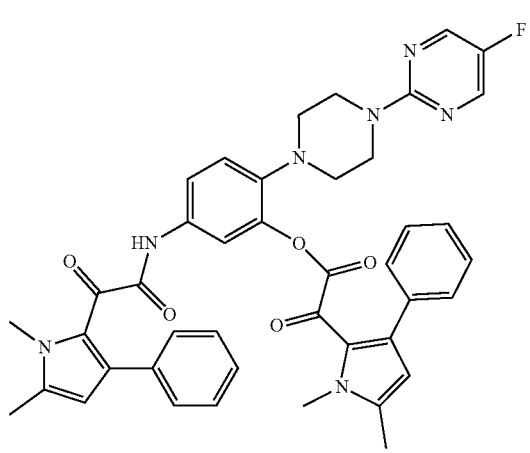 [SMILES: Cc1cc(-c2ccccc2)c(C(=O)C(=O)Nc2ccc(N3CCN(c4ncc(F)cn4)CC3)c(OC(=O)C(=O)c3c(-c4ccccc4)cc(C)n3C)c2)n1C]

2-Fluoro-5-(piperazin-1-yl) pyrimidine (K)

5-chloro-2-fluoropyrimidine (3.0 g, 22.64 mmol) was added to piperazine (9.73 g, 113.2 mmol) at room temperature. The resultant mixture was heated to 130° C. for 4 h. The reaction mixture was cooled to room temperature, quenched with water, extracted with dichloromethane. The combined organic layer was washed with water, brine, dried over sodium sulfate and concentrated under vacuum to give the 3.5 g (85%) of 2-fluoro-5-(piperazin-1-yl) pyrimidine K as solid. [TLC system: Methanol:Dichloromethane (1:9); $R_f$ value: 0.21].

1-Chloro-2-(4-methoxybenzyloxy)-4-nitrobenzene (J)

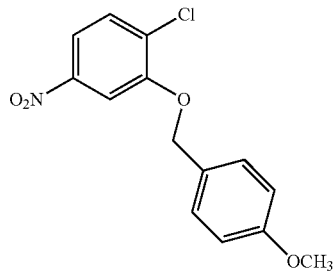 [SMILES: COc1ccc(COc2cc([N+](=O)[O-])ccc2Cl)cc1]

4-Methoxylbenzyl chloride (2.69 g, 17.29 mmol) was added to a stirred suspension of 2-chloro-5-nitrophenol (3.0 g, 17.29 mmol) and potassium carbonate (7.16 g, 51.87 mmol) in acetonitrile (30 mL) at room temperature. The resultant mixture was heated to 80° C. for 12 h. The reaction mixture was cooled to room temperature, quenched with water, extracted with ethyl acetate. The organic layer was washed with water, brine, dried over anhydrous sodium sulfate and concentrated under vacuum to give 4.0 g (80%) of 1-chloro-2-(4-methoxybenzyloxy)-4-nitrobenzene J as solid [TLC system: Ethyl acetate:Pet ether (2:8); $R_f$ value: 0.71].

5-Fluoro-2-(4-(2-(4-methoxybenzyloxy)-4-nitrophenyl)piperazin-1-yl) pyrimidine L

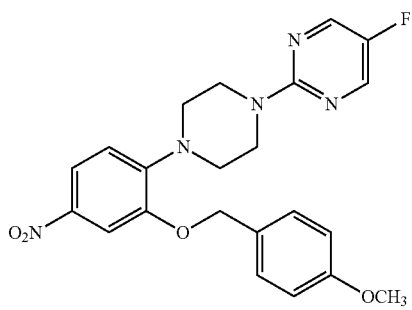 [SMILES: COc1ccc(COc2cc([N+](=O)[O-])ccc2N2CCN(c3ncc(F)cn3)CC2)cc1]

Cesium carbonate (23.35 g, 71.67 mmol) was added to a stirred solution of 1-chloro-2-(4-methoxybenzyloxy)-4-nitrobenzene J (3.5 g, 11.94 mmol) and 2-fluoro-5-(piperazin-1-yl) pyrimidine K (2.17 g, 11.94 mmol) in toluene (40 mL) at room temperature. The suspension was purged with argon for 20 minutes. Then 2'-(dicyclohexylphosphino)-N,N-dimethylbiphenyl-2-amine (0.47 g, 1.19 mmol), palladium acetate (0.806 g, 1.19 mmol) was added to the degasified mixture, then purged with argon another 10 minutes. The resultant mixture was heated to 120° C. for 12 h. The reaction mixture was cooled to room temperature, quenched with water, extracted with ethyl acetate. The organic layer was washed with water, brine, dried over sodium sulfate and concentrated under vacuo to give the crude compound. Purification by column chromatography over silica gel (100-200 mesh) using 20-25% ethyl acetate in pet ether as eluent afforded 4.2 g (80%) of 5-fluoro-2-(4-(2-(4-methoxybenzyloxy)-4-nitrophenyl) piperazin-1-yl) pyrimidine L as yellow color solid. [TLC system: Ethyl acetate:Pet ether (1:1); $R_f$ value: 0.55].

5-Amino-2-(4-(5-fluoropyrimidin-2-yl)piperazin-1-yl)phenol M

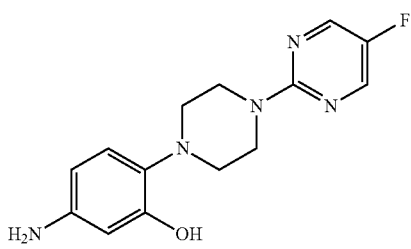 [SMILES: Nc1ccc(N2CCN(c3ncc(F)cn3)CC2)c(O)c1]

10% palladium on carbon (0.2 g) was added to a solution of 5-fluoro-2-(4-(2-(4-methoxybenzyloxy)-4-nitrophenyl) piperazin-1-yl) pyrimidine L (4 g, 9.11 mmol) in methanol (20 mL) at room temperature. The resultant mixture was hydrogenated in Parr hydrogenator under 40 psi pressure at room temperature for 3 h. The reaction mixture was filtered over celite and the filtrate was concentrated in vacuo to afford 1.5 g (56.9%) of 5-amino-2-(4-(5-fluoropyrimidin-2-yl)piperazin-1-yl)phenol M solid. [TLC system: Ethyl acetate:Pet ether (1:1); $R_f$ value: 0.40].

2-(1,5-Dimethyl-3-phenyl-1H-pyrrol-2-yl)-N-(4-(4-(5-fluoropyrimidin-2-yl)piperazin-1-yl)-3-hydroxyphenyl)-2-oxoacetamide (Example 2) and 5-(2-(1,5-Dimethyl-3-phenyl-1H-pyrrol-2-yl)-2-oxoacetamido)-2-(4-(5-fluoropyrimidin-2-yl)piperazin-1-yl) phenyl 2-(1,4-dimethyl-3-phenyl-1H-pyrrol-2-yl)-2-oxoacetate (Example 2')

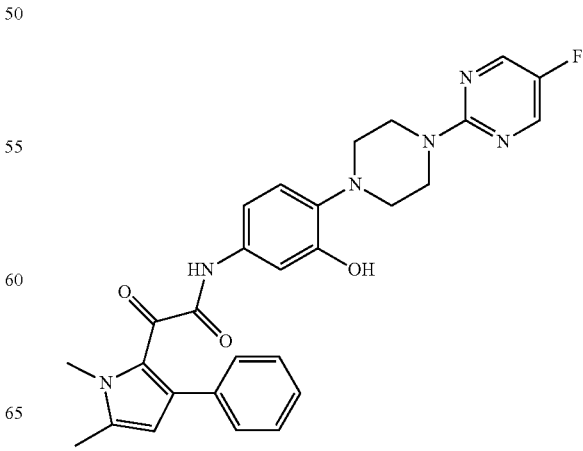

-continued

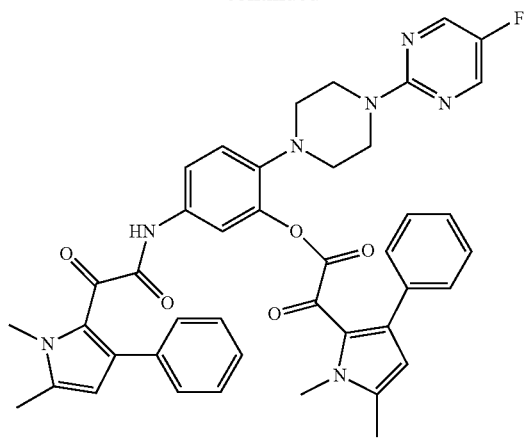

A solution of F (1.5 g, 5.81 mmol) in dichloromethane (5 mL) was added slowly to stirred solution of 5-amino-2-(4-(5-fluoropyrimidin-2-yl)piperazin-1-yl) phenol M (1.4 g, 4.84 mmol) and triethylamine (1046 g, 14.52 mmol) in dichloromethane at −60° C. for 30 min. The resultant mixture was stirred for 30 minutes at −60° C. The reaction mixture was quenched with water extracted with dichloromethane. The organic layer was washed with water, brine, dried over anhydrous sodium sulfate and concentrated under reduced pressure to give the crude compound, which was purified by column chromatography over silica gel (100-200 mesh) using 25-75% ethyl acetate in pet ether as eluent to afford 0.557 g (22%) of 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide Example 2 and 10 mg of 5-(2-(1,5-dimethyl-3-phenyl-1H-pyrrol-2-yl)-2-oxoacetamido)-2-(4-(5-fluoropyrimidin-2-yl)piperazin-1-yl)phenyl2-(1,4-dimethyl-3-phenyl-1H-pyrrol-2-yl)-2-oxoacetate Example 2' as solid [TLC system: Ethyl acetate:Pet ether (1:1); $R_f$ value: 0.32].

NMR data for 2-(1,5-Dimethyl-3-phenyl-1H-pyrrol-2-yl)-N-(4-(4-(5-fluoropyrimidin-2-yl)piperazin-1-yl)-3-hydroxyphenyl)-2-oxoacetamide ($^1$H NMR (400 MHz, CDCl$_3$)) are provided in FIG. 2. The signal was detected in the MS spectrum at 515.3 [M+H]$^+$.

NMR data for 5-(2-(1, 5-Dimethyl-3-phenyl-1H-pyrrol-2-yl)-2-oxoacetamido)-2-(4-(5-fluoropyrimidin-2-yl)piperazin-1-yl)phenyl 2-(1,4-dimethyl-3-phenyl-1H-pyrrol-2-yl)-2-oxoacetate ($^1$H NMR (400 MHz, CDCl$_3$)) are provided in FIG. 2b. The signal was detected in the MS spectrum at 740.43 [M+H]$^+$.

3. Synthesis of Deuterated Derivative

Example 3: 2-(1,5-dimethyl-3-phenyl-1H-pyrrol-2-yl)-N-(4-(4-(5-fluoropyrimidin-2-yl)piperazin-1-yl-2,2,3,3,5,5,6,6-d$_8$)phenyl)-2-oxoacetamide

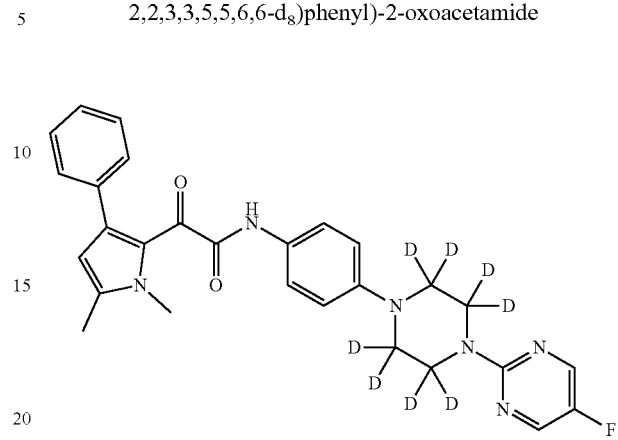

Synthesis of Compound (N)

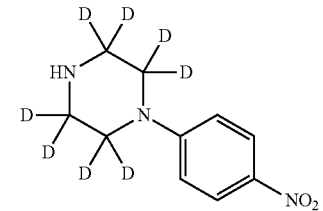 [SMILES: [2H]C1([2H])NC([2H])([2H])C([2H])([2H])N(c2ccc([N+](=O)[O-])cc2)C1([2H])[2H]]

A solution of 1-chloro-4-nitro benzene (750 mg, 4.7 mmol) in diglyme (5 mL) was added to a solution of piperazine-d$_8$ (2.71 g, 28.7 mmol) in diglyme (5 mL) at 100° C. and the resultant mass was stirred at 100° C. for 6 h. The mixture was cooled to 40-45° C., water (50 mL) was added; warmed to room temperature and stirred for 1 h. The precipitated solid was filtered, washed with water (50 mL), pet ether (50 mL) and dried to give 800 mg (80%) of N as yellow colour solid. [TLC system: Ethyl acetate:pet ether (3:7); $R_f$ value: 0.70].

Synthesis of Compound (P)

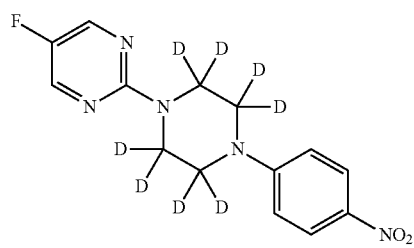

2-Chloro-5-fluoropyrimidine (541 mg, 4.0 mmol) was added to suspension of N (800 mg, 3.72 mmol) and potassium carbonate (1.0 g, 7.44 mmol) in diglyme (15 mL), the resulting mixture was stirred at 100° C. for 6 h. On completion the mixture was cooled to 0° C. and filtered, the solid was taken in water (50 mL) and stirred for 30 mins. The suspension was filtered, the solid cake was washed with water (50 mL), pet ether (15 mL) and dried under vacuum to afford 1.0 g (86%) of P as yellow color solid. [TLC system: Ethyl acetate:pet ether (3:7); $R_f$ value: 0.70].

Synthesis of Compound (Q)

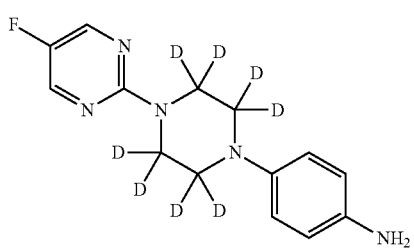 [SMILES: [2H]C1([2H])N(c2ccc(N)cc2)C([2H])([2H])C([2H])([2H])N(c2ncc(F)cn2)C1([2H])[2H]]

A solution of sodium dithionite (2.24 gm, 12.8 mmol) in water (15 mL) was added to a suspension of P (1.0 gm 3.21 mmol) and sodium bicarbonate (1.088 g, 12.8 mmol) in methanol (20 mL) at 65° C. The resultant mixture was stirred at 65° C. for 2 h. The reaction mass was cooled to 10-15° C. and filtered. The residue was partitioned between water (30 mL) and ethyl acetate (20 mL), the organic layer was washed with water (50 mL), brine (30 mL) and dried over anhydrous sodium sulfate. Concentrated in vacuo to afford 800 mg (88%) of Q as white solid. [TLC system: Methanol:Chloroform (1:9); $R_f$ value: 0.50].

Synthesis of Deuterated Derivative

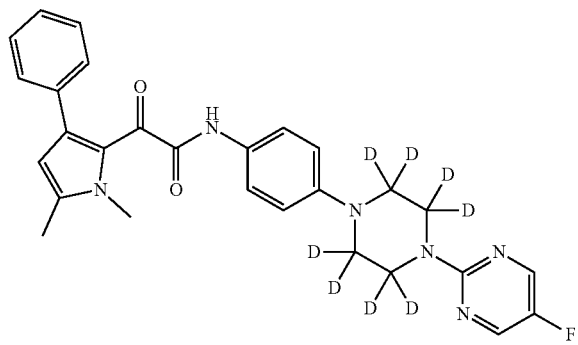 [SMILES: [2H]C1([2H])N(c2ccc(NC(=O)C(=O)c3c(-c4ccccc4)cc(C)n3C)cc2)C([2H])([2H])C([2H])([2H])N(c2ncc(F)cn2)C1([2H])[2H]]

A solution of Q (826 mg, 35.6 mmol) in dichloromethane (20 mL) was added to a stirred solution of F (750 mg, 26.6 mmol) and triethylamine (0.750 mL, 53.3 mmol) in dichloromethane (10 mL) at 0° C. The reaction mixture was warmed to room temperature and stirred for 30 min. The reaction mixture was quenched with water and extracted with dichloromethane (6×30 mL). The combined organic layers were washed successively with saturated sodium bicarbonate solution (50 mL), water (50 mL), brine (50 mL) and finally dried over anhydrous sodium sulfate. The organic layer was stirred with neutral alumina (100 g) at room temperature for 30 min and filtered. The filtrate was concentrated in vacuo to give the crude compound which on washing with diethyl ether (30 mL) and followed by trituration with ethanol (20 mL) at 80° C. for 1 h and cooled to room temperature, filtered, washed with ethanol (10 mL) followed by hexane (20 mL) and dried to give 430 mg (89%) of the deuterated derivative as yellow color solid. [TLC System: Ethyl acetate:Pet ether (1:1); $R_f$ value: 0.65].

NMR data for 2-(1,5-dimethyl-3-phenyl-1H-pyrrol-2-yl)-N-(4-(4-(5-fluoropyrimidin-2-yl)piperazin-1-yl-2,2,3,3,5,5,6,6-$d_8$)phenyl)-2-oxoacetamide ($^1$H NMR (400 MHz, CDCl$_3$)) are provided in FIG. 3. The signal was detected in the MS spectrum at 507.5 [M+H]$^+$.

4. Synthesis of Deuterated Derivative

Example 4: 2-(1,5-dimethyl-3-phenyl-1H-pyrrol-2-yl)-N-(4-(4-(5-fluoropyrimidin-2-yl)piperazin-1-yl)phenyl-2,3,5,6-$d_4$)-2-oxoacetamide

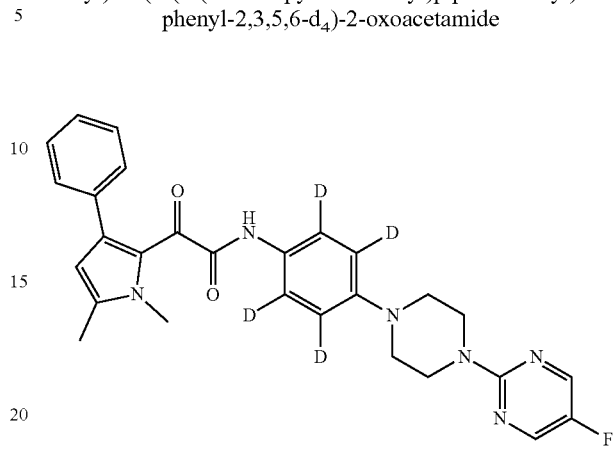

Synthesis of Compound (R)

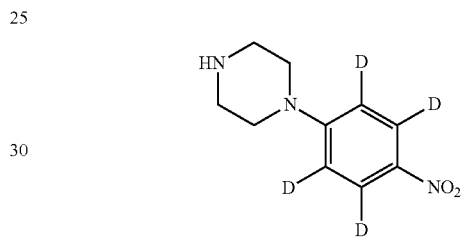

A solution of 1-chloro-4-nitro benzene-$d_4$ (2.0 g, 12.4 mmol) in diglyme (15 mL) was added to a solution of piperazine (8.5 g, 99.3 mmol) in diglyme (15 mLL) at 100° C. and the resultant mass was stirred at 100° C. for 6 h. The mixture was cooled to 40-45° C., water (50 mL) was added; warmed to room temperature and stirred for 1 h. The precipitated solid was filtered, washed with water (50 mL), pet ether (50 mL) and dried to give 2.0 g (80%) of R as yellow color solid. [TLC system: Ethyl acetate:pet ether (3:7); $R_f$ value: 0.70].

Synthesis of Compound (S)

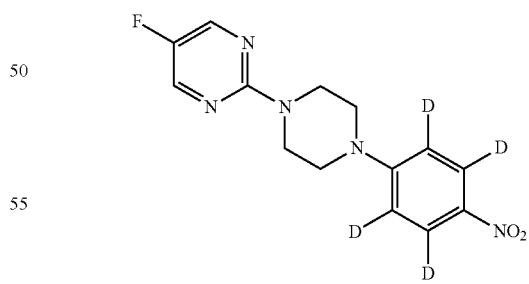

2-Chloro-5-fluoropyrimidine (1.44 g, 10.9 mmol) was added to suspension of R (2.1 g, 99.5 mmol) and potassium carbonate (2.7 g, 19.8 mmol) in diglyme (15 mL), the resulting mixture was stirred at 100° C. for 6 h. On completion the mixture was cooled to 0° C. and filtered, the solid was taken in water (100 mL) and stirred for 30 min. The suspension was filtered; the solid cake was washed with water (50 mL), pet ether (50 mL) and dried under vacuum to afford 2.9 g (94%) of S as yellow color solid. [TLC system: Ethyl acetate:pet ether (3:7); $R_f$ value: 0.70].

Synthesis of Compound (T)

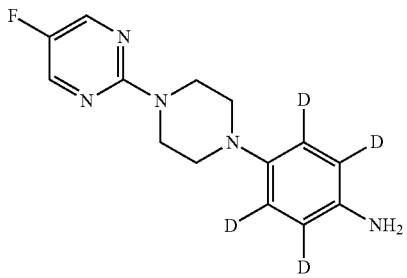 [SMILES: [2H]c1c([2H])c([N+](=O)[O-])c([2H])c([2H])c1N1CCN(c2ncc(F)cn2)CC1]

A solution of sodium dithionite (4.52 g, 26 mmol) in water (20 mL) was added to a suspension of S (2.0 gm 65 mmol) and sodium bicarbonate (2.21 g, 26 mmol) in methanol (20 mL) at 65° C. The resultant mixture was stirred at 65° C. for 2 h. The reaction mass was cooled to 10-15° C. and filtered. The residue was partitioned between water (30 mL) and ethyl acetate (20 mL), the organic layer was washed with water (50 mL), brine (30 mL) and dried over anhydrous sodium sulfate. Concentrated in vacuo to afford 1.5 g (83%) of T as white solid. [TLC system: Methanol:Chloroform (1:9); $R_f$ value: 0.50].

Synthesis of Deuterated Derivative

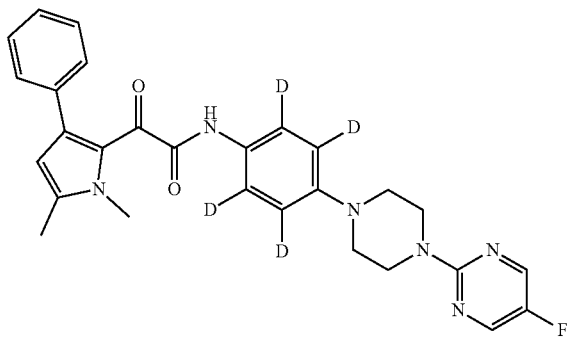 [SMILES: [2H]c1c([2H])c(N2CCN(c3ncc(F)cn3)CC2)c([2H])c([2H])c1NC(=O)C(=O)c1c(-c2ccccc2)cc(C)n1C]

A solution of T (715 mg, 26.9 mmol) in dichloromethane (20 mL) was added to a stirred solution of F (835 mg, 32 mmol) and triethylamine (0.750 mL, 53.3 mmol) in dichloromethane (10 mL) at 0° C. The reaction mixture was warmed to room temperature and stirred for 30 min. The reaction mixture was quenched with water and extracted with dichloromethane (6×30 mL). The combined organic layers were washed successively with saturated sodium bicarbonate solution (50 mL), water (50 mL), brine (50 mL) and finally dried over anhydrous sodium sulfate. The organic layer was stirred with neutral alumina (100 g) at room temperature for 30 min and filtered. The filtrate was concentrated in vacuo to give the crude compound. Crude compound was purified by Perp. HPLC to give 430 mg (89%) of the deuterated derivative as yellow color solid. [TLC System: Ethyl acetate:Pet ether (1:1); $R_f$ value: 0.65].

Figure 4:
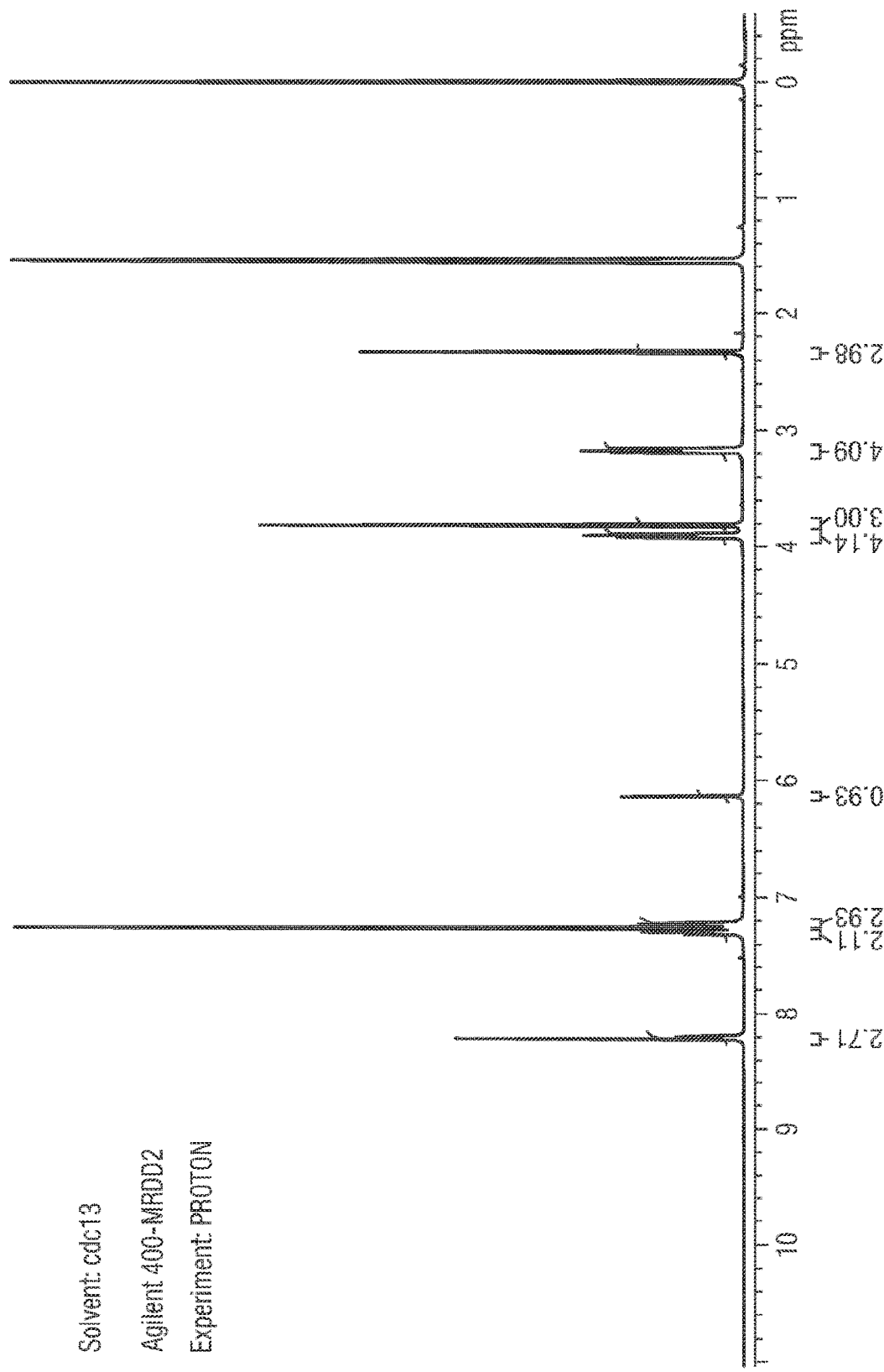
FIG. 4 provides NMR data for 2-(1,5-dimethyl-3-phenyl-1H-pyrrol-2-yl)-N-(4-(4-(5-fluoropyrimidin-2-yl)piperazin-1-yl)phenyl-2,3,5,6-d$_4$)-2-oxoacetamide ($^1$H NMR (400 MHz, CDCl$_3$)).

NMR data for 2-(1,5-dimethyl-3-phenyl-1H-pyrrol-2-yl)-N-(4-(4-(5-fluoropyrimidin-2-yl)piperazin-1-yl)phenyl-2,3,5,6-$d_4$)-2-oxoacetamide ($^1$H NMR (400 MHz, CDCl$_3$)) are provided in FIG. 4. The signal was detected in the MS spectrum at 503.4 [M+H]$^+$.

REFERENCE EXAMPLES

Data demonstrating that 2-(1,5-dimethyl-3-phenyl-1H-pyrrol-2-yl)-N-(4-(4-(5-fluoropyrimidin-2-yl)piperazin-1-yl)phenyl)-2-oxoacetamide inhibits the growth of a wide variety of fungi are presented below. A comparison between this pyrrole compound and structurally similar compounds is also provided. The compounds are:

Example 1: 2-(1,5-dimethyl-3-phenyl-1H-pyrrol-2-yl)-N-(4-(4-(5-fluoropyrimidin-2-yl)piperazin-1-yl)phenyl)-2-oxoacetamide.

Reference Example 1: 2-(1,5-Dimethyl-3-phenyl-1H-pyrrol-2-yl)-N-[3-fluoro-4-(4-pyridin-2-yl-piperazin-1-yl)-phenyl]-2-oxo-acetamide.

Example 2: 2-(1,5-dimethyl-3-phenyl-1H-pyrrol-2-yl)-N-(4-(4-(5-fluoropyrimidin-2-yl)piperazin-1-yl)-3-hydroxyphenyl)-2-oxoacetamide Example 3: 2-(1,5-dimethyl-3-phenyl-1H-pyrrol-2-yl)-N-(4-(4-(5-fluoropyrimidin-2-yl)piperazin-1-yl-2,2,3,3,5,5,6,6-$d_8$)phenyl)-2-oxoacetamide Example 4: 2-(1,5-dimethyl-3-phenyl-1H-pyrrol-2-yl)-N-(4-(4-(5-fluoropyrimidin-2-yl)piperazin-1-yl)phenyl-2,3,5,6-$d_4$)-2-oxoacetamide Reference Example 2: 2-(1,5-Dimethyl-3-phenyl-1H-pyrrol-2-yl)-N-[2-fluoro-4-(4-pyridin-2-yl-piperazin-1-yl)-phenyl]-2-oxo-acetamide.

Reference Example 3: 2-(1,5-Dimethyl-3-phenyl-1H-pyrrol-2-yl)-N-{4-[4-(4,6-dimethyl-pyridin-2-yl)-piperazin-1-yl]-3-methyl-phenyl}-2-oxo-acetamide.

Reference Example 4: 2-(1,5-Dimethyl-3-phenyl-1H-pyrrol-2-yl)-N-{4-[4-(4-methyl-pyridin-2-yl)-piperazin-1-yl]-phenyl}-2-oxo-acetamide.

Reference Example 5: 2-(1,5-Dimethyl-3-phenyl-1H-pyrrol-2-yl)-N-{4-[4-(6-methyl-pyridin-2-yl)-piperazin-1-yl]-phenyl}-2-oxo-acetamide.

Reference Example 6: 2-(1,5-Dimethyl-3-phenyl-1H-pyrrol-2-yl)-2-oxo-N-[4-(4-pyridin-2-yl-piperazin-1-yl)-phenyl]-acetamide.

Reference Example 7: 2-(1,5-Dimethyl-3-phenyl-1H-pyrrol-2-yl)-N-{4-[4-(4,6-dimethyl-pyridin-2-yl)-piperazin-1-yl]-3-hydroxy-phenyl}-2-oxo-acetamide.

Reference Example 8: N-{2-Chloro-4-[4-(4,6-dimethyl-pyridin-2-yl)-piperazin-1-yl]-phenyl}-2-(1,5-dimethyl-3-phenyl-1H-pyrrol-2-yl)-2-oxo-acetamide.

Reference Example 9: N-{3-Chloro-4-[4-(4,6-dimethyl-pyridin-2-yl)-piperazin-1-yl]-phenyl}-2-(1,5-dimethyl-3-phenyl-1H-pyrrol-2-yl)-2-oxo-acetamide.

Reference Example 10: 2-(1,5-Dimethyl-3-phenyl-1H-pyrrol-2-yl)-N-{4-[4-(4,6-dimethyl-pyridin-2-yl)-piperazin-1-yl]-phenyl}-2-oxo-acetamide.

The synthesis of reference examples 1 to 10 is described in WO 2009 130481, in the Examples section of the WO 2009 130481 specification. Information relating to the synthesis of the reference examples is incorporated herein by reference.

Activity Example: Measurement of Minimum Inhibitory Concentrations (MICs)

2-(1,5-dimethyl-3-phenyl-1H-pyrro-2-yl)-N-{4-[4-(5-fluoro-pyrimidin-2-yl-piperazin-1yl]-phenyl}-2-oxo-acetamide Between 1 and 5 mgs of the compound were accurately weighed out into a sterile Eppendorf tube. The compound was dissolved in DMSO to give a solution containing 5 mg/mL. Tubes were stored at −20° C. until required.

On the day of testing thawed solutions were vortex mixed to ensure homogeneity. 30 µL of solution was removed and added to 570 µL of sterile water in a separate sterile Eppendorf. The thoroughly mixed solution was used to prepare a series of doubling dilutions in water, in a deep well plate. Thirteen replicate plates were prepared using a Minitrak by aspirating 20 µL from each well into eleven clear polystyrene 96 well plates.

Spores of *Aspergillus* and *Scedosporium* were harvested from cultures grown on Sabarauds agar for 5 days, and resuspended in PBS/Tween 80 to approx $1 \times 10^7$ cfu/mL. Each organism suspension was diluted in RPMI medium, containing 2% glucose and 0.135 M MOPS buffer (pH 7.0) to $0.5-2 \times 10^4$ cfu/mL. 80 µL of an organism suspension was added to each well of the plate containing drug dilutions.

This produced MIC plates with a drug range 50-0.05 mg/L and organism inocula of $1-2 \times 10^4$ cfu/mL. All plates were incubated for 24-48 h at 35° C. Growth was assessed by monitoring the optical density at 485 nm for each well. The MIC of a compound is the lowest drug concentration that inhibits growth of an organism by >80% compared with a drug free control.

The following organisms were tested: *Aspergillus niger*, *Aspergillus fumigates*, *Aspergillus terreus*, *Aspergillus flavus*, *Aspergillus terreus* 49, *Aspergillus fumigatus* 210, *Scedosporium apiospermum* 13486, *Scedosporium apiospermum* 15848, *Scedosporium apiospermum* 451, *Scedosporium apiospermum* 4883, *Scedosporium apiospermum* 7935, *Scedosporium apiospermum* 8353, *Scedosporium prolificans* 18389, *Scedosporium prolificans* 206, *Scedosporium prolificans* 6322, *Scedosporium species* 15849, *Scedosporium apiospermum* 13486, *Scedosporium prolifican* 201, *Scedosporium prolifican* 13486, *Scedosporium prolifican* 7935, *Scedosporium prolifican* 15848, *Scedosporium prolifican* 8353, *Scedosporium prolifican* 451, *Scedosporium prolifican* 4883, *Scedosporium prolifican* 15849, *Scedosporium prolifican* 1121 and *Scedo apiospermum* 1124.

Other fungi including *Absidia corymbifera*; *Acremonium* spp; *Alternaria alternata*; *Aspergillus nidulans*; *Aspergillus parasiticus*; *Bipolaris* spp; *Blastomyces dermatitidis*, *Blumeria graminis*; *Cladosporium herbarium*; *Coccidioides immitis*; *Coccidioides posadasii*; *Colletotrichium trifolii*; *Curvularia lunata*; *Colletotrichium trifolii*; *Cryptococcus neoformans*; *Encephalitozoon cuniculi*; *Epicoccum nigrum*; *Epidermophyton floccosum*; *Exophiala* spp; *Exserohilum rostratum*; *Fusarium graminearium*; *Fusarium solani*; *Fusarium sporotrichoides*; *Histoplasma capsulatum*; *Leptosphaeria nodorum*; *Magnaporthe grisea*; *Microsporum canis*; *Mycosphaerella graminicola*; *Neurospora crassa*; *Paecilomyces lilanicus*; *Paecilomyces varioti*; *Penicillium chrysogenum*; *Phytophthora capsici*; *Phytophthora infestans*; *Plasmopara viticola*; *Pneumocystis jiroveci*; *Puccinia coronata*; *Puccinia graminis*; *Pyricularia oryzae*; *Pythium ultimum*; *Rhizomucor* sp.; *Rhizoctonia solani*; *Rhizomucor* spp.; *Rhizopus* spp.; *Scopulariopsis brevicaulis*; *Trichophyton interdigitale*; *Trichophyton mentagrophytes*; *Trichophyton rubrum*; *Trichosporon asahii*; *Trichosporon beigelii*; and *Ustilago maydis* may also be used in the above assay. Fungi are cultured by standard methods known to those skilled in the art, and MICs determined as above.

*Aspergillus* MIC Results in Mg/L (RPMI Medium):

The following MIC results have been banded into grades. Thus, a grade of F represents an MIC of greater than 0.06 mg/L. A grade of E represents an MIC of greater than 0.04 mg/L but less than or equal to 0.06 mg/L. A grade of D represents an MIC of greater than 0.02 mg/L but less than or equal to 0.04 mg/L. A grade of C represents an MIC of greater than 0.01 mg/L but less than or equal to 0.02 mg/L. A grade of B represents an MIC of greater than 0.005 mg/L but less than or equal to 0.01 mg/L. A grade of A represents an MIC of less than or equal to 0.005 mg/L.

| Example no. | A. niger | A. fumigatus | A. terreus | A. flavus | A. terreus 49 | A. fumigatus 210 |
|---|---|---|---|---|---|---|
| Example 1 | C | C | A | B | A | C |
| Example 3 | E | E | E | E | E | E |
| Example 4 | E | E | E | E | E | E |
| Ref. Example 1 | E | E | E | F | E | E |
| Ref. Example 2 | E | E | E | E | E | E |
| Ref. Example 3 | E | E | E | E | E | E |
| Ref. Example 4 | E | E | E | E | E | E |
| Ref. Example 5 | F | E | E | E | E | E |
| Ref. Example 6 | F | E | E | E | E | E |
| Ref. Example 7 | F | F | F | E | F | F |
| Ref. Example 8 | E | E | E | E | E | E |
| Ref. Example 9 | E | E | E | E | E | E |
| Ref. Example 10 | F | D | D | E | D | D |

*Scedosporium* MIC Results in Mg/L (RPMI Medium):

The following MIC results have been banded into grades as defined above.

| Example no. | Scedosporium apiospermum 13486 | Scedosporium apiospermum 15848 | Scedosporium apiospermum 451 | Scedosporium apiospermum 4883 | Scedosporium apiospermum 7935 | Scedosporium apiospermum 8353 | Scedosporium prolificans 18389 | Scedosporium prolificans 206 | Scedosporium prolificans 6322 | Scedosporium species 15849 | Scedosporium apiospermum 13486 |
|---|---|---|---|---|---|---|---|---|---|---|---|
| Example 1 | D | D | B | C | C | B | C | D | D | E | D |
| Ref Example 6 | F | F | F | F | F | F | F | F | F | F | F |
| Ref Example 10 | F | F | F | D | F | E | F | F | E | F | F |

| Example no. | Scedosporium prolifican 201 | Scedosporium prolifican 13486 | Scedosporium prolifican 7935 | Scedosporium prolifican 15848 | Scedosporium prolifican 8353 | Scedosporium prolifican 451 | Scedosporium prolifican 4883 | Scedosporium prolifican 15849 | Scedosporium prolifican 1121 | Scedos apiospermum 1124 |
|---|---|---|---|---|---|---|---|---|---|---|
| Example 1 | D | D | C | D | B | B | C | E | A | A |

Analogous MIC experiments to those described above showed that the compound of Example 1 showed also good antifungal activity against *S. dehoogii*, *S. boydii* and *S. aurantiacum*.

In Vivo Testing Example

Summary of Survival Models of *Aspergillus fumigatus* Infection

Murine survival models are frequently used to assess the efficacy of antifungal drugs against *Aspergillus*. The models used in the development of Example 1 were carried out at Euprotec Ltd (Manchester) a contract research organisation (CRO) with extensive experience in the evaluation of antifungal drugs. The typical model involves the use of groups of 6-10 male CD-1 mice per treatment group. Mice are immunosuppressed with 200 mg/kg cyclophosphamide injected intraperitoneal 3 days prior to infection. *A. fumigatus* strain A1163 is cultured on Sabourauds agar for 4-6 days at 35° C. Spores are harvested in phosphate buffered saline (PBS)/Tween, the suspension diluted and the number of spores enumerated. Mice are then infected with an intravenous injection of *A. fumigatus* spores given through the lateral tail vein. The typical inoculum is $6-8 \times 10^4$ cfu/mouse and is sufficient to kill all untreated animals by Day 4-6. The animals die of IA and *Aspergillus* organisms can be detected in many body tissues. Treatment is typically commenced soon after infection but delays of up to 24 h following infection produce a more challenging model. Treatment is continued for 7-9 days. Treatment may be up to 3 times daily using an oral dosing. Following cessation of treatment, animals are observed for 1-2 days, and then sacrificed. Relevant controls treated with oral drug-free vehicle are always included; ideally there should be no survivors in this group. A positive control consisting of an antifungal drug such as Reference Example 10 was used. This compound consistently produces 100% survival at doses of 10 mg/kg b.i.d. dosed by the oral route. Most models are run as temporary neutropenic models where only a single dose of cyclophosphamide is administered.

The fungal burden in the kidney can be determined on animals surviving to the end of the study and this can help provide efficacy discrimination between groups where all animals survive. Tissue burdens are carried out by removing the kidneys from animals when they are culled at the end of the study. These are homogenised in saline and plated onto Sabourauds agar and incubated at 35° C. for 72 h. *Aspergillus* colonies are counted and the amount of *aspergillus* per gram of kidney calculated. The results are expressed as colony forming units per gramme (cfu/g). One of the problems with tissue burden studies is the lack of comparable controls, as vehicle treated animals all die before the end of the study. However, data from studies where tissue burden has been carried out on untreated animals at day 4 or 5 has shown that tissue burdens are typically in excess of 20,000 cfu/g and may exceed 100,000 cfu/g in some studies.

Galactomannan Measurements

Galactomannan is a carbohydrate material present in the cell wall of *aspergillus*. As the organism grows galactomannan is secreted into the extracellular medium. It can be found in the plasma of infected humans and animals, and its presence is a strong indicator of active disease. Detection of galactomannan in human plasma is now considered an important diagnostic test for human aspergillosis. More recently it has been shown that successful treatment of aspergillosis with drugs such as voriconazole can reduce galactomannan concentrations in serum in both humans and animals, allowing sequential galactomannan indices to be used as a measure of therapeutic efficacy. Galactomannan measurements can potentially be a useful biomarker for assessing the response to antifungal therapy in clinical trials. Rising levels indicate therapeutic failure whilst falling levels indicate therapeutic success. However, the echinocandin drugs such as caspofungin although they are efficacious in animal models of aspergillosis do not reduce galactomannan levels. The purpose of this work was to determine if Example 1 reduced galactomannan levels in mouse aspergillosis infection models and whether this could be used as a marker to predict efficacy in future work.

In some of the survival studies described below serum samples were collected from surviving mice at the end of the study or on mice that succumbed to infection during the study to examine the effect of Example 1 on galactomannan levels and to see if there was a relationship between galactomannan levels and survival.

The galactomannan assays were carried out on serum samples that had been stored frozen at −80° C. Samples were thawed and assayed using a Platelia *Aspergillus* Ag enzyme-linked immunosorbent assay (ELISA) kit (Biorad). The assay was modified slightly to take into account the small sample volumes available from mice. If assay results were high a repeat test was carried out on a sample diluted in normal mouse serum. The amount of galactomannan in a sample is presented as a galactomannan index. The mean galactomannan index for each group was calculated and is presented graphically against each treatment regimen.

Survival Study

Figure 5:
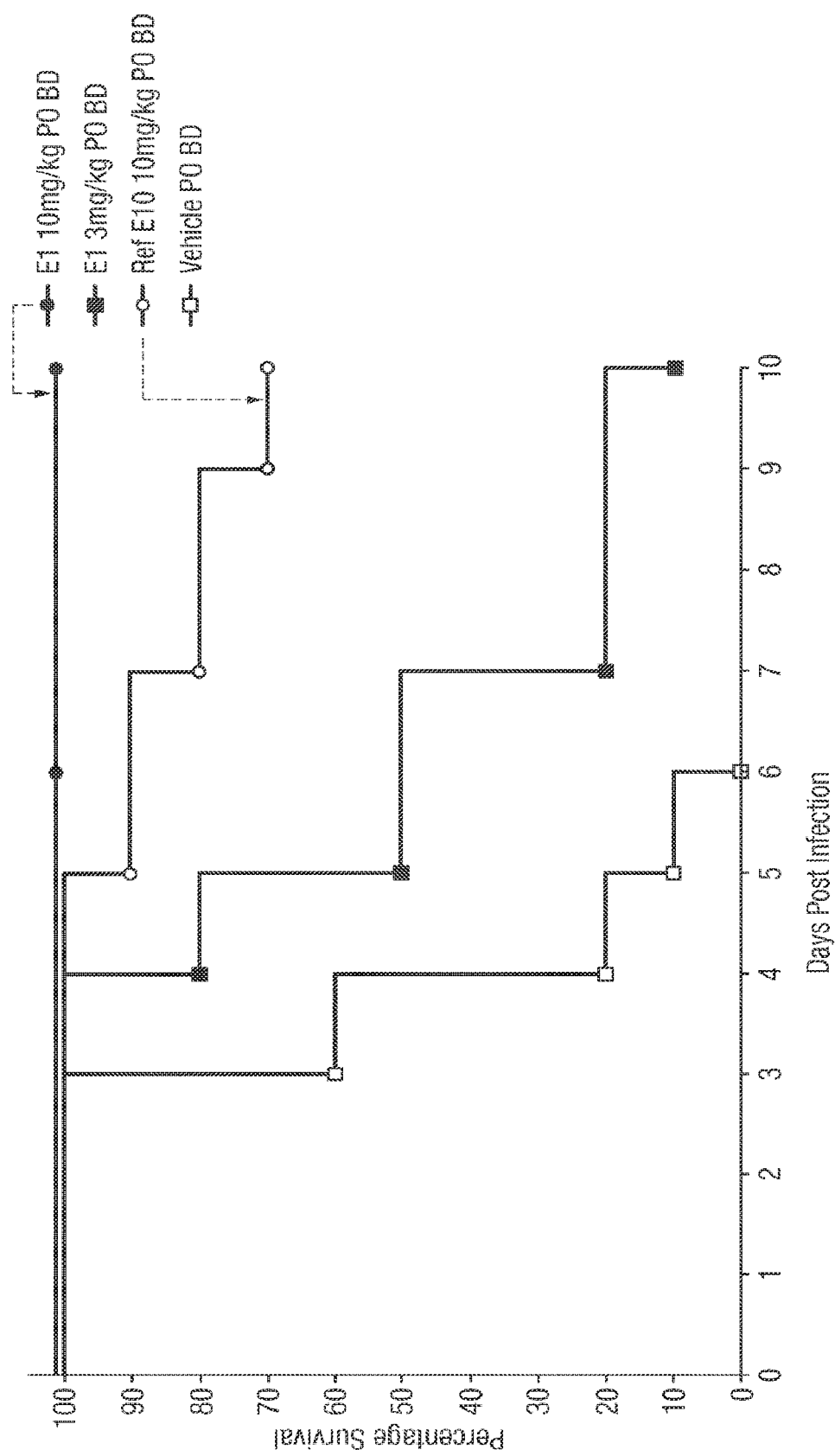
FIG. 5 provides the survival curves obtained in a survival study, discussed below, which looked at the survival of mice receiving various oral dosages of 2-(1, 5-Dimethyl-3-phenyl-1H-pyrro-2-yl)-N-{4-[4-(5-fluoro-pyrimidin-2-yl)-piperazin-1-yl]-phenyl}-2-oxo-acetamide.

The survival study carried assessed the dose response of Example 1. Example 1 was dosed orally to *A. fumigatus* infected mice at 2 dose levels 10 mg/kg b.i.d. and 3 mg/kg b.i.d. Therapy was initiated at 24 h post infection and therapy continued for 8 days. At the end of the study kidney burdens were measured on surviving animals. In addition serum samples were taken at the end of the study from all surviving animals and from each animal that died during the course of the study. These were stored frozen at −80° C. for galactomannan measurements. The survival curves are shown in FIG. 5.

This study shows that Example 1 dosed orally at 10 mg/kg b.i.d. gives excellent efficacy in murine models of invasive aspergillosis. Oral doses of 3 mg/kg b.i.d. Example 1 show some efficacy in this model but are unable to prevent death in all animals. End of study tissue burdens were 1114 cfu/gm and 3021 cfu/gm for 10 mg/kg b.i.d. and 3 mg/kg b.i.d. respectively.

Figure 6:
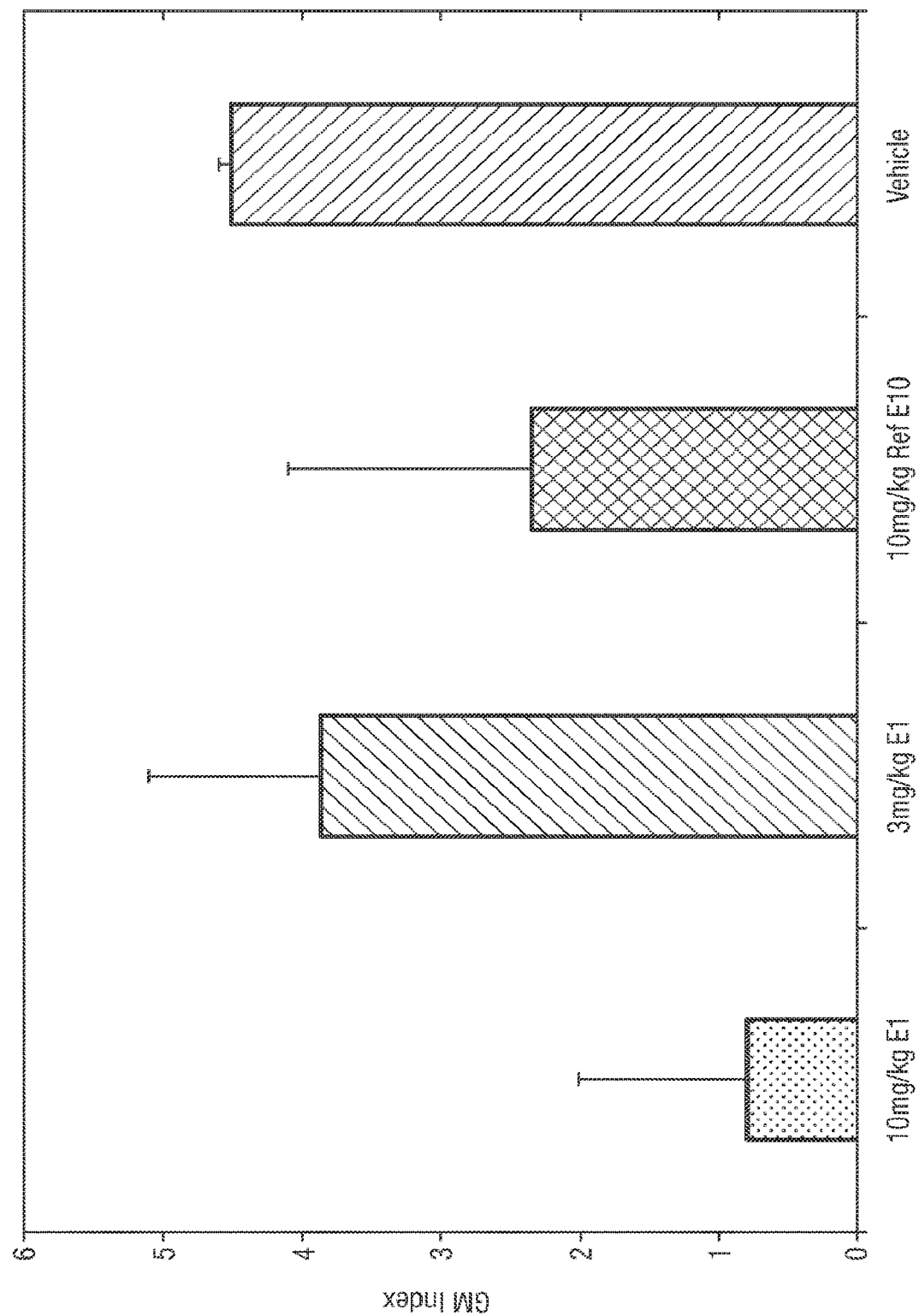
FIG. 6 provides the mean serum galactomannan indices obtained in the survival study.

The galactomannan indices obtained in survival study 3 are shown in FIG. 6. The 10 mg/kg b.i.d. dose of Example 1 which produced 100% survival at end of study produced very low galactomannan indices. The animals treated with the 3 mg/kg b.i.d. dose of Example 1 produced only 10% survival at the end of study and the galactomannan indices were correspondingly high, of a similar magnitude to those from untreated animals. This clearly demonstrates that low galactomannan indices correlate well with survival, and that when dosed orally at a suitable dose Example 1 is able to reduce galactomannan indices in *A. fumigatus* infected mice.

*Lomentospora prolificans* FMR 3569 Against Example 1 in Disseminated Infection Model Culture

*L. prolificans* (also known as *Scedosporium prolificans* or *S. prolificans*) was grown on Potato Dextrose Agar (PDA) for 5 days at 35° C. On the day of infection, cultures were flooded with sterile saline and filtered through sterile gauze to remove clumps of conidia and hyphae. The resulting suspensions were adjusted by haemocytometer count and by serial plating to confirm viability.

Animals

Male OF-1 mice with a mean weight of 30 g were used in the experiment. Mice were housed in standard boxes with food and water ad libitum. All animal procedures were supervised and approved by the Universitat Rovira i Virgili Animal Welfare and Ethics Committee.

Immunosuppression

Mice were rendered neutropenic two days prior to infection by an intraperitoneal (i.p.) injection of 200 mg/kg of cyclophosphamide, and once every 5 days thereafter (Clemons et al, 2005).

Infection

Mice were challenged with $5 \times 10^4$ CFU/animal of *L. prolificans* FMR 3569, in a volume of 0.2 ml of sterile saline into the lateral tail vein.

Treatment

Treatments consisted of (a) voriconazole (VRC) (Vfend; Pfizer S. A., Madrid, Spain) at 25 mg/kg p.o, by gavage QD; (b) Example 1 at 20 mg/k, p.o, by gavage BID; and (c) no treatment. From 3 days before infection, mice that received VRC were given grapefruit juice instead of water (Sugar & Liu, 2001). All treatments began 1 day after challenge, and the therapy lasted for 9 days. Controls received no treatment.

For survival studies groups of 10 mice were randomly established for each therapy. Mortality was recorded daily until the end of the experiment. For tissue burden studies groups of 5 animals were performed. Mice were checked twice a day, on day 13 post infection tissue burden groups were euthanized by C02 anoxia. Lung, kidney and brain were removed, homogeneized in sterile saline and plated onto PDA for CFU/g of tissue calculation.

Statistical Analysis

The mean survival times (MST) were estimated by the Kaplan-Meier method and compared among groups by using the log rank test. In tissue burden studies, colony counts were $\log_{10}$-transformed and compared by the two-tailed Mann-Whitney U-test, using Graph Pad Prism 5 for Windows. P values ≤0.05 were considered statistically significant.

Survival Results

Survival results are presented in FIG. 7. It is clear from the data presented that the use of voriconazole provides no significant increase in the survival rates when compared with the control. Example 1, in contrast, provides improved survival rates.

Survival Statistics

| Treatment | Control | VRC | Example 1 |
|---|---|---|---|
| Control | — | — | — |
| VRC | 0.89 | — | — |
| Example 1 | 0.159 | 0.01 | — |

Tissue Burden Statistics

| Organ | Lung (control) | Kidney (control) | Brain (control) |
|---|---|---|---|
| Lung (VRC 25 mg/kg) | 0.4 | — | — |
| Kidney (VRC 25 mg/kg) | — | >0.99 | — |
| Brain (VRC 25 mg/kg) | — | — | 0.62 |
| Lung (Example 1 20 mg/k BID) | 0.0396 | — | — |
| Kidney (Example 1 20 mg/k BID) | — | 0.07 | — |

-continued

| | | | |
|---|---|---|---|
| Brain (Example 1 20 mg/k BID) | — | — | 0.13 |

| | Lung (VRC 25 mg/k) | Kidney (VRC 25 mg/k) | Brain (VRC 25 mg/k) |
|---|---|---|---|
| Lung (Example 1 20 mg/k BID) | 0.22 | — | — |
| Kidney (Example 1 20 mg/k BID) | — | 0.01 | — |
| Brain (Example 1 20 mg/k BID) | — | — | 0.0412 |

The invention claimed is:

1. A method of treating asthma, COPD, bronchiectasis, cystic fibrosis, rhinosinusitis or sinusitis in a subject in need thereof, comprising administering to said subject an effective amount of:
2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof.

2. The method according to claim 1, wherein 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, is administered intravenously.

3. The method according to claim 1, wherein the method is for treating severe asthma with fungal sensitisation (SAFS).

4. The method according to claim 1, comprising administering to said subject an effective amount of a pharmaceutical composition comprising:
2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, together with one or more pharmaceutically acceptable carriers and/or excipients.

5. The method according to claim 4, wherein the pharmaceutical composition is administered intravenously.

6. The method according to claim 4, wherein the method is for treating severe asthma with fungal sensitisation (SAFS).

7. A method of treating a fungi exacerbated allergic response in a subject, wherein the subject has asthma, comprising administering to said subject an effective amount of:
2-(1,5-dimethyl-3-phenyl-1H-pyrrol-2-yl)-N-(4-(4-(5-fluoropyrimidin-2-yl)piperazin-1-yl)phenyl)-2-oxoacetamide, or
a pharmaceutically acceptable salt thereof.

8. The method according to claim 7, wherein 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, is administered intravenously.

9. The method according to claim 7, wherein the method is for treating severe asthma with fungal sensitisation (SAFS).

10. The method according to claim 7, comprising administering to said subject an effective amount of a pharmaceutical composition comprising:
2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof, together with one or more pharmaceutically acceptable carriers and/or excipients.

11. The method according to claim 10, wherein the pharmaceutical composition is administered intravenously.

12. The method according to claim 10, wherein the method is for treating severe asthma with fungal sensitisation (SAFS).

13. A method of treating asthma, COPD, bronchiectasis, cystic fibrosis, rhinosinusitis or sinusitis in a subject in need thereof, comprising administering to said subject an effective amount of a pharmaceutical combination comprising:
(i) 2-(1,5-dimethyl-3-phenyl-1H-pyrrol-2-yl)-N-(4-(4-(5-fluoropyrimidin-2-yl)piperazin-1-yl)phenyl)-2-oxoacetamide, or a pharmaceutically acceptable salt thereof; and
(ii) a second antifungal agent.

14. The method according to claim 13, wherein components (i) and (ii) are formulated for separate, simultaneous, or successive administration.

15. The method according to claim 13, wherein the second antifungal agent is selected from the group consisting of azoles, polyenes, purine nucleotide inhibitors, pyrimidine nucleotide inhibitors, mannan inhibitors, protein elongation factor inhibitors, echinocandins, allylamines, anti-HSP90 antibodies, bactericidal/permeability inducing protein products, polyoxins, 5-fluoro-1,3-dihydro-1-hydroxy-2,1-benzoxaborale, 5-chloro-1,3-dihydro-1-hydroxy-2,1-benzoxaborale, icofungipen, VT116, and SCY078.

16. The method according to claim 15, wherein the second antifungal agent is: (a.i) an azole selected from the group consisting of clotrimazole, econazole, bifonazole, butoconazole, fenticonazole, fluconazole, isoconazole, itraconazole, ketoconazole, miconazole, oxiconazole, sertaconazole, sulconazole, tioconazole, isavuconazole, ravuconazole, posaconazole, terconazole, and voriconazole; (a.ii) an echinocandin selected from the group consisting of anidulafungin, caspofungin, and micafungin; (a.iii) an allylamine selected from the group consisting of terbinafine, butenafine, amorolfine, and naftifine; (a.iv) a polyene selected from the group consisting of amphotericin B and nystatin; (a.v) a purine or pyrimidine nucleotide inhibitor which is flucytosine; (a.vi) a mannan inhibitor which is pradamicin; (a.vii) a protein elongation factor inhibitor selected from the group consisting of sordarin and analogues thereof; or (a.viii) a polyoxin which is nikkomycin Z.

17. The method according to claim 4, further comprising administering a second antifungal agent, and one or more pharmaceutically acceptable carriers and/or excipients.

18. The method according to claim 13, wherein the pharmaceutical combination is administered intravenously.

19. The method according to claim 13, wherein the method is for treating severe asthma with fungal sensitisation (SAFS).

* * * * *

UNITED STATES PATENT AND TRADEMARK OFFICE
CERTIFICATE OF CORRECTION

PATENT NO. : 10,596,150 B2
APPLICATION NO. : 16/222764
DATED : March 24, 2020
INVENTOR(S) : Graham Edward Morris Sibley et al.

It is certified that error appears in the above-identified patent and that said Letters Patent is hereby corrected as shown below:

On the Title Page
On page 6, at the right-hand column, under Other Publications, Line 32, delete "☐-Ketoamides" and insert --α-Ketoamides--;

In the Specification
At Column 1, Line number 42, delete "haemopoetic" and insert --haemopoietic--;
At Column 1, Line number 49, delete "brochiectasis" and insert --bronchiectasis--;
At Column 2, Line number 5, delete "1-glucan" and insert --β-glucan--;
At Column 2, Line numbers 9-10, delete "flucyotosine" and insert --flucytosine--;
At Column 2, Line number 13, delete "1-glucan" and insert --β-glucan--;
At Column 2, Line number 54, delete "derivates" and insert --derivatives--;
At Column 2, Line number 58, delete "pyrro" and insert --pyrrol--;
At Column 4, Line number 34, delete "pyrro" and insert --pyrrol--;
At Column 8, Line number 13, delete "piperidonyl," and insert --piperidinyl,--;
At Column 9, Line numbers 21-40, insert --or-- at the end of the line;
At Column 9, Line numbers 46-65, insert --or-- at the end of the line;
At Column 10, Line numbers 48-65, insert --or-- at the end of the line;
At Column 11, Line numbers 5-20, insert --or-- at the end of the line;
At Column 12, Line number 48, delete "derivates" and insert --derivatives--;
At Column 13, Line number 39, delete "benzoxaborale" and insert --benzoxaborole--;
At Column 13, Line number 40, delete "benzoxaborale" and insert --benzoxaborole--;
At Column 13, Line number 48, delete "benzoxaborale" and insert --benzoxaborole--;
At Column 13, Line number 49, delete "benzoxaborale" and insert --benzoxaborole--;
At Column 14, Line number 36, delete "pradamicin." and insert --pradimicin.--;
At Column 14, Line number 40, delete "anidulofungin," and insert --anidulafungin,--;
At Column 15, Line number 6, delete "TH" and insert --1H--;
At Column 16, Line number 63, delete "edeate;" and insert --edetate;--;
At Column 18, Line number 8, delete "Colletotrichium;" and insert --Colletotrichum;--;
At Column 18, Line number 11, delete "Neurospora," and insert --Neurospora;--;
At Column 18, Line number 31, delete "cladosporoides;" and insert --cladosporioides;--;

Signed and Sealed this
Twenty-ninth Day of December, 2020

Andrei Iancu
*Director of the United States Patent and Trademark Office*

CERTIFICATE OF CORRECTION (continued)
U.S. Pat. No. 10,596,150 B2

At Column 18, Line number 32, delete "immitis," and insert --immitis;--;
At Column 18, Line number 33, delete "Colletotrichium" and insert --Colletotrichum--;
At Column 18, Line number 36, delete "sporotrichoides;" and insert --sporotrichioides;--;
At Column 18, Line number 50, delete "A," and insert --A.--;
At Column 19, Line numbers 23-24, delete "mucomycosis;" and insert --mucormycosis;--;
At Column 19, Line numbers 24-25, delete "coccidiomycosis; paracoccidiomycosis;" and insert --coccidioidomycosis; paracoccidioidomycosis;--;
At Column 19, Line number 27, delete "sporotrichosis," and insert --sporotrichosis.--;
At Column 19, Line number 27, delete "aspergillosiis" and insert --aspergillosis--;
At Column 20, Line number 51, delete "Colletotrichium" and insert --Colletotrichum--;
At Column 20, Line number 52, delete "graminearium;" and insert --graminearum;--;
At Column 20, Line number 52, delete "sporotrichoides;" and insert --sporotrichioides;--;
At Column 21, Line number 11, insert --.-- at the end of the line;
At Column 26, Line number 31, delete "H" and insert --1H--;
At Column 26, Line number 31, delete "24" and insert --2, 4--;
At Column 27, Line number 26, delete "12" and insert --1/2--;
At Column 28, Line number 51, insert --.-- at the end of the line;
At Column 28, Line number 52, delete "Phenyl Piperazine" and insert --phenyl piperazine--;
At Column 30, Line number 14, delete "pyrro" and insert --pyrrol--;
At Column 30, Line number 59, delete "pyrro" and insert --pyrrol--;
At Column 30, Line number 60, delete "1yl]" and insert --1-yl]--;
At Column 30, Line number 62, delete "pyrro" and insert --pyrrol--;
At Column 35, Line numbers 46-47, delete "phe-nyl2" and insert --phe-nyl-2--;
At Column 38, Line number 37, delete "mLL)" and insert --mL)--;
At Column 40, Line number 17, insert --.-- at the end of the line;
At Column 40, Line number 20, insert --.-- at the end of the line;
At Column 40, Line number 23, insert --.-- at the end of the line;
At Column 40, Line number 60, delete "pyrro" and insert --pyrrol--;
At Column 40, Line number 61, delete "1yl]" and insert --1-yl]--;
At Column 41, Line number 13, delete "Sabarauds" and insert --Sabourauds--;
At Column 42, Line number 6, delete "dermatitidis," and insert --dermatitidis;--;
At Column 42, Line number 10, delete "Colletotrichium" and insert --Colletotrichum--;
At Column 42, Line number 11, delete "Colletotrichium" and insert --Colletotrichum--;
At Column 42, Line number 15, delete "graminearium;" and insert --graminearum;--;
At Column 42, Line number 16, delete "sporotrichoides;" and insert --sporotrichioides;--;
At Column 46, Line number 30, delete "C02" and insert --$CO_2$--;
At Column 46, Line number 31, delete "homogeneized" and insert --homogenized--;

In the Claims
At Column 48, Claim number 15, Line numbers 38-39, delete "benzoxaborale," and insert --benzoxaborole,--;
At Column 48, Claim number 15, Line numbers 39-40, delete "benzoxaborale," and insert --benzoxaborole,--;
At Column 48, Claim number 16, Line number 55, delete "pradamicin;" and insert --pradimicin;--.